(12) United States Patent
Tso et al.

(10) Patent No.: US 8,952,134 B2
(45) Date of Patent: Feb. 10, 2015

(54) HYBRID CONSTANT REGIONS

(71) Applicants: J. Yun Tso, Menlo Park, CA (US);
Naoya Tsurushita, Palo Alto, CA (US)

(72) Inventors: J. Yun Tso, Menlo Park, CA (US);
Naoya Tsurushita, Palo Alto, CA (US)

(73) Assignee: JN Biosciences LLC, Mountain View, CA (US)

( * ) Notice: Subject to any disclaimer, the term of this patent is extended or adjusted under 35 U.S.C. 154(b) by 18 days.

(21) Appl. No.: 13/627,929

(22) Filed: Sep. 26, 2012

(65) Prior Publication Data

US 2013/0089547 A1    Apr. 11, 2013

Related U.S. Application Data

(60) Provisional application No. 61/539,416, filed on Sep. 26, 2011.

(51) Int. Cl.
| | |
|---|---|
| C07K 16/46 | (2006.01) |
| C07K 19/00 | (2006.01) |
| C12P 21/08 | (2006.01) |
| A61K 39/395 | (2006.01) |
| C07K 16/28 | (2006.01) |
| C07K 16/00 | (2006.01) |
| A61K 39/00 | (2006.01) |

(52) U.S. Cl.
CPC ............. *C07K 16/46* (2013.01); *C07K 2319/21* (2013.01); *C07K 2319/00* (2013.01); *C07K 2317/35* (2013.01); *A61K 2039/505* (2013.01); *C07K 16/2878* (2013.01); *C07K 16/2803* (2013.01); *C07K 16/468* (2013.01); *C07K 16/00* (2013.01); *C07K 2317/73* (2013.01)
USPC ................ 530/387.3; 530/388.22; 530/389.7; 530/391.3; 424/133.1; 424/143.1; 424/152.1

(58) Field of Classification Search
CPC combination set(s) only.
See application file for complete search history.

(56) References Cited

U.S. PATENT DOCUMENTS

| | | | |
|---|---|---|---|
| 7,148,321 B2 * | 12/2006 | Gillies et al. .................. | 530/300 |
| 7,754,208 B2 * | 7/2010 | Ledbetter et al. .......... | 424/133.1 |
| 7,951,378 B2 | 5/2011 | Larrick et al. | |
| 2004/0175786 A1 | 9/2004 | Choi et al. | |

FOREIGN PATENT DOCUMENTS

| | | |
|---|---|---|
| WO | WO 2008/148884 A1 | 12/2008 |
| WO | WO 2013/049254 A1 | 4/2013 |

OTHER PUBLICATIONS

Schaffner et al., Mol Immunol. Jan. 1995;32(1):9-20.*
Smith et al., J Immunol. Mar. 1, 1995;154(5):2226-2236.*
Olafsen et al., Immunotechnology. Oct. 1998;4(2):141-153.*
Braathen et al., Biol Chem. Nov. 8, 2002;277(45):42755-62.*
Barfod et al., "Evasion of immunity to Plasmodium falciparum malaria by IgM masking of protective IgG epitopes in infected erythrocyte surface-exposed PfEMP1," PNAS, 108(30):12485-12490, (2011).
Caron et al., "Engineered Humanized Dimeric Forms of IgG Are More Effective Antibodies," J. Exp. Med., 176:1191-1195, (1992).
Cosman, "A Family of Ligands for the TNF Receptor Superfamily," Stem Cells, 12:440-455, (1994).
Cuesta et al., "Multivalent antibodies: when design surpasses evolution," Trends in Biotechnology, 28:355-362, (2010).
Ghumra et al., "Structural requirements for the interaction of human IgM and IfA with the human Fcα/μ receptor," Eur. J. Immunol., 39:S1147-1156, (2009).
Griffith et al., "Functional Analysis of TRAIL Receptors Using Monoclonal Antibodies," J Immunol, 162:2597-2605, (1999).
Matsuno et al., "Antirheumatic effects of humanized anti-Fas monoclonal antibody in human rheumatoid arthritis/SCID mouse chimera," J Rheumatol, 29(8):1609-1614, (2002).
Miller et al., "Design, Construction, and in Vitro Analyses of Multivalent Antibodies," J Immunol, 170:4854-4861, (2003).
Rossi et al., "Novel Designs of Multivalent Anti-CD20 Humanized Antibodies as Improved Lymphoma Therapeutics," Cancer Res, 68(20):8384-8392, (2008).
Sorensen et al., "Effect of the IgM and IgA Secretory Tailpieces on Polymerization and Secretion of IgM and 1g0," The Journal of Immunology, 156:2858-2865, (1996).
Sorensen et al., "Structural requirements for incorporation of J chain into human IgM and IgA," International Immunology, 12(1):19-27, (2000).
WIPO Application No. PCT/US2012/057393, PCT International Preliminary Report on Patentability mailed Jan. 10, 2014.
WIPO Application No. PCT/US2012/057393, PCT International Search Report and Written Opinion of the International Searching Authority mailed Feb. 28, 2013.
Yonehara et al., "A Cell-Killing Monoclonal Antibody (Anti-Fas) To a Cell Surface Antigen Co-Downregulated with the Receptor of Tumor Necrosis Factor," J. Exp. Med., 169:1747-1756, (1989).
Yoo et al., "Structural Requirements for Polymeric immunoglobulin Assembly and Association with J Chain," The Journal of Biological Chemistry, 274(47):33771-33777, (1999).

* cited by examiner

*Primary Examiner* — Daniel C Gamett
(74) *Attorney, Agent, or Firm* — Alston & Bird LLP

(57) ABSTRACT

The invention provides hybrid constant regions and antibodies or fusion proteins incorporating the same. The hybrid constant regions include at least CH2 and CH3 regions of an IgG or IgA constant region and $C\mu3$ and $C\mu4$ regions of a $C\mu$ constant region. The hybrids retain properties of both component constant regions. The hybrids retain the ability of a $C\mu$ constant region to form multivalent complexes, e.g., pentameric or hexameric structures. IgG hybrids also retain IgG properties including pH-dependent FcRn binding, which is associated with a relatively long in vivo half-life, and specific binding to protein G, which facilitates purification. Depending on the isotype and subtype, the nature of the antigen and presence of additional IgG CH1 and hinge domains, IgG hybrids may also retain properties of specific binding to protein A, and effector functions ADCC, CDC and opsonization. IgA hybrids retain the property of IgA of binding to an Fc-alpha receptor CD89.

28 Claims, 20 Drawing Sheets

Elution Pattern of Superose 6 Gel Filtration
A. Molecular Weight Standards
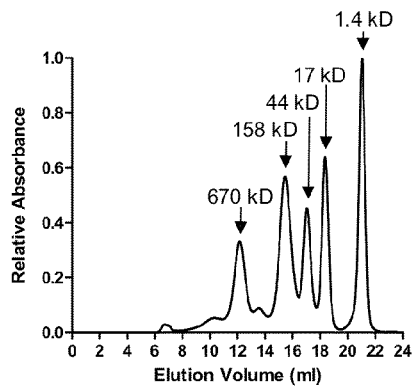
B. Human IgM
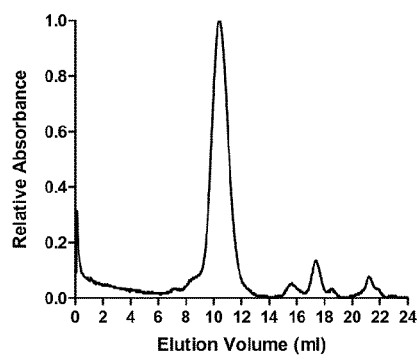
C. Ch9G6-IgG1
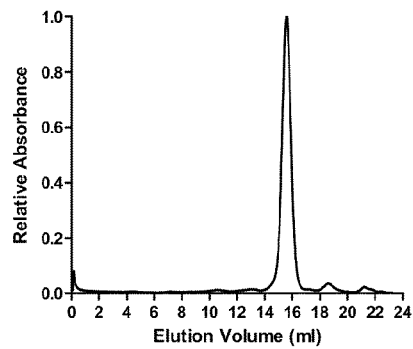
D. Ch9G6-IgG1/M
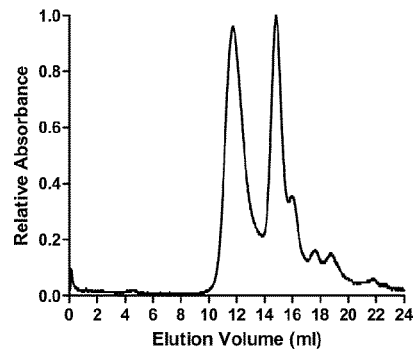
E. Ch9G6-MVIgG1
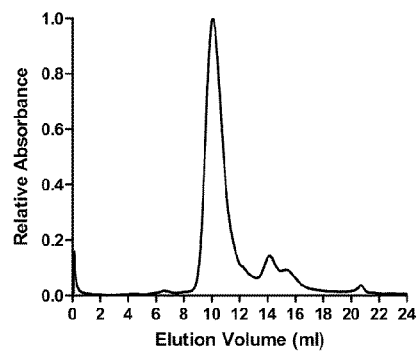
Figures 3A-E pH-Dependent Binding of Multivalent IgG1 to FcRn

|  |  | Mean Channel Fluorescence | |
| --- | --- | --- | --- |
| Primary Antibody | PE-labeled Secondary Antibody | pH 6.0 | pH 7.5 |
| None | Goat anti-human gamma chain | 4.2 | 3.3 |
| None | Goat anti-human mu chain | 8.7 | 4.1 |
| Ch9G6-IgG1 | Goat anti-human gamma chain | 324.9 | 11.3 |
| Ch9G6-IgG1/M | Goat anti-human mu chain | 19.4 | 3.4 |
| Ch9G6-MVIgG1 | Goat anti-human mu chain | 765.8 | 107.0 |

Elution Pattern of Superose 6 Gel Filtration
A. Molecular Weight Standards
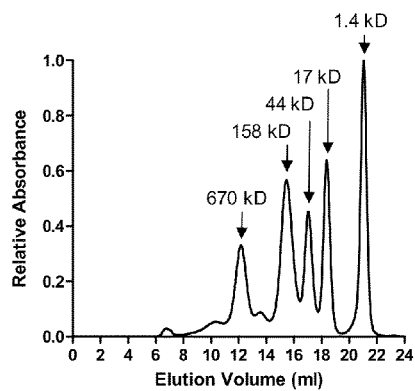
B. Human IgM
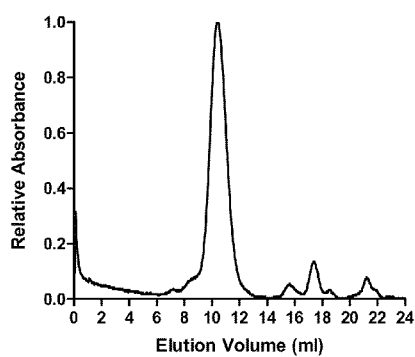
C. Ch9G6-MVIgG4
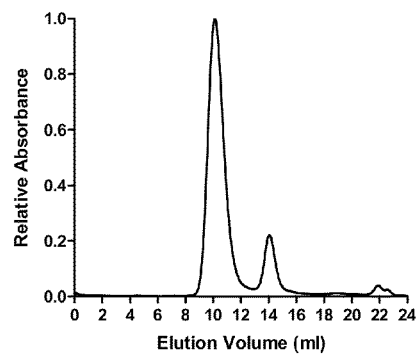
Figures 12A-C

Elution Pattern of Superose 6 Gel Filtation
A. Molecular Weight Standards
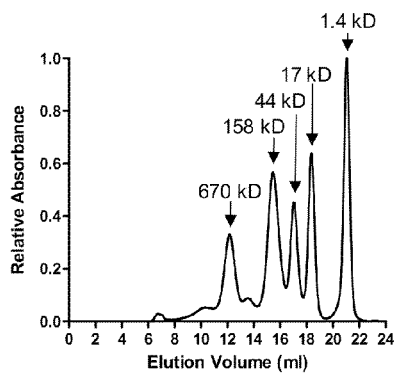
B. Human IgM
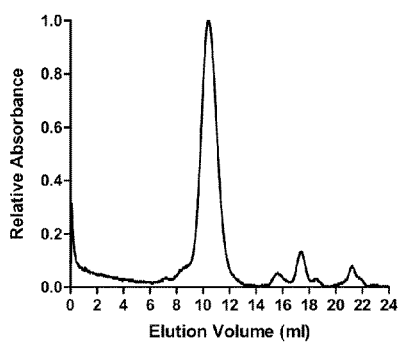
C. Ch9G6-IgG3D
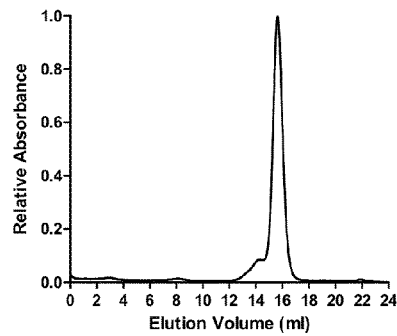
D. Ch9G6-IgG3D/M
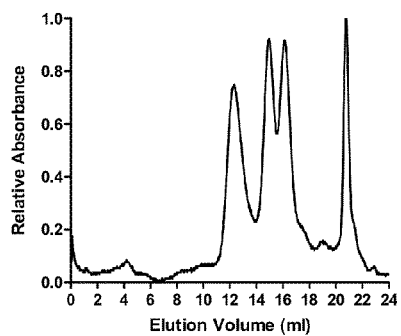
E. Ch9G6-MVIgG3D
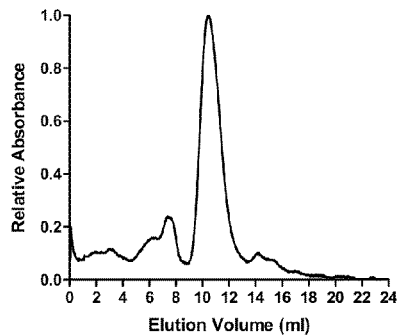
Figures 13A-E pH-Dependent Binding of Multivalent IgG3 to FcRn

| Primary Antibody | PE-labeled Secondary Antibody | Mean Channel Fluorescence | |
|---|---|---|---|
| | | pH 6.0 | pH 7.5 |
| None | Goat anti-human gamma chain | 4.2 | 3.3 |
| None | Goat anti-human mu chain | 8.7 | 4.1 |
| Ch9G6-IgG3D | Goat anti-human gamma chain | 447.4 | 20.6 |
| Ch9G6-IgG3D/M | Goat anti-human mu chain | 11.4 | 3.2 |
| Ch9G6-MVIgG3D | Goat anti-human mu chain | 962.1 | 146.5 |

Figure 14

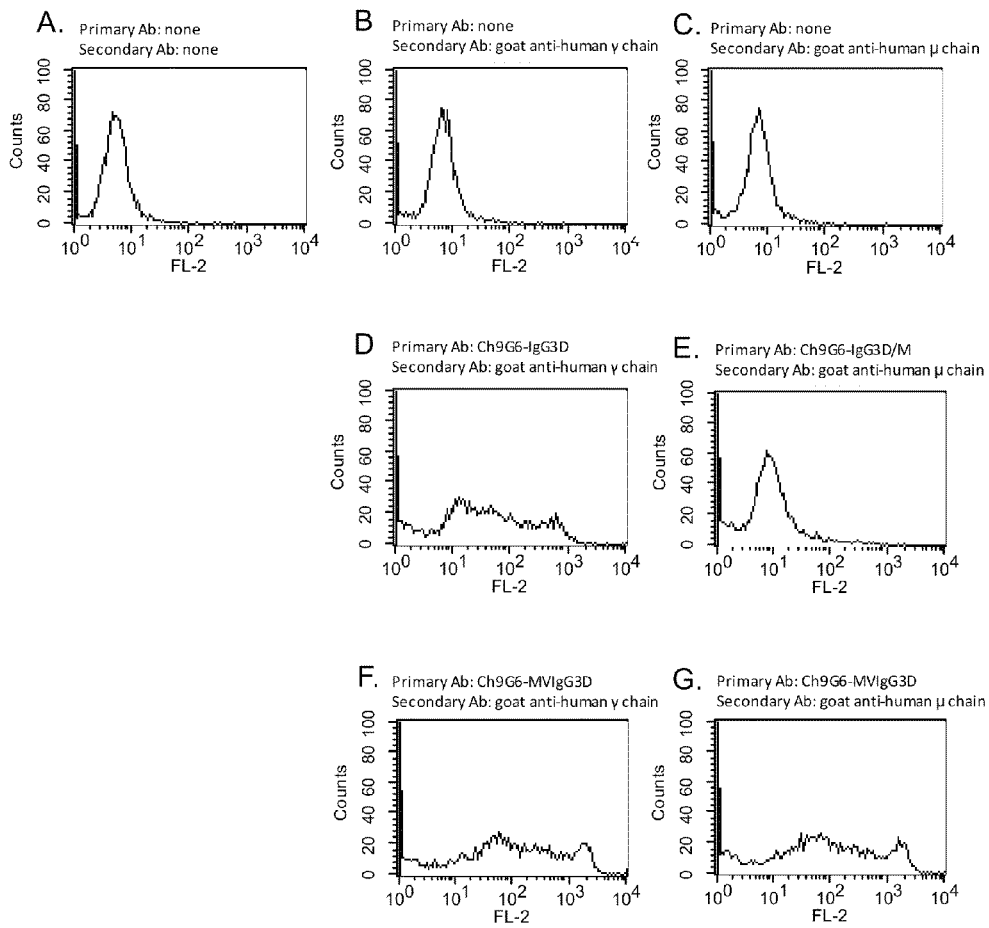
Figures 15A-G

Figure 16A

Human gamma-1 heavy chain constant region

CH1:ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKV (SEQ ID NO:15)

Hinge:EPKSCDKTHTCPPCP (SEQ ID NO:16)

CH2:APELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK (SEQ ID
NO:17)

CH3:GQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK (SEQ ID NO:18)

Human gamma-2 heavy chain constant region

CH1:ASTKGPSVFPLAPCSRSTSESTAALGCLVKDYFPEPVTVSWNSGALTSGVHTFPAVLQSS
GLYSLSSVVTVPSSNFGTQTYTCNVDHKPSNTKVDKTV (SEQ ID NO:19)

Hinge:ERKCCVECPPCP (SEQ ID NO:20)

CH2:APPVAGPSVFLFPPKPKDTLMISRTPEVTCVVVDVSHEDPEVQFNWYVDGVEVHNAKTKP
REEQFNSTFRVVSVLTVVHQDWLNGKEYKCKVSNKGLPAPIEKTISKTK (SEQ ID NO:21)

CH3:GQPREPQVYTLPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGK (SEQ ID NO:22)

Human gamma-3 heavy chain constant region

CH1:ASTKGPSVFPLAPCSRSTSGGTAALGCLVKDYFPEPVTVSWNSGALTSGVHTFPAVLQSS
GLYSLSSVVTVPSSSLGTQTYTCNVNHKPSNTKVDKRV (SEQ ID NO:23)

Hinge:ELKTPLGDTTHTCPRCPEPKSCDTPPPCPRCPEPKSCDTPPPCPRCPEPKSCDTPPPC
PRCP (SEQ ID NO:24)

CH2:APELLGGPSVFLFPPKPKDTLMISRTPEVTCVVVDVSHEDPEVQFKWYVDGVEVHNAKTK
PREEQYNSTFRVVSVLTVLHQDWLNGKEYKCKVSNKALPAPIEKTISKTK (SEQ ID
NO:25)

CH3:GQPREPQVYTLPPSREEMTKNQVSLTCLVKGFYPSDIAVEWESSGQPENNYNTTPPMLDS
DGSFFLYSKLTVDKSRWQQGNIFSCSVMHEALHNRFTQKSLSLSPGK (SEQ ID NO:26)

Figure 16B

Human gamma-4 heavy chain constant region

CH1:ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRV (SEQ ID NO:27)

Hinge:ESKYGPPCPSCP (SEQ ID NO:28)

CH2:APEFLGGPSVFLFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKAK (SEQ ID
NO:29)

CH3:GQPREPQVYTLPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK (SEQ ID NO:30)

Human alpha-1 heavy chain constant region

CH1:ASPTSPKVFPLSLCSTQPDGNVVIACLVQGFFPQEPLSVTWSESGQGVTARNFPPSQDAS
GDLYTTSSQLTLPATQCLAGKSVTCHVKHYTNPSQDVTVPCP (SEQ ID NO:31)

CH2:VPSTPPTPSPSTPPTPSPSCCHPRLSLHRPALEDLLLGSEANLTCTLTGLRDASGVTFTW
TPSSGKSAVQGPPERDLCGCYSVSSVLPGCAEPWNHGKTFTCTAAYPESKTPLTATLSKS
(SEQ ID NO:32)

CH3:GNTFRPEVHLLPPPSEELALNELVTLTCLARGFSPKDVLVRWLQGSQELPREKYLTWASR
QEPSQGTTTFAVTSILRVAAEDWKKGDTFSCMVGHEALPLAFTQKTIDRLAGKPTHVNVSVVMA
EVDGTCY (SEQ ID NO:33)

Human alpha-2 heavy chain constant region

CH1:ASPTSPKVFPLSLDSTPQDGNVVVACLVQGFFPQEPLSVTWSESGQNVTARNFPPSQDAS
GDLYTTSSQLTLPATQCPDGKSVTCHVKHYTNPSQDVTVPCP (SEQ ID NO:34)

CH2:VPPPPPCCHPRLSLHRPALEDLLLGSEANLTCTLTGLRDASGATFTWTPSSGKSAVQGPP
ERDLCGCYSVSSVLPGCAQPWNHGETFTCTAAHPELKTPLTANITKS (SEQ ID NO:35)

CH3:GNTFRPEVHLLPPPSEELALNELVTLTCLARGFSPKDVLVRWLQGSQELPREKYLTWASR
QEPSQGTTTFAVTSILRVAAEDWKKGDTFSCMVGHEALPLAFTQKTIDRLAGKPTHVNVSVVMA
EVDGTCY (SEQ ID NO:36)

Figure 16C

Human mu heavy chain constant region

Cμ1:GSASAPTLFPLVSCENSPSDTSSVAVGCLAQDFLPDSITFSWKYKNNSDISSTRGFPSVL
RGGKYAATSQVLLPSKDVMQGTDEHVVCKVQHPNGNKEKNVPLP (SEQ ID NO:51)

Cμ2:VIAELPPKVSVFVPPRDGFFGNPRKSKLICQATGFSPRQIQVSWLREGKQVGSGVTTDQV
QAEAKESGPTTYKVTSTLTIKESDWLSQSMFTCRVDHRGLTFQQNASSMCVP (SEQ ID
NO:52)

Cμ3:DQDTAIRVFAIPPSFASIFLTKSTKLTCLVTDLTTYDSVTISWTRQNGEAVKTHTNISES
HPNATFSAVGEASICEDDWNSGERFTCTVTHTDLPSPLKQTISRPK (SEQ ID NO:53)

Cμ4:GVALHRPDVYLLPPAREQLNLRESATITCLVTGFSPADVFVQWMQRGQPLSPEKYVTSAP
MPEPQAPGRYFAHSILTVSEEEWNTGETYTCVVAHEALPNRVTERTVDKSTGKPTLYNVSLVMS
DTAGTCY (SEQ ID NO:54)

J-Chain (aa1-22=signal peptide)
MKNHLLFWGVLAVFIKAVHVKAQEDERIVLVDNKCKCARITSRIIRSSEDPNEDIVERNI
RIIVPLNNRENISDPTSPLRTRFVYHLSDLCKKCDPTEVELDNQIVTATQSNICDEDSAT
ETCYTYDRNKCYTAVVPLVYGGETKMVETALTPDACYPD (SEQ ID NO:55)

HYBRID CONSTANT REGIONS

CROSS-REFERENCE TO RELATED APPLICATION

The present application is a non-provisional of U.S. Ser. No. 61/539,416; filed Sep. 26, 2011.

BACKGROUND

Antibodies are glycoproteins produced by B cells that play an essential role in the immune system (Schroeder et al., J. Allergy Clin. Immunol. 125:S41-S52, 2010). Five classes of antibodies, namely IgM, IgD, IgG, IgA and IgE, are produced in mammals. In humans, four subclasses of IgG (IgG1, IgG2, IgG3 and IgG4) and two subclasses of IgA (IgA1 and IgA2) antibodies are produced. Each antibody is composed of two identical light chains and two identical heavy chains in the monomeric form. These four chains are connected to one another by a combination of covalent and non-covalent bonds, and form a Y-shaped molecule. There are two types of light chains, kappa and lambda, in mammals. Several different types of heavy chains exist that define the class of an antibody. In humans, the n heavy chain is incorporated in IgM, the delta heavy chain in IgD, the gamma-1 heavy chain in IgG1, the gamma-2 heavy chain in IgG2, the gamma-3 heavy chain in IgG3, the gamma-4 heavy chain in IgG4, the alpha-1 heavy chain in IgA1, the alpha-2 heavy chain in IgA2, and the epsilon heavy chain in IgE. A monomeric form of these antibodies has two antigen binding sites, and thus is divalent for antigen binding. Although IgG, IgD and IgE are exclusively produced as a monomer, IgM is produced as a hexamer, and thus is dodecavalent for antigen binding, in the absence of J chains, and forms a decavalent pentamer when J chains are present (Gilmour et al., Trans. Med. 18:167-174, 2008). IgA forms a tetravalent dimer with a J chain, whereas IgA is a monomer when J chains are absent, although spontaneous formation of dimeric IgA without J chains has been reported (Johansen et al., Scand. J. Immunol. 52:240-248, 2000).

The U.S. Food and Drug Administration had approved twenty-eight monoclonal antibodies as human therapeutics by the end of 2010. All of these therapeutic antibodies are IgG antibodies or derivatives thereof. Besides specific antigen binding, IgG antibodies elicit various biological functions mediated by the Fc region (Schroeder et al. supra; Desjarlais et al., Exp. Cell Res. 317:1278-1285, 2011). In humans, cell-bound IgG1 and IgG3 antibodies mediate antibody-dependent cell-mediated cytotoxicity (ADCC) by binding of the Fc region to Fcγ receptor type III (CD16) expressed on NK cells (Hulett et al., Adv. Immunol. 57:1-127, 1994). Likewise, cell-bound IgG1 and IgG3 antibodies can efficiently trigger complement-dependent cytotoxicity (CDC) by the interaction of the Fc region with complement components (Bindon et al., J. Exp. Med. 168:127-142, 1988).

The Fc region of all four subclasses of human IgG antibodies binds to the neonatal Fc receptor (FcRn), which is a heterodimer composed of a transmembrane a chain and β2-microglubulin, in a pH-dependent manner, resulting in rescuing IgG antibodies internalized by pinocytosis from catabolic degradation in lysosomes and allowing their recycling to the circulation (Ghetie et al., Annu. Rev. Immunol. 18:739-766, 2000). IgG antibodies therefore exhibit slow clearance from the circulation which results in a long serum half-life, typically 23 days, in humans (Kindt et al., Chapter 4, Kuby Immunology, Sixth Edition, W. H. Freeman & Co., 2006). In addition, the Fc region of IgG antibodies bind to Protein A (except for IgG3) and Protein G, so that purification of IgG antibodies by Protein A or Protein G affinity chromatography is possible (Andrew et al., Unit 2.7, Chapter III, Current Protocols in Immunology, John Wiley & Sons, Inc. 1997).

Dimerization of specific molecules on the cell surface can often trigger one or more biological responses. Binding of monoclonal IgG antibodies to PSMA (prostate-specific membrane antigen) proteins on the cell surface increases the rate of PSMA internalization (Liu et al., Cancer Res. 58:4055-4060, 1998). Internalization and down-regulation of a type I transmembrane protein MUC1 is triggered by binding to a mouse IgG1 antibody (Hisatsune et al., Biochem. Biophys. Res. Commun 388:677-382, 2009). Monoclonal antibodies against c-Met dimerize c-Met proteins on the cell surface and initiate intracellular signals resulting in cell proliferation (Prat et al., J. Cell Sci. 111:237-247, 1998). Likewise, a monoclonal anti-EPO receptor antibody can function as an agonist for cell growth by homodimerization of EPO receptors on the surface (Schneider et al., Blood 89:473-482, 1997). Antibody-mediated dimerization of Death Receptor 5 (DR5), a member of tumor necrosis factor receptor (TNFR) super-family, on the cell surface, however, does not always trigger signal transduction, while multimerization of DR5 proteins by a mixture of mouse monoclonal anti-DR5 IgG antibody and goat anti-mouse IgG polyclonal antibody, for example, induces signal transduction in the cytoplasm and triggers apoptosis (Griffith et al., J. Immunol. 162:2597-2605, 1999).

IgM antibodies exist as pentamers with J chains and hexamers without J chains (Gilmour et al., supra). In contrast to IgG antibodies, which are only capable of dimerizing antigens, IgM can multimerize cell surface proteins due to its decavalent or dodecavalent antigen binding capability. Monoclonal IgM antibodies with specificity for Fas, a member of the TNFR superfamily (Cosman, Stem Cells 12:440-455, 1994), can efficiently induce apoptosis of Fas-expressing cells due to multimerization of Fas proteins on the surface (Yonehara et al., J. Exp. Med. 169:1747-1756, 1989) while anti-Fas IgG antibodies do not unless they are cross-linked (Matsuno et al., J. Rheumatol. 29:1609-1614, 2002). Compared to IgG, IgM exhibits a much shorter circulation half-life, typically 5 days in humans, because of its inability to bind to FcRn (Kindt et al., supra). IgM antibodies are also unable to mediate ADCC due to the lack of binding to CD16. In addition, the lack of binding to Protein A and Protein G by IgM makes it impossible to purify IgM by Protein A and Protein G affinity chromatography, respectively (Gautam et al., Biotechnol. Adv. E-publication, July 2011).

A variety of structural formats have been utilized in an attempt to generate novel forms of multivalent antibodies. Recent advances in the engineering of multivalent antibodies are summarized in a review paper of Cuesta et al. (Trends Biotech., 28:355-362, 2010). Preferred multivalent IgG antibodies are able to multimerize antigens efficiently on the cell surface. It is also important that the properties mediated by the Fc region of gamma heavy chains, such as ADCC, CDC, opsonization, pH-dependent FcRn binding, and the ability to bind to Protein A and Protein G, are maintained in such multivalent IgG antibodies.

To generate a multivalent IgG antibody, Caron et al. (J. Exp. Med., 176:1191-1195, 1992) introduced a serine-to-cysteine substitution at the fourth position from the carboxyl terminal of human gamma-1 heavy chain in the humanized anti-CD33 IgG1/kappa antibody, HuG1-M195. Such modified HuG1-M195, termed Hd-IgG, was purified and subjected to Ellman's Reagent (Pierce Chemical Co., Rockford, Ill.) for crosslinking and then blocking of excess sulfhydryl sites. Monomeric HuG1-M195 was eliminated from Hd-IgG by phenyl Sepharose column chromatography. The resultant Hd-IgG showed a dramatic improvement in the ability to internalize CD33 molecules and was more potent than HuG1-M195 at ADCC and CDC.

Miller et al. (J. Immunol., 170:4854-4861, 2003) constructed a tetravalent IgG antibody by duplicating the VH-CH1 region in the heavy chain of the humanized anti-HER2 IgG1 monoclonal antibody, hu4D5. The modified gamma heavy chain was composed of, from the N-terminus to the C-terminus, the VH, CH1, VH, CH1, hinge, CH2 and CH3 regions. One light chain bound to each of the four VH-CH1 regions in the modified IgG, forming a tetravalent hu4D5 antibody (TA-HER2). TA-HER2 was internalized more rapidly than the parental divalent hu4D5 on HER2-expressing cells. Miller et al. (supra) also constructed a tetravalent anti-DR5 IgG antibody, termed TA-DR5, in the same heavy chain format as in TA-HER2. TA-DR5 triggered apoptosis at ~100-fold lower concentration than the parental divalent anti-DR5 IgG monoclonal antibody.

Rossi et al. (Cancer Res., 68:8384-8392, 2008) reported the construction of a hexavalent anti-CD20 IgG antibody, designated Hex-hA20, using the Dock-and-Lock method. To generate Hex-hA20, which was composed of six Fab and two Fc regions, two components were constructed and separately produced in mammalian cells. First, the anchoring domain of the A-kinase anchoring proteins (AD) was genetically fused to the carboxyl terminus of the heavy chain in the humanized anti-CD20 IgG1 antibody, hA20. This construct was designated CH3-AD2-IgG-hA20. Second, the docking domain of the cyclic AMP-dependent protein kinase (DDD) was genetically fused to the carboxyl terminus of the Fab fragment of h20. This construct was designated CH1-DDD2-Fab-hA20. CH3-AD2-IgG-hA20 and CH1-DDD2-Fab-hA20 were purified by Protein A and Protein L affinity chromatography, respectively. Hex-hA20 was obtained by mixing purified CH3-AD2-IgG-hA20 and CH1-DDD2-Fab-hA20 under redox conditions followed by purification with Protein A. Hex-h20 inhibited proliferation of CD20-expressing B lymphoma cells lines without the need for a cross-linking antibody. Hex-h20 retained the ADCC activity of hA20, but lost the CDC activity.

Yoo et al. (J. Biol. Chem., 47:33771-33777, 1999) constructed variant human anti-DNS IgG2 antibodies in which part of the gamma-2 heavy chain was replaced with the corresponding part of the human alpha-1 heavy chain. In the construct termed γγγ-αtp, the 18-amino acid polypeptide present in the C-terminus of the human alpha-1 heavy chain, termed αtp (also called alpha tailpiece), was attached at the C-terminus of the human gamma-2 heavy chain. The γγγ-αtp construct was further modified to generate the following three variant IgG2 antibodies. In αγγ-αtp, the CH1 region of the gamma-2 heavy chain was replaced with the counterpart of the human alpha-1 heavy chain. In ααγ-αtp, the CH1, hinge and CH2 regions were replaced with the counterparts of the human alpha-1 heavy chain. In γαγ-αtp, the hinge and CH2 regions were replaced with the counterparts of the human alpha-1 heavy chain. These constructs were stably expressed in the mouse myeloma cell line Sp2/0 producing J chains. Each of purified γγγ-αtp, αγγ-αtp, ααγ-αtp and γαγ-αtp antibodies was a mixture of monomers, dimers, trimers, tetramers, pentamers and hexamers. The combined percentage of hexamers and pentamers in the mixture was 20% for γγγ-αtp, 25% for αγγ-αtp, 45% for ααγ-αtp, and 32% for γαγ-αtp.

Sorensen et al. (J. Immunol. 156:2858-2865, 1996) generated multivalent antibodies based on a human monoclonal anti-NIP (3-nitro-4-hydroxy-5-iodophenulacetic acid) IgG3 antibody variant in which the first, second and third hinge region are deleted. The gamma-3 heavy chain gene of this variant IgG3 antibody was modified in two locations. First, the 18-amino acid polypeptide present in the C-terminus of the human μ heavy chain, termed μtp (also called mu tailpiece), was attached at the C-terminus of the heavy chain. Second, a leucine residue at position 309 in the CH2 region was changed to a cysteine residue. Such modified monoclonal IgG3 antibody, called IgGL309Cμtp, was expressed in the mouse myeloma cell line J558L producing J chains, and purified using an NIP-Sepharose column. The secretion level was reported to be poorer for IgGL309Cμtp than for the parental IgG3 antibody, and a large fraction of IgGL309Cμtp was retained intracellularly. The size analysis showed that pentamers and hexamers constituted 81% of purified IgGL309Cμtp.

Sorensen et al. (Int. Immunol., 12:19-27, 2000) also modified the same human anti-NIP IgG3 antibody variant as described above by substituting the CH2 and CH3 regions of the gamma-3 heavy chain with the CH3 and CH4 regions, including μtp, of the human μ heavy chain. The heavy chain of such modified IgG3/IgM hybrid molecules, termed IgG-Cμ3-Cμ4, is composed of, from the N-terminus, the anti-NIP VH region, the CH1 and fourth hinge region of the human gamma-3 heavy chain, and the CH3 and CH4 regions, including μtp, of the human μ heavy chain. IgG-Cμ3-Cμ4 was expressed in J558L cells producing J chains and purified using an NIP-Sepharose column. Hexamers and pentamers constituted 14.0% and 66.7%, respectively, in purified IgG-Cμ3-Cμ4. Since IgG-Cμ3-Cμ4 does not have the CH2 and CH3 regions of the human gamma-3 heavy chain, it will lack Fcγ-mediated properties such as ADCC, pH-dependent FcRn binding, and the ability to bind to Protein A and Protein G.

SUMMARY OF THE CLAIMED INVENTION

The invention provides an antibody or fusion protein comprising an immunoglobulin heavy chain constant region, comprising in order from N- to C-terminus CH2 and CH3 regions, each of which is of IgG or IgA isotype, and Cμ3 and Cμ4 regions. Optionally, the immunoglobulin heavy chain further comprises a hinge region N-terminal to the CH2 region. Optionally, the immunoglobulin heavy chain further comprises a CH1 region N-terminal to the hinge region.

Optionally, the antibody or fusion protein is an antibody, wherein the heavy chain constant region is fused to a heavy chain variable region and the antibody further comprises a light chain comprising a light chain variable region and constant region. Optionally, the antibody is a component of a multi-specific antibody comprising a plurality of antibodies with different heavy chain variable regions, and optionally different light chain variable regions; the plurality of antibodies being complexed in the multi-specific antibody via the Cμ3 and Cμ4 regions.

Optionally, in an antibody or fusion protein mentioned above, the CH1 region, and hinge region, if present, and the CH2 and CH3 regions in an antibody or fusion protein of the invention are IgG1 regions. Optionally, the CH1 region and hinge region, if present, and the CH2 and CH3 regions in an antibody or fusion protein are IgG2 regions. Optionally, the CH1 region and hinge region, if present, and the CH2 and CH3 regions in an antibody or fusion protein are IgG3 regions. Optionally, the CH1 region and hinge region, if present, and the CH2 and CH3 regions in an antibody or fusion protein are IgG4 regions. Optionally, the CH1 region if present, and the CH2 and CH3 regions are IgA regions.

Optionally, the CH1 region, and the hinge region, if present, and the CH2 and CH3 regions are human CH1, hinge, CH2 and CH3 regions and the Cμ3 and Cμ4 regions are human Cμ3 and Cμ4 regions.

Optionally, the antibody or fusion protein is a single-chain antibody comprising a single-chain Fv linked to the heavy chain constant region. Optionally, the single-chain antibody is a component of a multi-specific antibody comprising a plurality of single-chain antibodies, wherein the scFvs of the plurality have different VH regions, and the plurality of single-chain antibodies are complexed in the multi-specific antibody via the Cμ3 and Cμ4 regions. Optionally, the scFvs have the same VL region.

Optionally, an antibody or fusion protein is in the form of a multimer comprising at least five or six copies of a unit comprising two of the heavy chains and two of the light chains, the copies being complexed in the multimer via the Cμ3 and Cμ4 regions.

Optionally, in an antibody or fusion protein as mentioned above, the CH1 region, if present, the hinge region and CH2 and CH3 regions are IgG and the antibody or fusion protein shows pH-dependent FcRn binding, specifically binds protein G, specifically binds protein A, exhibits ADCC, CDC and/or opsonization.

Optionally, in an antibody or fusion protein as mentioned above, the CH1 region, if present, and the hinge region, and CH2 and CH3 are human IgG1 regions and the antibody shows pH-dependent FcRn binding, specifically binds protein G, and specifically binds protein A. Optionally, such an antibody or fusion protein exhibits ADCC, CDC and opsonizaton.

Optionally, in an antibody or fusion protein as mentioned above, the CH1 region if present, and the hinge, CH2 and CH3 regions are human IgG2 or IgG4 regions and the antibody or fusion protein shows pH-dependent FcRn binding, specifically binds protein G and specifically binds protein A.

Optionally, in an antibody or fusion protein as mentioned above, the CH1 region if present, and the hinge region, and CH2 and CH3 regions are human IgG3 and the antibody shows pH-dependent FcRn binding, and specifically binds protein G. Optionally, the antibody or fusion protein of claim 20 that exhibits ADCC, CDC and opsonization.

Optionally, in an antibody or fusion protein as mentioned above, the CH1 region if present, and the CH2 and CH3 regions are human IgA and the antibody binds an Fc alpha receptor.

Optionally, an antibody or fusion protein as mentioned above is a fusion protein comprising the immunoglobulin heavy chain linked to a heterologous polypeptide. Optionally, the heterologous protein is linked to the hinge of the constant region via a flexible linker, such as Gly-Gly-Ala-Ala. Optionally, the heterologous polypeptide is a receptor extracellular domain or a polypeptide that specifically binds to a receptor extracellular domain. Optionally, the fusion protein is a component of a multi-specific complex comprising a plurality of fusion protein, the fusion proteins including different heterologous polypeptides.

Optionally, an antibody or fusion protein as mentioned above is a multispecific complex comprising an antibody and a fusion protein complexed via the Cμ3 and Cμ4 regions.

Optionally, an antibody or fusion protein as mentioned above is a humanized, chimeric, veneered or human antibody.

Optionally, an antibody or fusion protein as mentioned above specifically bind the extracellular domain of a receptor.

Optionally, an antibody or fusion protein as mentioned above specifically binds to CD79a, CD30, or DR5.

Optionally, an antibody or fusion protein as mentioned above is a fusion protein comprising an extracellular domain of a TNF-alpha receptor, LFA-3 or an IL-1 receptor, or is a fusion protein comprising a TRAIL protein.

Optionally, an antibody or fusion protein as mentioned above is conjugated to a toxic moiety, optionally, a cytotoxic moiety.

The invention further provides a pharmaceutical composition comprising an antibody or fusion protein as mentioned above.

The invention further provides a method of treating cancer comprising administering to a patient having or at risk of cancer an effective regime of an antibody or fusion protein as mentioned above.

The invention further provides a method of treating an immunological disorder comprising administering to a patient having or at risk of the disorder an effective regime of an antibody or fusion protein as mentioned above.

The invention further provides a method of producing a multi-specific complex of antibodies and/or fusion proteins, comprising a. transfecting a cell with a vector or vectors encoding a plurality of antibodies and/or fusion proteins as defined by claim 1, the antibodies and/or fusion proteins having different specificities; wherein the antibodies and/or fusion proteins are expressed and assembled into a multispecific complex via the Cμ3 and Cμ4 regions; and b. isolating the multi-specific complex from the cell culture. Optionally, each of the plurality of antibodies or fusion proteins is encoded by a different vector.

The invention further provides an antibody or fusion protein comprising a hybrid constant region comprising an N-terminal IgG constant region segment and a C-terminal IgM constant region segment; wherein the antibody exhibits pH dependent FcRn binding, specifically binds protein G, and multimerizes to form at least a pentamer or hexamer via the IgM constant region.

BRIEF DESCRIPTION OF THE DRAWING

FIGS. 3A-E: Elution pattern of anti-CD79a IgG1 antibodies from a Superose 6 gel filtration column.

FIG. 5: pH-dependent binding of multivalent IgG1 antibodies to FcRn.

FIGS. 12A-C: Elution pattern of the multivalent anti-CD79a IgG4 antibody from a Superose 6 gel filtration column.

FIGS. 13A-E: Elution pattern of anti-CD79a IgG3 antibodies from a Superose 6 gel filtration column.

FIG. 14: pH-dependent binding of multivalent IgG3 antibodies to FcRn.

FIGS. 15A-G: Binding of multivalent IgG3 antibodies to CD16.

FIGS. 16 A, B, C: Sequences of gamma-1 (SEQ ID NOs: 15-18), gamma-2 (SEQ ID NOs:19-22), gamma-3 (SEQ ID NOs:23-26), gamma-4 (SEQ ID NOs:27-30), alpha-1 (SEQ ID NOs:31-33), alpha-2 (SEQ ID NOs:34-36), mu heavy chain constant regions (SEQ ID NOs:51-54), and a J chain (SEQ ID NO:55). The 18 amino acid mu tailpiece is underlined in the Cmu sequence. The first 22 amino acids shown of the J chain are a cleaved signal peptide.

DEFINITIONS

Figure 1:
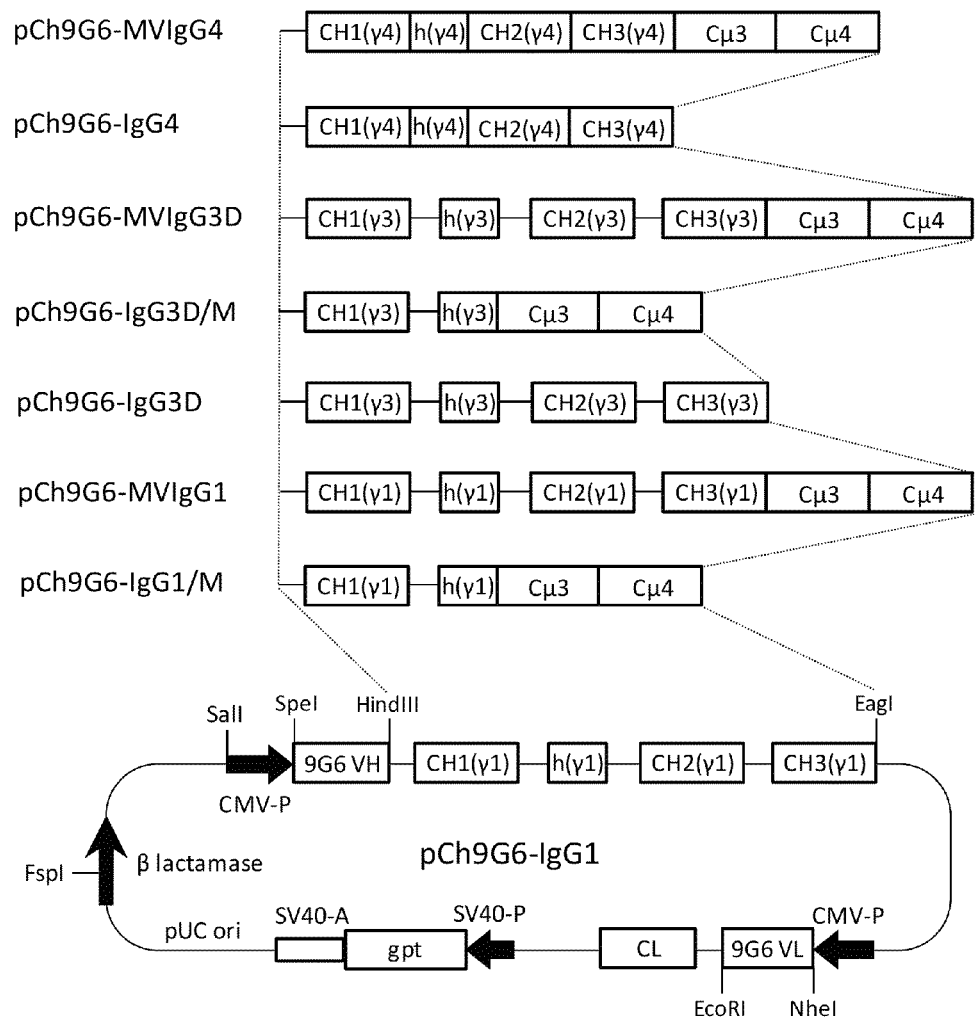
FIG. 1: Schematic structure of antibody expression vectors.

Antibodies or fusion proteins are typically provided in isolated form. This means that an antibody or fusion protein is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Sometimes antibodies or fusion proteins are at least 60, 70, 80, 90, 95 or 99% w/w pure of interfering proteins and contaminants from production or purification. Often an antibody or fusion protein is the predominant macromolecular species remaining after its purification.

Specific binding of an antibody or fusion protein to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody or fusion protein binds one and only one target.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the antibodies or fusion proteins of the invention have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. In IgA, the heavy constant region is divided into CH1, CH2 and CH3. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcRn binding. In IgM antibodies, the µ heavy chain constant region (Cµ) is subdivided into four regions Cµ1, Cµ2, Cµ3 and Cµ4. The Cµ3 and Cµ4 regions, sometimes in combination with one or more J chains, provide a multimerization function in natural IgM antibodies and antibodies or fusion proteins of the present invention. The mu tailpiece is a 18 amino-acid-long polypeptide located at the C-terminus of a IgM heavy chain constant region. IgM multimerizes to form a pentameric structure in the presence of J chains and a hexameric structure in their absence.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, bispecific antibodies can be made in which the two binding sites are different (see, e.g., Songsivilai and Lachmann, Clin. Exp. Immunol., 79:315-321 (1990); Kostelny et al., J. Immunol., 148:1547-53 (1992)). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chain variable regions or between different light chain variable regions are assigned the same number. Although Kabat numbering can be used for antibody constant regions, the EU index is more commonly used, as is the case in this application.

A multimerization unit is the monomeric unit of an antibody or fusion protein incorporating a hybrid constant region of the invention subject to multimerization by its IgM portion. A multimerization unit can itself be mono or divalent. In a mono-specific divalent antibody unit, the two heavy chains and two light chains are the same. In a bispecific divalent antibody unit, there are two different heavy and light chain pairings with different binding specificities. An antibody unit can also be monovalent containing a single heavy and light chain combination, as is the case with single-chain antibodies in which the heavy and light variable regions pair intramolecularly. A fusion protein unit can be monomeric, homodimeric containing two copies of a fusion protein or heterodimeric, containing two different fusion proteins.

Multimerization means the association of at least two multimerization units and more typically five or six such units via the Cμ portion of a hybrid constant region. Multimerization of antibodies or fusion proteins with a hybrid constant region may sometimes form higher or lower order structures than the pentameric or hexameric structure of normal IgM. Such is sometimes indicated by characterizing a complex formed by multimerization as having at least about five or six units.

Valency refers to the number of binding regions or in other words, maximum number of molecules of a target antigen that can be bound by an antibody or fusion protein. A normal homodimeric IgG antibody has a valency of two. A normal IgM antibody has a valency of 10 or 12 depending on whether a pentameric or hexameric structure is formed (i.e., five or six IgM units, each being a tetramer with two binding sites). Antibodies or fusion proteins of the present invention in which the monomeric unit is bivalent, can have valencies of 10 or 12, whereas antibodies or fusion proteins in which the monomeric unit is monovalent can have valencies of 5 or 6. The valencies may vary from these values in that antibody or fusion proteins with hybrid constant regions may sometimes form higher or lower order structures than the pentameric or hexameric structure of normal IgM. These valencies are theoretical maxima. In practice, the numbers of copies of an antigen bound may be less than the theoretical maximum due to steric constraints.

An antibody or fusion protein of the invention is mono-specific if all of its antigen (or ligand) binding regions have the same specificity. An antibody or fusion protein is multi-specific if its antigen binding regions include at least two different specificities. The number of different specificities in a multispecific antibody or fusion protein can range from 2 up to the maximum valency of the antibody or fusion protein (e.g., 10 or 12). In a population of antibodies or fusion proteins produced by the same cell culture, the number of different specificities can vary among different members of the population.

The term "antibody" includes any form of antibody with at least one binding region including monovalent fragments, divalent tetrameric units of two heavy chains and light chains, and higher order complexes, particularly pentamers and hexamers of monovalent or divalent units. An antibody can be mono-specific in which case all binding regions have the same specificity or multi-specific in which the binding sites have at least two specificities. Antibody fragments typically include a heavy chain variable region and hybrid heavy chain constant region and may also include a light chain variable region. For example, an antibody fragment can include from N-terminal to C-terminal a light chain variable region, a peptide spacer, a heavy chain variable region and a hybrid heavy chain constant region of the invention. Another fragment includes a heavy chain variable region (the binding region) and a hybrid heavy chain constant region and no light chain (i.e., a Dab or nanobody). Likewise, a fusion protein includes a monomeric or dimeric fusion protein unit, or higher order complexes, particularly pentamers and hexamers.

The term "epitope" refers to a site on an antigen to which an antibody or fusion protein binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. Some antibodies bind to an end-specific epitope, meaning an antibody binds preferentially to a polypeptide with a free end relative to the same polypeptide fused to another polypeptide resulting in loss of the free end. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

The term "antigen" or "target antigen" indicates a target molecule bound by an antibody or fusion protein. An antigen may be a protein of any length (natural, synthetic or recombinantly expressed), a nucleic acid or carbohydrate among other molecules. Antigens include receptors, ligands, counter receptors, and coat proteins.

A heterologous polypeptide in a fusion protein is a polypeptide not naturally linked to an immunoglobulin constant region. Such a polypeptide can be a full-length protein or any fragment thereof of sufficient length to retain specific binding to the antigen bound by the full-length protein. For example, a heterologous polypeptide can be a receptor extracellular domain or ligand thereto.

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγreceptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

The term opsonization also known as "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an immunoglobulin Fc region.

The term "complement-dependent cytotoxicity" or CDC refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

pH-dependent binding of an antibody to an FcRn receptor means that an antibody binds more strongly to such a receptor at pH 6.0 than at pH 7.5. Binding of FcRn at a low pH in endosomes after internalization by pinocytosis rescues IgG antibodies from catabolic degradation in lysosomes. Rescued IgG antibodies are then released from FcRn at a neutral pH and recycled to the circulation. Such pH-dependent FcRn binding is the basis of the molecular mechanism for a long serum half-life of IgG antibodies (and antibodies and fusion proteins incorporating hybrid constant regions of the invention) (Ghetie et al., Annu. Rev. Immunol. 18:739-766, 2000). For example, human IgG antibodies bind to human neonatal Fc receptors (FcRn) at pH 6.0 while they bind only weakly to FcRn at pH 7.5. The FcRn binding site in IgG antibodies lies at the junction of the CH2 and CH3 domains. Because a n heavy chain does not bind to FcRn at pH 6.0 or 7.5, natural IgM cannot take advantage of the FcRn-mediated pathway to rescue antibodies from degradation in lysosomes and therefore in general have shorter half-lives than natural IgG antibodies.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

A human antibody can be isolated from a human, or otherwise result from expression of human immunoglobulin genes (e.g., in a transgenic mouse, in vitro or by phage display). Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (1991) and phage display methods (see, e.g. Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332.

Protein A is a 40-60 kDa surface protein originally found in the cell wall of the bacterium *Staphylococcus aureus*. Protein A specifically binds with high affinity to human IgG1, IgG2 and IgG4 as well as mouse IgG2a and IgG2b. It does not bind to human IgG3 or IgA, or IgM. Protein A is used for affinity purification of antibodies.

Protein G is a 65-kDa (G148 protein G) and a 58 kDa (C40 protein G) Streptococcal cell surface protein. It contains a serum albumin binding domain not needed for IgG binding, which is often deleted. Protein G specifically binds to all of the human IgG isotypes but not IgA or IgM. Protein G is also useful for antibody purification.

DETAILED DESCRIPTION

I. General

Figure 17:
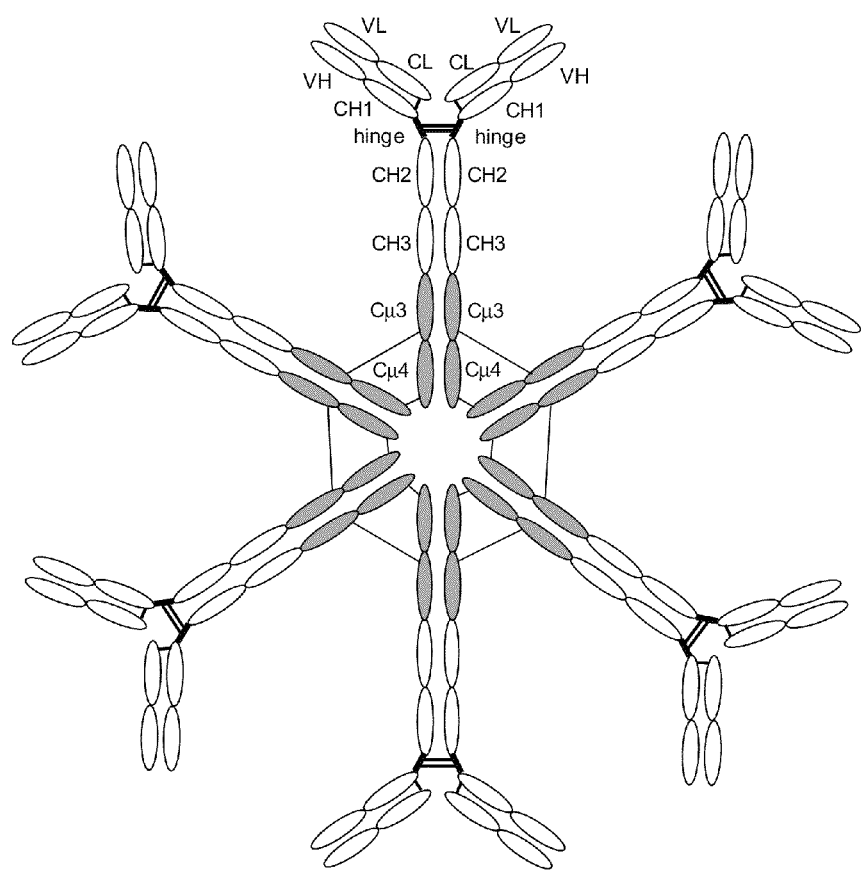
FIG. 17: An exemplary antibody with a hybrid constant region in hexameric conformation. Interchain disulfide bonds are shown by linear lines. Each monomeric unit has two binding sites, each formed from a heavy chain and a light chain variable region. Six monomeric units are bonded to one another via disulfide bonding between the Cµ3 and Cµ4 regions of different monomeric units. The antibody shown including the valency and disulfide bonding pattern are but one embodiment of the invention provided for illustration.

The invention provides hybrid constant regions and antibodies or fusion proteins incorporating the same. The hybrid constant regions include at least CH2 and CH3 regions of an IgG or IgA constant region and Cµ3 and Cµ4 regions of a Cµ constant region. The hybrids retain properties of both component constant regions. The hybrids retain the ability of a Cµ constant region to form multivalent complexes, e.g., pentameric or hexameric structures (as shown in FIG. 17). IgG hybrids also retain IgG properties including pH-dependent FcRn binding, which is associated with a relatively long in vivo half-life, and specifically binding to protein G, which facilitates purification. Depending on the isotype and subtype, the nature of the antigen and presence of additional IgG CH1 and hinge domains, IgG hybrids may also retain properties of specific binding to protein A, and effector functions ADCC, CDC and opsonization. IgA hybrids retain the property of IgA of binding to an Fc-alpha receptor CD89 (Swiss Prot P24071) in humans.

The combination of IgG effector functions, relatively long half-life and ease of purification with IgM's ability to multimerize results in antibodies or fusion protein with novel combinations of properties. For example, some such antibodies or fusion protein can effectively multimerize receptors or bound ligands on the cell surface while maintaining, or even enhancing, Fcγ-mediated properties such as ADCC, CDC, opsonization, pH-dependent FcRn binding, and the ability to bind to Protein A and Protein G relative to antibodies having an IgG isotype. The combination of properties from different isotypes offers the possibility of greater potency than conventional IgG, IgM or IgA antibodies for treatment of cancer and other diseases.

IgM's ability to multimerize also provides a format for making multi-specific complexes of antibodies and fusion proteins in which units with different specificities are held together by bonding between IgM constant regions.

The above advantages can be achieved without in vitro manipulations other than those involved in making nucleic acid constructs for expression of the hybrid antibodies or fusion proteins.

II Components of Hybrid Constant Regions

The hybrid constant regions include an IgG or IgA portion and a Cµ portion. The IgG or IgA portion includes at least IgG or IgA CH2 and CH3 regions. The CH2 and CH3 regions are responsible at least in part for FcRn binding, protein A and G binding, ADCC, CDC and opsonization. The IgG portion also preferably includes a hinge region and/or a CH1 region. The hinge region provides flexibility between the binding region and effector region of an antibody or fusion protein and contributes to efficient effector functions, such as ADCC, opsonization and CDC. The hinge region is also the site of disulfide bonds that link a pair of IgG heavy chains together. The CH1 region bonds with a light chain constant region and is generally included in formats in which a light chain with light chain constant region is present but can be omitted in fusion proteins or single-chain antibody formats in which no light chain constant region is present. IgA does not have a hinge region according to the Kabat delineation of regions. However, the residues in CH1 and CH2 flanking the border between these regions in IgA provide flexibility effectively serving the role of a hinge region. CH1 is preferably included in IgA fusions including an antibody light chain constant region and is preferably omitted otherwise.

The Cµ portion includes Cµ3 and Cµ4 of a Cµ constant region. The Cµ portion is responsible for multimerizing multiple monovalent or divalent binding units into a multivalent complex. Although understanding of mechanism is not required for practice of the invention, it is believed that multimerization of hybrid antibodies or fusion proteins occurs in similar fashion as in natural IgM antibodies through interchain disulfide bonding between the Cµ3 regions of different monomers and between the mu tailpieces of different monomers. Some multimers of IgM also contain one or more J chains bound to the mu tailpiece. In the presence of one or more J chains IgM can form a pentameric structure and in the absence of J chains can form a hexameric structure. Hexameric IgM has been reported to have stronger CDC than pentameric. Although antibodies and fusion proteins of the invention are believed to form pentameric or hexameric complexes as for IgM, other multiplicities greater or smaller may form as well or instead of pentameric and hexameric forms.

The components mentioned are above are arranged from N-terminus to C-terminus in the order: IgG or IgA CH1 region (if present), IgG hinge region (if present), IgG or IgA CH2 region, IgG or IgA CH3 region, Cµ3 region, and Cµ4 region.

Usually, all of the IgG or IgA regions are of the same isotype and subtype. That is, all IgG regions are either from IgG1, IgG2, IgG3 or IgG4, and all IgA regions are either from IgA1 or IgA2.

Preferably, the IgG or IgA regions are human IgG or IgA regions. Likewise, the Cµ3 and Cµ4 regions are preferably human. Exemplary sequences for human IgG1, IgG2, IgG3, IgG4, IgA1, IgA2, IgM heavy chain constant regions with delineation into components (CH1, hinge, CH2, CH3, Cµ1, Cµ2, Cµ3 and Cµ4 and a J-chain are shown in FIGS. 16 A, B, C. However, regions from other species including nonhuman primates, camelids, cartilaginous fish, mice or rats can also be used.

Reference to a human IgG, IgA or IgM region (i.e., CH1, hinge, CH2, CH3, Cµ3 and Cµ4) or J-chain refers to the exemplified sequences or allotypes or isoallotypes thereof or other variant sequence having at least 90, 95, 98 or 99% sequence identity with an exemplified sequence and/or differing from the exemplified sequence by up to 1, 2, 3, 4, 5, or 15 amino acid deletions, substitution or internal insertions in the case of CH1, CH2, CH3, Cµ3 and Cµ4 and a J-chain and 1, 2 or 3 deletions, substitutions or internal substitutions for IgG1, 2 or 4 hinge regions and up to 1, 2, 3, 4, 5, or 6 deletions for IgG3 hinge. Substitutions, if present, are preferably conservative. Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Reference to a human constant region includes a constant region with any natural allotype (including isoallotypes) or any permutation of residues occupying polymorphic positions in natural allotypes. Sequences of non-human constant regions are provided by e.g., the Swiss-Prot or Genbank databases. Reference to a non-human constant region likewise includes allotypic or isoallotypic variants, and permutations of the same, or other variants sequences differing from natural sequences. The scope of variations is defined by sequence identity and/or number of substitutions with respect to natural sequences of non-human constant regions in analogous fashion to the above description of variants with respect to human constant regions. The Eu numbering convention is used in defining corresponding positions among isotypes or different species, or defining mutated positions.

One or several amino acids at the amino or carboxy terminus of the light and/or heavy chain, such as a C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering) for increasing the half-life of an antibody. Substitution any of positions 234, 235, 236 and/or 237 reduce affinity for Fcγreceptors, particularly FcγRI receptor (see, e.g., U.S. Pat. No. 6,624,821). Optionally, positions 234, 236 and/or 237 in human IgG2 are substituted with alanine and position 235 with glutamine. (See, e.g., U.S. Pat. No. 5,624,821.)

If a hinge region is used, part of the hinge can be replaced by a synthetic linker molecule. Such is often the case in fusion proteins in which a binding region of the fusion protein is joined to CH2 and CH3 IgG or IgA constant regions via a hinge region in which, for example, up to 10 N-terminal residues are replaced by a synthetic flexible linker. Gly-Gly-Ala-Ala, Gly-Gly-Gly-Gly-Ser, Leu-Ala-Ala-Ala-Ala and multimers thereof are examples of such a linker. The hinge region can also be replaced in its entirety by a synthetic linker or omitted without replacement.

With the possible exception of a synthetic linker replacing part or all of a hinge region and one or a few amino acid substitutions to enhance or suppress effector functions or FcRn binding as discussed further below, and the attachment of a binding region at the N-terminus, it is preferred that hybrid constant regions contain no sequences other than the CH1, hinge, CH2, CH3, Cµ3 and Cµ4 regions mentioned above. Nevertheless, other sequences, such as for example, a hexa-histidine tag, can be added but are not necessary.

III. Properties of Fusions

The properties of an antibody or fusion protein incorporating a hybrid heavy chain constant region as described above depend in part on the isotype, and subtype of the CH1, hinge (if present), CH2 and CH3 regions, whether the CH1 and/or hinge regions are present, and the nature of the antigen bound by the antibody or fusion protein.

Antibodies and fusion proteins incorporating the hybrid constant regions retain at least the ability of Cµ3 and Cµ4 to multimerize a monovalent or divalent unit to higher valency and at least one property of IgG or IgA antibodies. When CH1, hinge (if present), CH2 and CH3 are of IgG origin, the antibodies retain at least the IgG-like properties of binding protein G and pH-dependent FcRn binding, as well as capacity to specifically bind to a target antigen.

Selection of isotype or subtype depends on the desired properties. As with non-hybrid antibodies, IgG1 or IgG3 is selected if strong effector functions are desired (as is often the case against cancer cells, pathogens) and IgG2 or IgG4 is selected if weaker or no CDC, ADCC and opsonization are required (as may be the case if the mechanism is inhibition of a receptor-ligand interaction).

When the CH1 and hinge regions (if present), CH2 and CH3 regions are human IgG1, then an antibody or fusion protein incorporating a hybrid constant region has pH-dependent FcRn binding, specific binding to protein A, and protein G, and may have effector functions, such as ADCC, CDC, opsonization depending on the antigen bound. Such effector functions are usually present if the antigen bound is a surface receptor (e.g., on a cell or virus). If the antigen is normally in soluble form, effector functions are not usually expressed against the soluble antigen but can be demonstrated by expressing the antigen in bound form (e.g., on a cell surface).

When the CH1 and hinge regions (if present), CH2 and CH3 regions are human IgG2, IgG4, then an antibody or fusion protein incorporating a hybrid heavy chain constant region shows at least pH-dependent FcRn binding and specific binding to protein A and protein G. Human IgG2 and IgG4 isotypes generally lack CDC. IgG4 has some ADCC and opsonization against bound antigens but less than human IgG1 or IgG3.

When the CH1 and hinge regions (if present), CH2 and CH3 regions are human IgG3, then an antibody or fusion protein incorporating a hybrid heavy chain constant region shows at least pH-dependent FcRn binding, and specific binding to protein G. Such an antibody or fusion protein may also show effector functions, such as ADCC, CDC, opsonization depending on whether the antigen bound is a surface antigen or soluble, as is the case for IgG1.

In antibodies or fusion proteins with hybrid constant regions in which CDC, ADCC or opsonization is present, the level of CDC, ADCC, or opsonization is sometimes the same as (within experimental error) or sometimes greater than that of an otherwise comparable antibody or fusion protein with a conventional IgG constant region.

IV. Antibody and Fusion Protein Formats

Hybrid constant regions can be incorporated into mono-specific antibodies, fusion proteins, and multi-specific complexes. For expression of a mono-specific antibody, a hybrid heavy chain constant region can be linked to a heavy chain variable region and expressed with a light chain comprising a variable region and constant region. The heavy and light chain bind to one another via the CH1 region of the heavy chain and light chain constant region to a form a heterodimer. Two heterodimers then pair by association of hinge, CH2 and CH3 regions of the IgG or IgA portion of the heavy chain to form a tetramer unit, as is the case for a conventional antibody. Tetramer units can further multimerize by association of the Cμ portion of the heavy chain constant regions of the units. The heavy chain constant regions can associate by disulfide bonding between Cμ3 regions of different chains and/or by disulfide bonding between the mu tailpieces of different chains.

For a mono-specific single-chain antibody, heavy and light chain variable regions are expressed as part of the same chain typically separated by a peptide spacer (see, e.g., U.S. Pat. No. 5,260,203, U.S. Pat. No. 5,869,203, U.S. Pat. No. 6,291, 159). The length of the peptide spacer determines whether heavy and light chain variable regions associate intramolecularly forming a unit containing one light chain variable region intramolecularly paired to one heavy chain variable region or intermolecularly forming a tetrameric unit of two light chain variable regions and two heavy chain variable regions, each light chain variable region intermolecularly bonded to a heavy chain variable region. In either case, the units can multimerize via the Cμ portion of a hybrid constant region linked to the heavy chain variable region. Multimerization via disulfide bonding of the Cμ portion can result in complexes containing at least about five or six units.

The hybrid constant regions can be used with any type of engineered antibody including chimeric, humanized, veneered or human antibodies. The antibody can be a monoclonal antibody or a genetically engineered polyclonal antibody preparation (see U.S. Pat. No. 6,986,986).

For fusion protein proteins, a hybrid constant region is expressed linked to a heterologous polypeptide. The heterologous polypeptide provides a binding region at the N-terminus of the constant region and is sometimes referred to simply as a binding region. The IgG or IgA CH1 region is not typically included in the constant region for fusion proteins. The IgG hinge region may or may not be included. In some fusion proteins, part or all of the hinge region is replaced by a synthetic linker peptide conferring flexibility between the binding portion of a fusion protein and the hybrid constant region.

The binding region of a fusion protein can be any of the types of binding portion used in other fusion proteins produced to date (among others). Examples of binding regions are extracellular domains of cellular receptors or their ligands or counter-receptors (e.g., TNF-alpha receptor, LFA3 or IL-1 receptor or Trail).

Both antibody and fusion proteins can be expressed in a multi-specific format, that is, as a complex containing antibody or fusion protein units within different target specificities. Individual specificities associate via multimerization of the Cμ portion of the constant region. The number of different specificities within a complex can be, for example, 2, 3, 4, 5, 6, 7, 8, 9, 10, 11 or 12. Combinations of units of different specificities can occur at two levels. In the first level, a divalent multimerization unit can contain two binding specificities as in a bispecific antibody or a heterodimeric fusion protein. In the second level of combination, multimerization units of different specificities can combine with one another via Cμ-mediated multimerization. Such multimerization generates complexes of at least about five or six units.

When the two levels of combining specificities are aggregated, the present methods allow combining at least about 10 (pentamers) or 12 (hexamers) specificities in the same complex. Although in many applications, this number of specificities may be more than needed, the present methods offer an advantage in applications where fewer specificities are needed (e.g., only 2). Because of the second level at which specificities are combined, it become statistically much more likely that any complex formed includes at least one unit of each desired specificity. By contrast, when expressing a bispecific antibody by conventional methods, formation of multi-specific units may compete with formation of mono-specific units leading to a heterogeneous population of antibodies, some of which are bispecific but of which a substantial number are mono-specific.

In multi-specific formats of antibodies, the units typically contain different heavy chain variable regions. The light chain variable regions can also be different. However, it is also possible to select (e.g., using phage display) antibodies of different binding specificities having the same light chain variable region. Such antibodies can be combined in a multispecific format in which the units have different heavy chain variable regions but the same light chain variable region.

A multi-specific antibody or fusion protein can include binding specificities for an antigen on a target (e.g., a cancer cell or pathogen) and for an antigen on an effector cell (e.g., CD3 on a T-cell). Such a multi-specific complex forms a bridge between the target cell and effector cell and promotes cytotoxic or opsonization activity of the effector cell. A multi-specific antibody or fusion protein can additionally or alternatively include binding specificities for two different antigens on the same target (e.g., a cancer cell or pathogen). Such an antibody or fusion protein can have greater selective toxicity to the target cell than an antibody or fusion protein with specificity for a single antigen. Other multi-specific antibodies or fusion proteins include binding regions for both a receptor and its ligand or counter-receptor. Such antibodies or fusion proteins can exert greater inhibition than antibodies or fusion proteins binding receptor or ligand/counterreceptor alone. Any of these specificities and others can be combined in the same multi-specific complex.

V. Genetic Engineering and Expression

Antibodies or fusion proteins including a hybrid heavy chain constant chain are produced by recombinant expression. A hybrid constant region is achieved by fusing a DNA segment encoding the IgG or IgA portion in-frame with a DNA segment encoding the Cμ portion. Preferably, the last amino acid of a CH3 exon of the IgG or IgA portion is fused in frame to the first amino acid of a Cμ3 exon. The N-terminus of the segment encoding the hybrid constant region can be fused to a DNA segment encoding a binding region, which can be a heavy chain variable region in the case of an antibody or other binding region (e.g., an extracellular region of a cell surface receptor) in the case of fusion protein. In a single-chain antibody, a DNA construct encoding at least the light chain variable region can be fused in frame with the segment encoding the heavy chain. Alternatively, the light chain can be expressed separately, either as a different expression unit on the same vector as the heavy chain or on a separate vector. As in conventional antibody production, DNA segments encoding an antibody chain or fusion protein are typically operably linked at the N-terminus to a DNA segment encoding a signal peptide to allow secretion.

The order in which fusions of genetic elements is performed in building a construct encoding several components is not important. For example, a DNA segment encoding a heavy chain variable region can be linked to DNA encoding an IgG portion of a hybrid constant region, which can in turn linked to DNA encoding an IgM portion, or the segments encoding a hybrid constant region can be linked to one another first. The segments can also be linked simultaneously by joining overlapping oligonucleotides encoding the respective segments in an overlapping PCR-type reaction. In practice, once an expression vector encoding a hybrid constant region has been produced, the same vector can be used to insert any heavy chain variable region or other binding region in the case of a fusion protein (and sometimes a light chain variable region) without recreating the DNA segment encoding the hybrid constant region.

Mammalian cells are a preferred host for expressing nucleotide segments encoding antibodies or fusion proteins of the invention (see Winnacker, From Genes to Clones, (VCH Publishers, NY, 1987)). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. The cells used for producing antibodies may or may not endogenously express J chains. If endogenous J chains are not expressed or are expressed at an insufficient level, host cells can be genetically modified to express J chains (i.e., by introducing a construct encoding such). However, host cells not expressing J chains can also be used. Selection of cells with or without J chains affects valency with which antibodies or fusion proteins are produced (e.g., pentamer with J chains and hexamer without). Preferably, an antibody or fusion protein of the invention is expressed from a monoclonal cell line.

Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Cells are transfected with one or more vectors encoding the antibody or fusion protein to be expressed. For a multi-chain antibody, the heavy and light chains can be expressed on the same or separate vectors. For expression of multi-specific complexes, the DNA encoding the components of the complexes (i.e., different antibodies or fusion proteins) can be on the same or different vectors.

Antibody or fusion protein chains are expressed, processed to remove signal peptides, assembled and secreted from host cells. It is believed that multimerization and association with J chains occur at least predominantly within cells so that antibodies or fusion proteins are secreted primarily as multimers, particularly multimers in which five or six units are associated via the Cµ portion of the hybrid constant region.

Antibodies or fusion proteins can be purified from cell culture supernatants by conventional antibody purification methods. If the hybrid constant region includes an IgG portion, then the purification can include a chromatography step using protein A or protein G as the affinity reagent. If the hybrid constant region includes an IgA portion, Jacalin lectin affinity chromatography can be used instead. Conventional antibody purification procedures, such as ion exchange, hydroxyapatite chromatograph or HPLC can also be used (see generally, Scopes, Protein Purification (Springer-Verlag, NY, 1982)).

VI. Targets

Antibodies or fusion proteins incorporating a hybrid constant region can be made to any target molecule. The antibodies or fusion proteins are particularly useful for surface-bound target proteins (e.g., on cells or viruses) in which aggregation of the target protein induces a desired response. The desired response can be, for example, clearing of a cell or virus bearing a target, signal transduction through a receptor, e.g., inducing apoptosis, inhibiting a receptor binding to a ligand or counterreceptor, or internalization of an antibody or fusion protein conjugated to a toxic agent. Antibodies or fusion proteins can be made to the same targets as existing commercial antibodies or fusion proteins or can be derivatized versions of commercial antibodies or fusion proteins in which the existing constant region has been replaced by a hybrid constant region of the present invention. The antibodies or fusion proteins can also aggregate surface-bound antigen indirectly by binding to a target ligand bound to a surface-bound antigen.

To illustrate one possible mechanism of action, an antibody or fusion protein incorporating a hybrid heavy chain constant region of the invention is generated with specificity to a member of the tumor necrosis factor receptor super-family. Such receptors require trimerization for signal transduction. Because the antibody is multivalent (e.g., a pentamer or hexamer) it can multimerize antigens on the surface of tumor cells and induce apoptosis and/or growth arrest of tumor cells. Efficacy of such multivalent antibodies to treat cancer can be studied in mouse xenograft models or other appropriate animal models of cancer.

To illustrate another mechanism, an antibody or fusion protein incorporating a hybrid heavy chain constant region is generated with specificity to an antigen expressed on the surface of immune cells, for example, B cells, T cells, monocytes, neutrophils or dendritic cells. Such an antibody can multimerize the antigen on the surface of immune cells and trigger normal or abnormal signal transduction. Alternatively, such an antibody can trigger internalization of the cell surface antigen. The function of such immune cells is enhanced or suppressed, depending on the antigen, type of cells and epitope bound, resulting in modulation of the immune system. The efficacy of such an antibody to treat immune disorders is studied in appropriate in vitro systems or animal models of an immune disorder.

To illustrate another mechanism, an antibody or fusion protein incorporating a hybrid heavy chain constant region is generated with specificity to an antigen expressed by a pathogen, such as infectious bacteria, yeast, fungus or virus. The antibody neutralizes the infectious microorganism or virus (e.g., by ADCC, CDC, opsonization, or by inhibiting interaction between the pathogen and a cellular receptor, or by action of a toxic moiety attached to the antibody.) The efficacy of such an antibody to treat infectious diseases can be studied in appropriate in vitro systems or animal models of infection.

Targets of interest include receptors on cancer cells and their ligands or counter-receptors (e.g., CD3, CD20, CD22, CD30, CD34, CD40, CD44, CD52 CD70, CD79a, DR4 DR5, EGFR, CA-125/Muc-16, MC1 receptor, PEM antigen, gp72, EpCAM, Her-2, VEGF or VEGFR, ganglioside GD3, CEA, AFP, CTLA-4, alpha v beta 3, HLA-DR 10 beta, SK-1). Other targets of interest are autoantibodies or T-cell subsets mediating autoimmune disease. Other targets of interest are growth factor receptors (e.g., FGFR, HGFR, PDGFR, EFGR, NGFR, and VEGFR) and their ligands. Other targets are G-protein receptors and include substance K receptor, the angiotensin receptor, the α and β adrenergic receptors, the serotonin receptors, and PAF receptor. See, e.g., Gilman, Ann. Rev. Biochem. 56:625 649 (1987). Other targets include ion channels (e.g., calcium, sodium, potassium channels), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are adhesion proteins such as integrins, selectins, and immunoglobulin superfamily members (see Springer, Nature 346:425 433 (1990). Osborn, Cell 62:3 (1990); Hynes, Cell 69:11 (1992)). Other targets are cytokines, such as interleukins IL-1 through about IL-37 to-date, tumor necrosis factors, interferon, and, tumor growth factor beta, colony stimulating factor (CSF) and granulocyte monocyte colony stimulating factor (GM-CSF). See Human Cytokines: Handbook for Basic & Clinical Research (Aggrawal et al. eds., Blackwell Scientific, Boston, Mass. 1991). Other targets are amyloidogenic peptides, such as Abeta, alpha-synuclein or prion peptide. Other targets are hormones, enzymes, and intracellular and intercellular messengers, such as, adenyl cyclase, guanyl cyclase, and phospholipase C. Target molecules can be human, mammalian or bacterial. Other targets are antigens, such as proteins, glycoproteins and carbohydrates from microbial pathogens, both viral and bacterial, and tumors.

Some examples of commercial antibodies and their targets include alemtuzumab, CD52, rituximab, CD20, trastuzumab Her/neu, nimotuzumab, cetuximab, EGFR, bevacizumab, VEGF, palivizumab, RSV, abciximab, GpIIb/IIIa, infliximab, adalimumab, certolizumab, golimumab TNF-alpha, bacilixamab, daclizumab, IL-2, omalizumab, IgE, gemtuzumab, CD33, natalizumab, VLA-4, vedolizumab alpha4beta7, belimumab, BAFF, otelixizumab, teplizumab CD3, ofatumumab, ocrelizumab CD20, epratuzumab CD22, alemtuzumumab CD52, eculizumab C5, canakimumab IL-1beta, mepolizumab IL-5, reslizumab, tocilizumab IL-6R, ustekinumab, briakinumab IL-12, 23. Examples of commercial fusion proteins include etanercept which binds TNF-alpha, alefacept (LFA3-Fc fusion which binds CD2), TACI-Fc fusion which binds BAFF and APRIL, abatacept (CTLA-4-Fc which binds CD80 and CD86), and romiplostim (a peptide analog of thrombopoietin fused to Fc). Any of the commercial antibodies or fusion protein can be modified to replace the existing heavy chain constant region with a hybrid constant region of the invention. Alternatively, a hybrid constant region can be linked to other antibodies with the same target specificity (e.g., as determined by a competition assay) as any of the above commercial antibodies or fusion proteins.

VII. Immunoconjugates

Antibodies or fusion proteins can be conjugated to a toxic agent. Toxic agents can be cytotoxic or cystostatic. Some example of toxic agents include antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, camptothecins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like. A variety of radionuclides are available for the production of radioconjugated antibodies. Examples include $^{212}$Bi, $^{131}$I, $^{131}$In, $^{90}$Y, and $^{186}$Re. Conjugates of an antibody and toxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). A toxic agent can also be linked to an antibody via a linker, which may be cleavable under intracellular conditions 9US 2003-0083263, 2005-0238649 and 2005-0009751). Many of the above toxic agents are only effective or most effective when internalized within a cell. The antibodies or fusion proteins of the invention can be internalized by binding to cellular receptors, for example, crosslinking of cellular receptors can promote internalization.

VIII. Methods of Treatment and Pharmaceutical Compositions

The antibodies or fusion proteins of the invention can be used for treating cancers including those for which commercial antibodies mentioned above have been used. The methods can be used to treat solid tumors, and particularly hematological malignancies, such as leukemia (e.g., T cell large granular lymphocyte leukemia), lymphoma (Hodgkin's or Non-Hodgkin's), or multiple myeloma. Solid tumors include skin (e.g., melanoma), ovarian, endometrial, bladder, breast, rectum, colon, gastric, pancreatic, lung, thymus, kidney and brain.

The antibodies and fusion protein of the invention can also be used for suppressing various undesirable immune responses including those in which the commercial antibodies mentioned above have been used.

One category of immune disorders treatable by antibodies or fusion proteins of the invention is transplant rejection. When allogeneic cells or organs (e.g., skin, kidney, liver, heart, lung, pancreas and bone marrow) are transplanted into a host (i.e., the donor and donee are different individual from the same species), the host immune system is likely to mount an immune response to foreign antigens in the transplant (host-versus-graft disease) leading to destruction of the transplanted tissue. The antibodies of the present invention are useful, inter alia, to block alloantigen-induced immune responses in the donee.

A related use for antibodies or fusion proteins of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants.

A further situation in which immune suppression is desirable is in treatment of autoimmune diseases such as type 1 diabetes, Crohn's disease, ulcerative colitis, µltiple sclerosis, stiff man syndrome, rheumatoid arthritis, myasthenia gravis and lupus erythematosus. In these diseases, the body develops a cellular and/or humoral immune response against one of its own antigens leading to destruction of that antigen, and potentially crippling and/or fatal consequences. Autoimmune diseases are treated by administering one of the antibodies or fusion proteins of the invention.

Other immune disorders treatable by antibodies or fusion proteins of the invention, include asthma, allergies, celiac disease, psoriasis, and uveitis. Celiac disease, psoriasis and uveitis are autoimmune diseases.

The antibodies or fusion protein can also be used for treatment of pathogenic infections, such as viral, bacterial, protozoan or fungal infection. Some example of viral infections include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus. Some examples of bacterial infections include *chlamydia, rickettsial* bacteria, *mycobacteria, staphylococci, streptococci, pneumonococci, meningococci* and *conococci, klebsiella, proteus, serratia, pseudomonas, legionella, diphtheria, salmonella, bacilli, cholera, tetanus, botulism, anthrax, plague, leptospirosis,* Lymes disease bacteria, *streptococci,* or *neisseria.* Some examples of pathogenic fungi include *Candida, Aspergillus, Cryptococcus, Histoplasma, Pneumocystis* and *Stachybotrys.* Examples of protozoa include *Cryptosporidium, Giardia lamblia* and *plasmodium.*

Antibodies or fusion proteins are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody or fusion protein are 0.01-20, or 0.5-5, or 0.01-1, or 0.01-0.5 or 0.05-0.5 mg/kg body weight (e.g., 0.1, 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the antibody or fusion protein in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Treatment with antibodies of the invention can be combined with other treatments effective against the disorder being treated. For treatment of immune disorders, conventional treatments include mast cell degranulation inhibitors, corticosteroids, nonsteroidal anti-inflammatory drugs, and stronger anti-inflammatory drugs such as azathioprine, cyclophosphamide, leukeran, FK506 and cyclosporine. Biologic anti-inflammatory agents, such as Tysabri® (natalizumab) or Humira® (adalimumab), can also be used. When used in treating cancer, the antibodies of the invention can be combined with chemotherapy, radiation, stem cell treatment, surgery or treatment with other biologics such as Herceptin® (trastuzumab) against the HER2 antigen, Avastin® (bevacizumab) against VEGF, or antibodies to the EGF receptor, such as (Erbitux®, cetuximab), and Vectibix® (panitumumab). Chemotherapy agents include chlorambucil, cyclophosphamide or melphalan, carboplatinum, daunorubicin, doxorubicin, idarubicin, and mitoxantrone, methotrexate, fludarabine, and cytarabine, etoposide or topotecan, vincristine and vinblastine. For infections, treatment can be in combination with antibiotics, anti-virals, anti-fungal or anti-protozoan agents or the like.

IX. Other Applications

The antibodies or fusion proteins can be used for detecting their target molecule in the context of clinical diagnosis or treatment or in research. For example, the antibodies can be used to detect a cancer-related antigen as an indication a patient is suffering from an immune mediated disorder amenable to treatment. The antibodies can also be sold as research reagents for laboratory research in detecting targets and their response to various stimuli. In such uses, antibodies or fusion proteins can be labeled with fluorescent molecules, spin-labeled molecules, enzymes or radioisotypes, and can be provided in the form of kit with all the necessary reagents to perform the assay. The antibodies or fusion protein can also be used to purify their target antigens e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1

Expression Vectors

Gene cloning, mutagenesis and plasmid construction in this work was carried out with standard molecular biology techniques. See Sambrook and Russel (Molecular Cloning, A Laboratory Manual, 3rd ed., 2001, Cold Spring Harbor Laboratory Press, Cold Spring Harbor, N.Y.), Kostelny et al. (Int. J. Cancer 93:556-565, 2001), and Cole et al. (J. Immunol. 159: 3613-3621, 1997), which are incorporated herein by references.

The mammalian expression vector pCh9G6-IgG1 (FIG. 1) for production of a chimeric IgG1 form of the mouse anti-human CD79a monoclonal antibody 9G6 (Ch9G6-IgG1) was constructed to contain the following genetic components. Proceeding clockwise from the SalI site of pCh9G6-IgG1 in FIG. 1, the plasmid contains the heavy chain transcription unit starting with the human cytomegalovirus (CMV) major immediate early promoter and enhancer (CMV-P in the figure) to initiate transcription of the antibody heavy chain gene. The CMV promoter is followed by the heavy chain variable region exon of the mouse anti-human CD79a monoclonal antibody 9G6 (9G6 VH) flanked by the SpeI and HindIII sites, a genomic sequence containing the human γ-1 heavy chain constant regions including the CH1 (CH1(γ1)), hinge (h(γ1)), CH2 (CH2(γ1)) and CH3 (CH3(γ1)) exons with the intervening introns, and the polyadenylation site of the human γ-1 heavy chain gene. After the heavy chain gene sequence, the light chain transcription unit begins with the CMV promoter (CMV-P), followed by the light chain variable region exon of the mouse anti-human CD79a monoclonal antibody 9G6 (9G6 VL) flanked by the NheI and EcoRI sites, a genomic sequence containing the human kappa chain constant region exon (CL) with part of the intron preceding it, and the polyadenylation site of the human kappa chain gene following the CL exon. The light chain gene is then followed by the SV40 early promoter (SV40-P), the E. coli xanthine guanine phosphoribosyl transferase gene (gpt), and a segment containing the SV40 polyadenylation site (SV40-A). Finally, the plasmid contains a part of the plasmid pUC19, comprising the bacterial origin of replication (pUC ori) and the β lactamase gene (β lactamase). Arrows in the figure indicate the orientation of transcription.

The mouse hybridoma producing anti-human CD79a monoclonal IgG antibody 9G6 was created at JN Biosciences (Mountain View, Calif.) using recombinant human CD79a proteins as immunogens and following standard hybridoma techniques. The VH and VL sequences were determined by standard experimental procedures such as the method described by Tsurushita et al. (Methods 36:69-83, 2005). The 9G6 VH gene in the SpeI-HindIII fragment was designed as an exon including a splice donor signal at the 3' end of the coding region. The amino acid sequence of 9G6 VH, including the signal peptide, encoded by the VH exon in pCh9G6-IgG1 is shown below. The mature 9G6 VH sequence starts at position 20 in SEQ ID NO:1.

```
Amino acid sequence of 9G6 VH (SEQ ID NO: 1):
MGWSRIFLFLLSITAGVHCQVQLQQSGPELVKPGASVKISCKASGYTFS

TSWMNWVKQRPGQGLEWIGRIYPGDGDTNYNGKFKGKATLTADKSSNTA

YMQLSSLTSVDSAVYFCERFYYGNTFAMDYWGQGTSVTVSS
```

The 9G6 VL gene in the NheI-EcoRI fragment was also designed as an exon including a splice donor signal at the 3' end of the coding region. The amino acid sequence of 9G6 VL, including the signal peptide, encoded by the VL exon in pCh9G6-IgG1 is shown below. The mature 9G6 VL sequence starts at position 20 in SEQ ID NO:2.

```
Amino acid sequence of 9G6 VL (SEQ ID NO: 2):
MKLPVRLLVLMFWIPASSSDVLMTQIPLSLPVSLGDQASISCRSSQSIV

HSNGNTYLEWYLQKPGQSPKLLIYKVSNRFSGVPDRFSGSGSGTDFTLK

ISRVEAEDLGVYYCFQGSHVPFTFGSGTKLEIKR
```

The amino acid sequence of the immunoglobulin heavy chain constant region encoded in pCh9G6-IgG1 is shown below.

```
Heavy chain constant region encoded in
pCh9G6-IgG1 (SEQ ID NO: 3):
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

The amino acid sequence of the immunoglobulin light chain constant region encoded in pCh9G6-IgG1 is shown below.

```
Light chain constant region encoded in pCh9G6-IgG1 (SEQ ID NO: 4):
TVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC
```

The expression vector pCh9G6-IgG1 was modified to construct a new expression vector pCh9G6-IgG1/M in such a way that a cDNA-derived fragment encoding the CH3 and CH4 regions of the human μ heavy chain (Cμ3 and Cμ4, respectively) was fused in frame to the last amino acid of the hinge region in pCh9G6-IgG1. The amino acid sequence of Cμ3 and Cμ4 is shown below.

Cμ3 and Cμ4 of the human μ heavy chain (SEQ ID NO: 5):
DQDTAIRVFAIPPSFASIFLTKSTKLTCLVTDLTTYDSVTISWTRQNGEAVKTHTNISES

HPNATFSAVGEASICEDDWNSGERFTCTVTHTDLPSPLKQTISRPKGVALHRPDVYLL

PPAREQLNLRESATITCLVTGFSPADVFVQWMQRGQPLSPEKYVTSAPMPEPQAPGR

YFAHSILTVSEEEWNTGETYTCVVAHEALPNRVTERTVDKSTGKPTLYNVSLVMSDT

AGTCY

The CH2 and CH3 exons of the human γ-1 heavy chain were deleted in pCh9G6-IgG1/M. The light chain sequence of pCh9G6-IgG1 was not modified in pCh9G6-IgG1/M. The schematic structure of pCh9G6-IgG1/M is shown in FIG. 1. The structure of the heavy chain constant region encoded in pCh9G6-IgG1/M includes from the N-terminus to the C-terminus, the CH1 and hinge regions of the human gamma-1 heavy chain, and the Cμ3 and Cμ4 regions. The amino acid sequence of the heavy chain constant region encoded in pCh9G6-IgG1/M is shown below.

Heavy chain constant region encoded in pCh9G6-IgG1/M (SEQ ID NO: 6):
ASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPDQ

DTAIRVFAIPPSFASIFLTKSTKLTCLVTDLTTYDSVTISWTRQNGEAVKTHTNISESHP

NATFSAVGEASICEDDWNSGERFTCTVTHTDLPSPLKQTISRPKGVALHRPDVYLLPP

AREQLNLRESATITCLVTGFSPADVFVQWMQRGQPLSPEKYVTSAPMPEPQAPGRYF

AHSILTVSEEEWNTGETYTCVVAHEALPNRVTERTVDKSTGKPTLYNVSLVMSDTA

GTCY

The expression vector pCh9G6-IgG1 was also modified in such a way that the coding region of Cμ3 and Cμ4 was fused in frame to the last amino acid of the CH3 exon in pCh9G6-IgG1. The light chain sequence was not modified. The schematic structure of the resulting plasmid, pCh9G6-MVIgG1, is shown in FIG. 1. The amino acid sequence of the heavy chain constant region encoded in pCh9G6-MVIgG1 is shown below.

Figure 2:
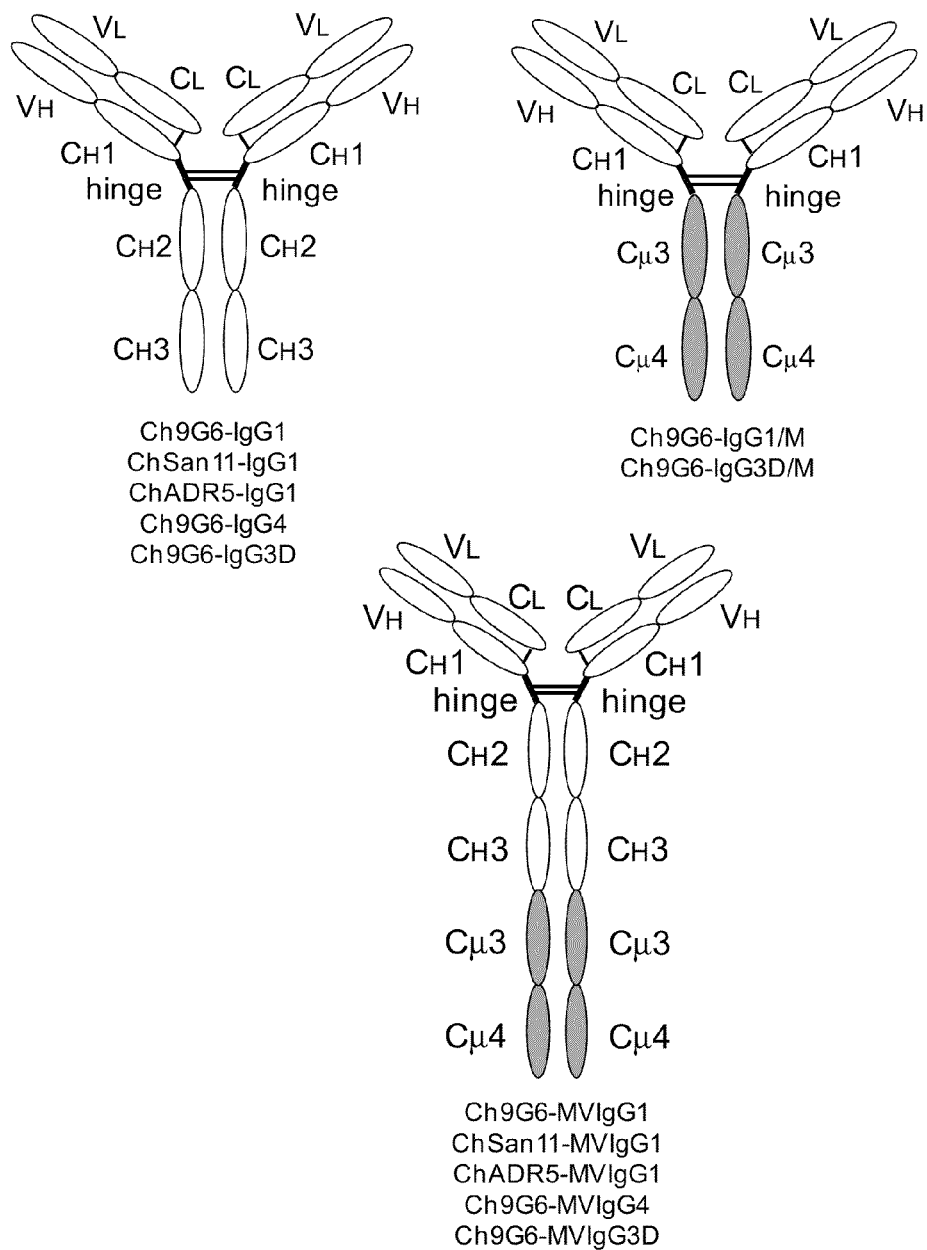
FIG. 2: Schematic structure of recombinant antibodies in the monomeric form.

The schematic structure of the monomer form of the antibodies produced from pCh9G6-IgG1, pCh9G6-IgG1/M and pCh9G6-MVIgG1 (Ch9G6-IgG1, Ch9G6-IgG1/M and Ch9G6-MVIgG1, respectively) is shown in FIG. 2. The symbols "CH1", "hinge", "CH2" and "CH3" in the figure denote the CH1, hinge, CH2 and CH3 regions of human gamma heavy chains, respectively. The symbols "Cμ3" and "Cμ4" denote the CH3 and CH4 regions of the human μ heavy chain, respectively. The symbol "CL" denotes the human kappa constant region.

Example 2

Expression, Purification and Characterization of Multivalent Anti-CD79a IgG1 Antibodies The expression vectors pCh9G6-IgG1, pCh9G6-IgG1/M and pCh9G6-MVIgG1 were introduced into the chromosome of a mouse myeloma cell line NS0 (European Collection of Heavy chain constant region encoded in pCh9G6-MVIgG1 (SEQ ID NO: 7):
ASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGKDQDTAIRVFAIP

PSFASIFLTKSTKLTCLVTDLTTYDSVTISWTRQNGEAVKTHTNISESHPNATFSAVGE

ASICEDDWNSGERFTCTVTHTDLPSPLKQTISRPKGVALHRPDVYLLPPAREQLNLRE

SATITCLVTGFSPADVFVQWMQRGQPLSPEKYVTSAPMPEPQAPGRYFAHSILTVSEE

EWNTGETYTCVVAHEALPNRVTERTVDKSTGKPTLYNVSLVMSDTAGTCY

Animal Cell Cultures, Salisbury, Wiltshire, UK) to obtain cell lines stably producing Ch9G6-IgG1, Ch9G6-IgG1/M and Ch9G6-MVIgG1 antibodies, respectively. NS0 cells were grown in DME medium containing 10% fetal bovine serum (FBS; HyClone, Logan, Utah) at 37° C. in a 7.5% $CO_2$ incubator. Stable transfection into NS0 was carried out by electroporation as described in Bebbington et al. (Bio/Technology 10: 169-175, 1992). Before transfection, each expression vector was linearized using FspI. In a typical experiment, approximately $10^7$ cells were transfected with 20 μg of linearized plasmid, suspended in DME medium containing 10% FBS, and plated into several 96-well plates. After 48 hr, selection media (DME medium containing 10% FBS, HT media supplement (Sigma, St. Louis, Mo.), 0.25 mg/ml xanthine and 1 μg/ml mycophenolic acid) was applied. Approximately 10 days after the initiation of selection, culture supernatants of transfectants were assayed for antibody production.

Expression of antibodies was measured by sandwich ELISA. In a typical experiment, an ELISA plate was coated overnight at 4° C. with 100 μl/well of 1/2,000-diluted goat anti-human IgG Fcγ-chain-specific (for Ch9G6-IgG1 and Ch9G6-MVIgG1 antibodies) or anti-human IgM Fcμ-chain-specific (for Ch9G6-IgG1/M) polyclonal antibody in PBS (phosphate-buffered saline, pH 7.4), washed with Wash Buffer (PBS containing 0.05% Tween 20), and blocked for 0.5 hr at room temperature with 200 μl/well of Block Buffer (PBS containing 2% Skim Milk and 0.05% Tween 20). After washing with Wash Buffer, 100 μl/well of test samples appropriately diluted in ELISA Buffer (PBS containing 1% Skim Milk and 0.025% Tween 20) were applied to the ELISA plate. An appropriate human IgG/κ or IgM/κ antibody was used as a standard. After incubating the ELISA plate for 1 hr at room temperature and washing with Wash Buffer, bound antibodies were detected using 100 μl/well of 1/2,000-diluted HRP-conjugated goat anti-human kappa chain polyclonal antibody in ELISA buffer. After incubating for 1 hr at room temperature and washing with Wash Buffer, color development was performed by adding 100 μl/well of ABTS substrate. Color development was stopped by adding 100 μl/well of 2% oxalic acid. Absorbance was read at 405 nm.

NS0 stable transfectants producing each of Ch9G6-IgG1, Ch9G6-IgG1/M and Ch9G6-MVIgG1 antibodies were adapted to growth in serum-free media using Hybridoma SFM (Invitrogen) and cultured in a roller bottle to the density of about $10^6$/ml, fed with 1/10th volume of 60 mg/ml of Ultrafiltered Soy Hydrolysate (Irvine Scientific, Santa Ana, Calif.) dissolved in SFM4MAb media (HyClone), and grown further until the cell viability became less than 50%. After centrifugation and filtration, culture supernatant was loaded onto a Protein A column (HiTrap MABSelect SuRe, GE Healthcare, Piscataway, N.J.) for Ch9G6-IgG1 and Ch9G6-MVIgG1. The column was washed with PBS before the antibody was eluted with 0.1 M glycine-HCl (pH 3.0). Since Ch9G6-IgG1/M, which lacks the CH2 and CH3 regions of the human gamma-1 heavy chain, did not bind to protein A, culture supernatant of NS0 stable transfectants producing Ch9G6-IgG1/M was loaded onto a goat anti-human IgM agarose column (Sigma). The anti-human IgM agarose column was washed with PBS before the antibody was eluted with 0.1 M glycine-HCl (pH 2.5). The buffer of all eluted antibodies was neutralized with 1 M Tris-HCl (pH 8) and then changed to PBS by dialysis. Antibody concentration was determined by measuring absorbance at 280 nm (1 mg/ml=1.4 OD). Ch9G6-IgG1, Ch9G6-IgG1/M and Ch9G6-MVIgG1 were confirmed to bind specifically to human CD79a.

Purified Ch9G6-IgG1, Ch9G6-IgG1/M and Ch9G6-MVIgG1 antibodies were characterized by SDS-PAGE according to standard procedures. Analysis under reducing conditions indicated that each antibody is comprised of two chains. The molecular weight of each chain was estimated by comparing the mobility on the gel to that of molecular weight markers. The light chain, which is common among Ch9G6-IgG1, Ch9G6-IgG1/M and Ch9G6-MVIgG1, was estimated to have a molecular weight of approximately 26 kDa. The molecular weight of the heavy chain was estimated to be 54 kDa for Ch9G6-IgG1, 58 kDa for Ch9G6-IgG1/M, and 76 kDa for Ch9G6-MVIgG1. The estimated molecular weight of each of the light and heavy chains is in agreement with the expected molecular weight based on the corresponding amino acid sequence.

The molecular size of Ch9G6-IgG1, Ch9G6-IgG1/M and Ch9G6-MVIgG1 in the native form was analyzed by gel filtration using the AKTA Basic FPLC system with a Superose 6 10/300 GL column which has a separation range from 5 kDa to 5,000 kDa of globular proteins (GE Healthcare, Indianapolis, Ind.). PBS was used as elution buffer. FIGS. 3C-E shows the elution patterns of Ch9G6-IgG1 (FIG. 3C), Ch9G6-IgG1/M (FIG. 3D) and Ch9G6-MVIgG1 (FIG. 3E). Only one dominant peak was observed for each of Ch9G6-IgG1 (at 16.7 ml of elution) and Ch9G6-MVIgG1 (at 9.9 ml), whereas two major and several minor peaks existed for Ch9G6-IgG1/M. Human monoclonal IgM antibody purified from a myeloma cell line (Jackson ImmunoResearch, West Grove, Pa.) was eluted at 10.4 ml (FIG. 3B). By comparing to the elution pattern of the molecular weight standards (Gel Filtration Standard, BioRad, Hercules, Calif.) (FIG. 3A), the molecular weight of Ch9G6-IgG1/M in the two major peaks at 11.7 ml and 14.8 ml of elution was estimated to be approximately 800 kDa and 220 kDa, respectively. The molecular weight of Ch9G6-IgG1 in the dominant peak was estimated to be 154 kDa, which corresponds to the predicted molecular weight of a monomer of Ch9G6-IgG1 (160 kDa) based on the size of its heavy and light chain on SDS-PAGE. Ch9G6-MVIgG1 was eluted at 9.9 ml while human IgM was eluted at 10.4 ml, indicating that Ch9G6-MVIgG1 is slightly larger than human IgM. Since the SDS-PAGE analysis indicated that the molecular weight of the heavy and light chains of Ch9G6-MVIgG1 was 76 kDa and 26 kDa, respectively, the molecular weight of a monomer of Ch9G6-MVIgG1 is calculated to be approximately 200 kDa, which is slightly larger than the monomer of human IgM (roughly 180 kDa). As human IgM purified from myeloma cells is likely to exist as a pentamer (or possibly as a hexamer), it was therefore concluded that Ch9G6-MVIgG1 purified from NS0 cells also existed as a pentamer or hexamer in the native form.

Example 3

Apoptosis by Multivalent Anti-CD79a IgG1 Antibodies

The human Burkitt's lymphoma cell line Ramos expresses on the cell surface B cell receptors composed of membrane-bound IgM/lambda, CD79a and CD79b proteins (Ollila et al., Mol. Immunol. 44:3537-3551, 2007; Reth, Annu. Rev. Immunol. 10:97-121, 1992). Multimerization of B cell receptors by cross-linking is known to induce apoptosis of Ramos cells (Ollila et al., supra).

Ramos cells were grown in DME media containing 10% FBS. To assess the ability of Ch9G6-IgG1 and Ch9G6-MVIgG1 antibodies to multimerize B cell receptors on the cell surface via binding to CD79a proteins, resulting in induction of apoptosis, each antibody was incubated with Ramos cells in triplicate at a final concentration of 1 µg/ml. Ch9G6-IgG1 was also added at 1 µg/ml together with 10 µg/ml of goat anti-human IgG polyclonal antibody for cross-linking. As a positive control of apoptosis, 1 µg/ml goat anti-human lambda light chain polyclonal antibody was incubated with Ramos cells. After culturing in a 7.5% CO2 incubator for 3 days, cell viability was measured with alamarBlue (Invitrogen) according to the manufacturer's protocol.

Figure 4:
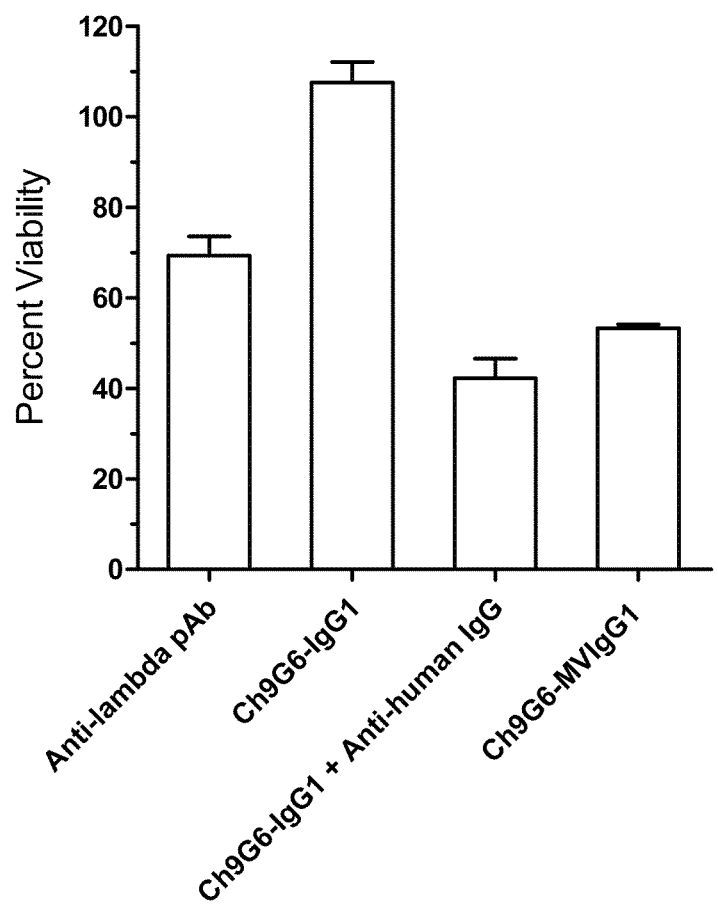
FIG. 4: Induction of apoptosis of Ramos cells by multivalent anti-CD79a IgG1 antibodies.

Percent cell viability was calculated by normalizing the absorbance value in the presence of test antibodies to that in the absence of test antibodies. The absorbance value with no cells was used as background. The viability was 69% for goat anti-human lambda light chain polyclonal antibody ("Antilambda pAb" in the figure), 107% for Ch9G6-IgG1, 42% for a mixture of Ch9G6-IgG1 and goat anti-human IgG polyclonal antibody ("Ch9G6-IgG1+Anti-human IgG" in the figure), and 53% for Ch9G6-MVIgG1. Divalent Ch9G6-IgG1 did not induce apoptosis of Ramos cells, whereas crosslinked Ch9G6-IgG1 was able to induce apoptosis. Ch9G6-MVIgG1 induced apoptosis of Ramos cells almost as efficiently as cross-linked Ch9G6-IgG1 did. Ch9G6-MVIgG1 functioned as a multivalent anti-CD79a antibody is capable of multimerizing B cell receptors on the cell surface and inducing apoptosis of Ramos cells (FIG. 4).

Example 4

Binding of Multivalent IgG1 Antibodies to Neonatal Fc Receptors

The ability of Ch9G6-IgG1, Ch9G6-IgG1/M and Ch9G6-MVIgG1 antibodies to bind to FcRn in a pH-dependent manner was analyzed by flow cytometry using NS0 cells expressing human FcRn on the cell surface (NS0/FcRn cells). NS0/FcRn transfectants stably expressing human FcRn, a heterodimer composed of the FcRn α chain and β2-microglubulin, on the cell surface was generated following the general procedure described by Hinton et al. (J. Biol. Chem. 279:6213-6216 2004), which is incorporated herein by reference. Ch9G6-IgG1, Ch9G6-IgG1/M and Ch9G6-MVIgG1 at 1 µg/ml were separately incubated with NS0/FcRn cells at pH 6.0 and 7.5 at the primary staining step following the procedure described by Hinton et al. (supra). Antibodies binding to FcRn were detected using PE-labeled goat polyclonal anti-human gamma chain antibody (for Ch9G6-IgG1 and no antibody control) or PE-labeled goat polyclonal anti-human µ chain antibody (for Ch9G6-IgG1/M, Ch9G6-MVIgG1 and no antibody control) at the secondary staining step. As shown in FIG. 5, both Ch9G6-IgG1 and Ch9G6-MVIgG1 bound strongly to FcRn at pH 6.0. Their FcRn binding was significantly weaker at pH 7.5 than at pH 6.0, exhibiting pH-dependent binding to FcRn, indicating that these antibodies have a long serum half-life. Ch9G6-IgG1/M hardly bound to FcRn at both pH 6.0 and 7.5, indicating a short serum half-life of Ch9G6-IgG1/M. This is consistent with the fact that Ch9G6-IgG1/M lacks the binding site to FcRn.

Example 5

Binding of Multivalent IgG1 Antibodies to CD16

Interaction of the Fc region of cell-bound IgG1 and IgG3 antibodies with CD16 molecules (also called Fcγreceptor type III) expressed on the surface of NK cells triggers antibody-dependent cell-mediated cytotoxicity (ADCC) by NK cells against antibody-bound cells in humans (Hulett et al., Adv. Immunol. 57:1-127, 1994). The CD16 binding site exists at the lower hinge encoded in the CH2 region of the human gamma-1 and gamma-3 chains (Sarmay et al., Mol. Immunol. 29:633-639, 1992).

Binding of multivalent IgG1 antibodies to human CD16 was analyzed by flow cytometry. HEK293 cells transiently expressing human CD16 on the surface were incubated with 1 µg/ml of Ch9G6-IgG1, Ch9G6-IgG1/M, Ch9G6-MVIgG1, or the mouse monoclonal anti-human CD16 IgG antibody 3G8 (BioLegend, San Diego, Calif.) in FACS Buffer (PBS containing 0.5% bovine serum albumin and 0.025% sodium azide) for 30 min on ice at the primary antibody binding step. As a control, HEK293 cells expressing human CD16 were also incubated without test antibodies. After washing with FACS buffer, cells were incubated with phycoerythrin (PE)-labeled goat polyclonal anti-human gamma heavy chain antibody (for Ch9G6-IgG1, Ch9G6-MVIgG1, and no antibody control), PE-labeled goat polyclonal anti-human µ heavy chain antibody (for Ch9G6-IgG1/M, Ch9G6-MVIgG1, and no antibody control) or PE-labeled goal polyclonal anti-mouse gamma heavy chain antibody in FACS buffer for 15 min on ice at the secondary staining step. After washing with FACS buffer, stained cells were suspended in FACS buffer and analyzed by flow cytometry.

Figure 6:
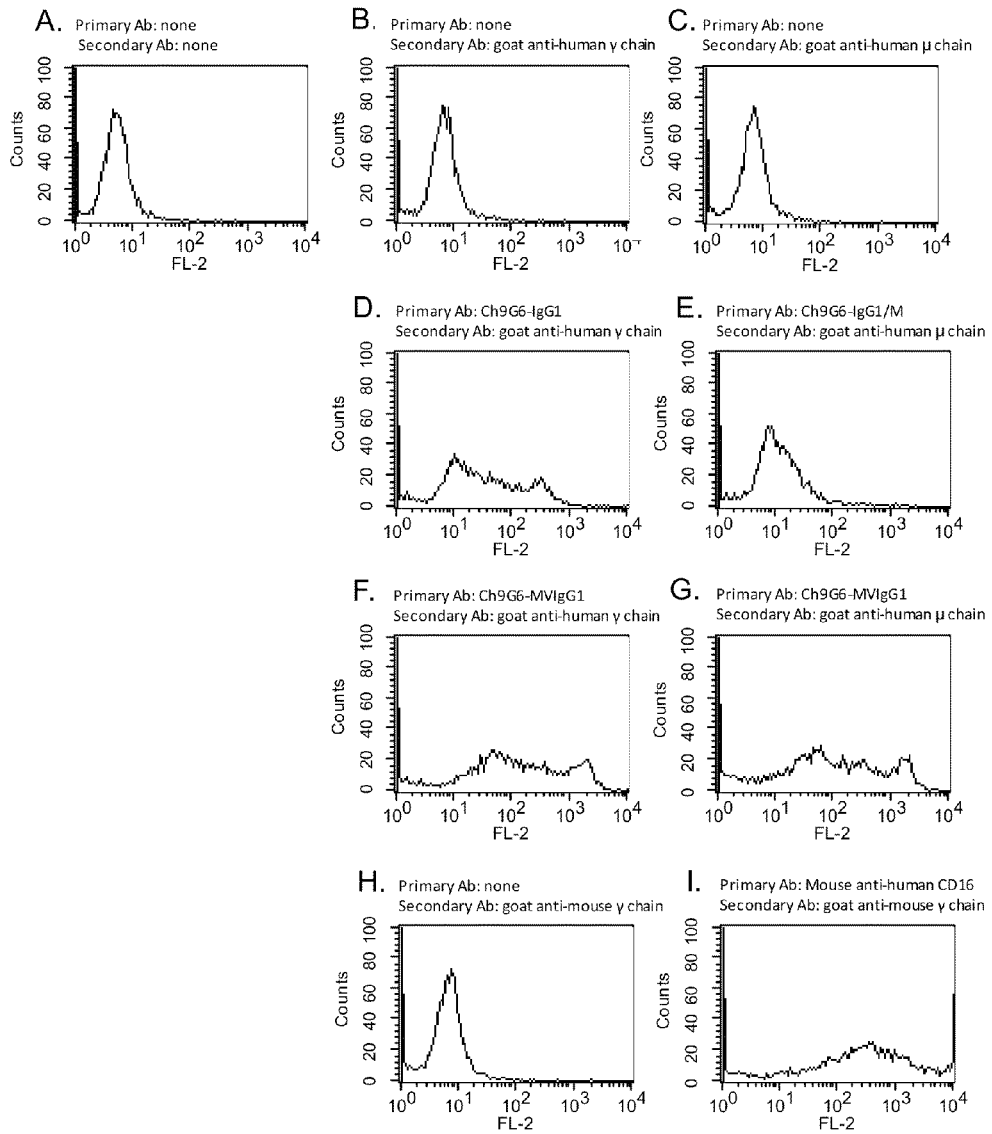
FIGS. 6A-I: Binding of multivalent IgG1 antibodies to CD16.

The mouse anti-CD16 antibody bound strongly to HEK293 cells transiently expressing human CD16 (FIG. 6I). Ch9G6-IgG1 also showed a strong binding to human CD16 (FIG. 6D). Ch9G6-MVIgG1 showed even a stronger binding to CD16 than Ch9G6-IgG1 did (FIG. 6F), indicating the capability of exerting ADCC. On the other hand, Ch9G6-IgG1/M showed only marginal binding to human CD16 (FIG. 6E) when compared the cells stained with PE-labeled goat anti-µ heavy chain antibody alone (FIG. 6C). The apparent weak binding of Ch9G6-IgG1/M to CD16 is not due to PE-labeled goat anti-µ heavy chain antibody because strong CD16 binding of Ch9G6-MVIgG1 was observed when PE-labeled goat anti-µ heavy chain antibody was used at the secondary staining step (FIG. 6G). The inability of Ch9G6-IgG1/M to bind to CD16, which results in no ADCC activity, is consistent with the fact that Ch9G6-IgG1/M lacks the CH2 and CH3 regions of the human gamma-1 heavy chain.

Example 6

Generation, Expression, Purification and Characterization of Multivalent Anti-CD30 IgG1 Antibodies The mouse hybridoma producing the anti-human CD30 monoclonal antibody San11 was isolated at JN Biosciences using recombinant human CD30 proteins as immunogens and following standard hybridoma techniques. The San11 VH and VL sequences were determined by standard experimental procedures such as the method described by Tsurushita et al. (supra). The San11 VH amino acid sequence, including the signal peptide, is shown below. The mature San11 VH sequence starts at position 20 in SEQ ID NO:8.

```
San11 VH (SEQ ID NO: 8):
MKCSWVIFFLMAVVTGVNSEVQLQQSGAELVKPGASVKLSCTASGFNIK

DTYMHWVKQRPEQGLEWIGRIDPANGDTIYDPNFQGKATITAYTSSNTA

YLQLSSLTSEDTAVYYCARGYYGSSYWYFDVWGAGTTVTVSS
```

The San11 VL amino acid sequence, including the signal peptide, is shown below. The mature San11 VL sequence starts at position 21 in SEQ ID NO:9.

San11 VL (SEQ ID NO: 9):
MESDTLLLWVLLLWVPGSTGDIVLTQSPASLAVSLGQRATISCRASESV

EYYGTGLMQWYQQKPGQPPKLLIYSASNVESGVPARFTGSGSGTDFSLN

IHPVEEDDIAMYFCQQSRKVPWTFGGGTKLEIKR

The mammalian expression vectors pChSan11-IgG1 and pChSan11-MVIgG1 were constructed by the following procedure. First, the San11 VH gene was constructed as an exon including a splice donor signal at the 3' end of the coding region and the flanking SpeI and HindIII sites. Likewise, the San11 VL gene was constructed as an exon including a splice donor signal and the flanking NheI and EcoRI sites. The SpeI-HindIII fragment carrying the San11 VH exon and the NheI-EcoRI fragment carrying the San11 VL exon were introduced into the corresponding sites of pCh9G6-IgG1, resulting in generation of pChSan11-IgG1. Similarly, the SpeI-HindIII fragment carrying the San11 VH exon and the NheI-EcoRI fragment carrying the San11 VL exon were introduced into the corresponding sites of pCh9G6-MVIgG1, resulting in generation of pChSan11-MVIgG1. The overall structure of pChSan11-IgG1 and pChSan11-MVIgG1 is identical to that of pCh9G6-IgG1 and pCh9G6-MVIgG1 (FIG. 1), respectively. The schematic structure of antibodies produced from pChSan11-IgG1 and pChSan11-MVIgG1 (ChSan11-IgG1 and ChSan11-MVIgG1, respectively) is shown in FIG. 2.

Generation of NS0 stable transfectants producing each of ChSan11-IgG1 and ChSan11-MVIgG1 was performed as described in Example 2. Purification of ChSan11-IgG1 and ChSan11-MVIgG1 by Protein A affinity chromatography was carried out as described in Example 2. SDS-PAGE analysis of ChSan11-IgG1 and ChSan11-MVIgG1 under reducing conditions showed that each antibody was comprised of two chains. By comparing to molecular weight markers, the molecular weight of the light chain was estimated to be 25 kDa for both ChSan11-IgG1 and ChSan11-MVIgG1. The molecular weight of the heavy chain was estimated to be 53 kDa for ChSan11-IgG1 and 79 kDa for ChSan11-MVIgG1. The size of each of the light and heavy chains observed in SDS-PAGE was in agreement with the expected size based on the corresponding amino acid sequence.

Figure 7:
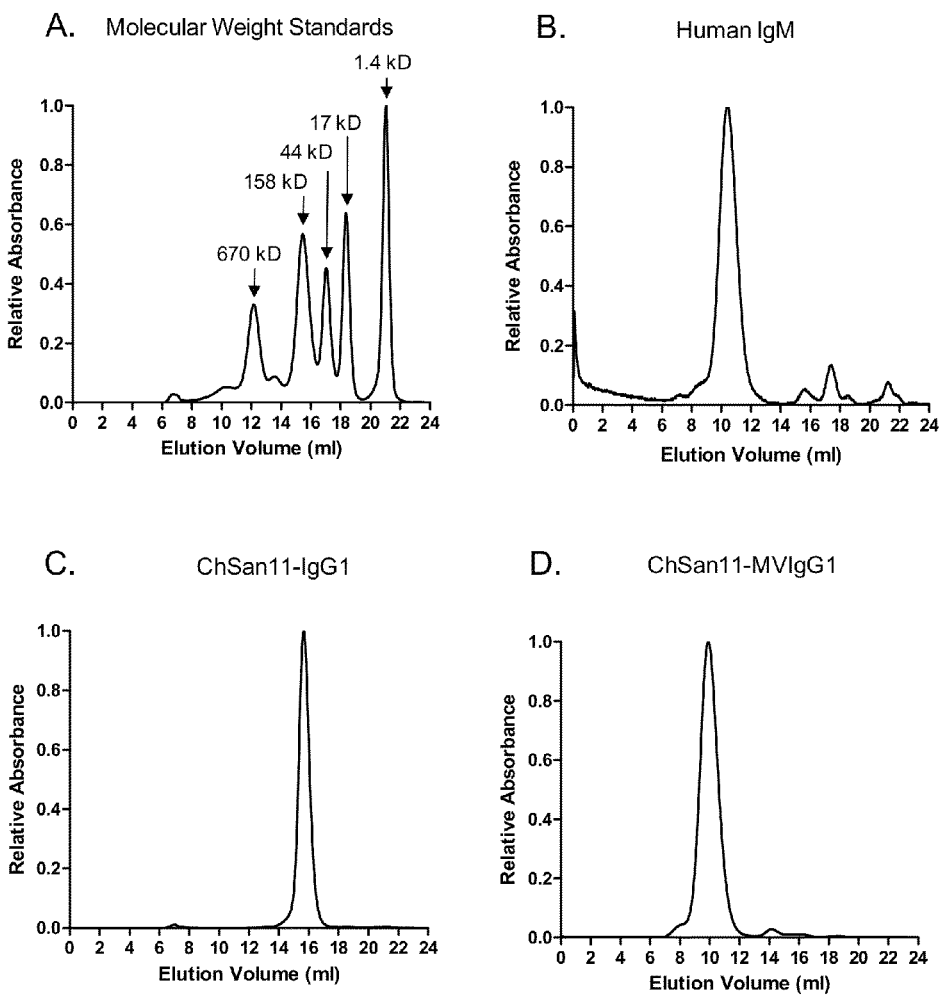
FIGS. 7A-D: Elution pattern of anti-CD30 IgG1 antibodies from a Superose 6 gel filtration column.

The molecular size of native ChSan11-IgG1 and ChSan11-MVIgG1 antibodies was analyzed by gel filtration using a Superose 6 10/300 GL as described in Example 2. FIG. 7 shows the elution patterns of ChSan11-IgG1 and ChSan11-MVIgG1 antibodies. ChSan11-IgG1 had a single dominant peak at 15.7 ml of elution (FIG. 7C). By comparing to the calibration curve with the elution pattern of the molecular weight standards (Gel Filtration Standard, BioRad) (FIG. 7A), the molecular weight of ChSan11-IgG1 in the dominant peak was estimated to be approximately 150 kDa. This corresponds to the predicted molecular weight of a monomer of ChSan11-IgG1 (156 kDa) based on the size of its light and heavy chains on the SDS-PAGE. ChSan11-MVIgG1 had a single dominant peak at 9.9 ml of elution (FIG. 7D). Human monoclonal IgM antibody (Jackson ImmunoResearch) was eluted at 10.4 ml (FIG. 7B) under the same condition. Considering that the monomer of ChSan11-MVIgG1, which has a molecular weight of roughly 208 kDa based on the SDS-PAGE result, is slightly larger than the monomer of human IgM (approximately 180 kDa), ChSan11-MVIgG1 purified from NS0 cells was concluded to exist as a pentamer or hexamer in the native form.

Figure 8:
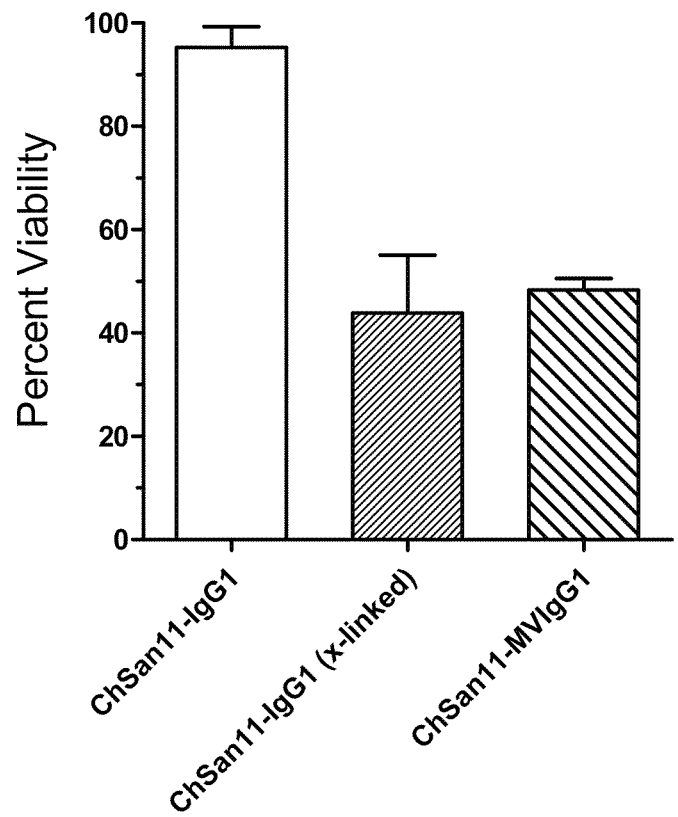
FIG. 8: Cytostasis of Karpas 299 cells by multivalent anti-CD30 IgG1 antibodies.

Cross-linking of CD30 proteins on the cell surface by treatment with a mixture of a monoclonal anti-CD30 IgG antibody and a polyclonal anti-IgG antibody caused cytostasis of the human T cell lymphoma cell line Karpas 299 (Wahl et al., Cancer Res. 62:3736-3742, 2002). To investigate the ability of ChSan11-MVIgG1 to cross-link CD30 proteins, $2 \times 10^5$ Karpas 299 cells were incubated in 0.2 ml of RPMI-1640 media containing 10% FBS in a 96-well plate in the presence of (a) 2 µg/ml of ChSan11-IgG1, (b) a mixture of 2 µg/ml of ChSan11-IgG1 and 10 µg/ml of goat anti-human IgG polyclonal antibody, or (c) 2 µg/ml of ChSan11-MVIgG1 (FIG. 8). After a 5 day incubation, Karpas 299 cells were incubated with the tetrazolium salt WST-8 (Dojindo Molecular Technologies, Rockville, Md.) and absorbance at 450 nm, which is indicative of dehydrogenase activity and therefore cell viability, was measured. Percent cell viability was calculated by normalizing the absorbance value in the presence of test antibodies to that in the presence of a control IgG antibody that does not bind to Karpas 299 cells. The absorbance value with no cells was used as a background. The viability of Karpas 299 cells was 95% with ChSan11-IgG1, 44% with a mixture of ChSan11-IgG1 and goat anti-human IgG polyclonal antibody ("ChSan11-IgG1 α-linked)" in the figure), and 48% with ChSan11-MVIgG1 (FIG. 8). ChSan11-MVIgG1 induced cytostasis of Karpas 299 cells almost as efficiently as ChSan11-IgG1 cross-linked by goat anti-human IgG polyclonal antibody. ChSan11-MVIgG1 thus functions as a multivalent antibody and cross-links CD30 molecules on the cell surface to induce growth arrest of Karpas 299 cells.

Example 7

Expression of ChSan11-MVIgG1 in HEK293 Cells

Figure 9:
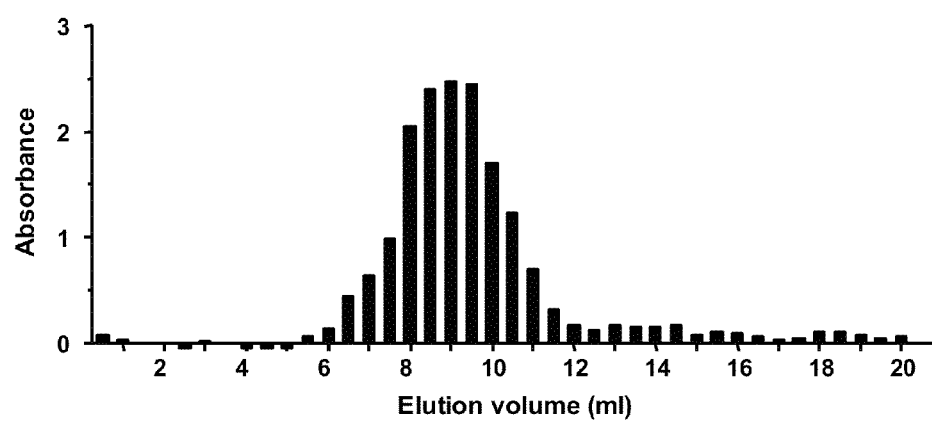
FIG. 9: Elution pattern of multivalent anti-CD30 IgG1 antibody expressed in HEK293 cells from a Superose 6 gel filtration column.

IgM forms a pentamer in the presence of J chains, e.g., in the mouse myeloma cell line NS0, while IgM forms a hexamer in the absence of J chains, e.g., in the Chinese hamster ovary cell line CHO (Gilmour et al. Transfus. Med. 18:167-174 2008). To investigate the structure in the absence of J chains, ChSan11-MVIgG1 was expressed in the human embryonic kidney cell line HEK293. The pChSan11-MVIgG1 vector was transiently transfected into HEK293 cells using Lipofectamine 2000 (Invitrogen) according to the supplier's protocol. The culture supernatant of transiently transfected HEK293 cells was fractionated using a Superose 6 gel filtration column following the procedure described in Example 2. The presence of ChSan11-MVIgG1 in each 0.5 ml fraction was monitored by ELISA as described in Example 2. FIG. 9 shows the level of ChSan11-MVIgG1 in each fraction. The highest ELISA signal for ChSan11-MVIgG1 was observed at 9.0 ml of the elution. No significant ELISA signals were detected at the fractions around 16 ml of elution where the monomeric ChSan11-IgG1 antibodies were eluted (FIG. 7C). As a human monoclonal IgM antibody was eluted at 10.4 ml under the same condition, native ChSan11-MVIgG1 is larger than IgM. It was therefore concluded that ChSan11-MVIgG1 was produced as a pentamer or hexamer, or possibly larger than a hexamer, in the absence of J chains.

Example 8

Generation, Expression, Purification and Characterization of Multivalent Chimeric Anti-DR5 IgG1 Antibodies The coding region of the VH gene of a mouse anti-human DR5 monoclonal antibody was converted to an exon including a signal peptide-coding sequence, a splice donor signal, and flanking SpeI and HindIII sites. Likewise, the VL gene of the same mouse anti-DR5 monoclonal antibody was converted to an exon including a signal peptide-coding sequence, a splice donor signal, and flanking NheI and EcoRI sites. The SpeI-HindIII fragment carrying the VH exon and the NheI-EcoRI fragment carrying the VL exon of the mouse anti-DR5 monoclonal antibody were introduced to the corresponding sites of pCh9G6-IgG1 to generate pChADR5-IgG1. Similarly, the SpeI-HindIII VH fragment and the NheI-EcoRI VL fragment were introduced into pCh9G6-MVIgG1 to generate pChADR5-MVIgG1. The overall structure of pChADR5-IgG1 and pChADR5-MVIgG1 is identical to that of pCh9G6-IgG1 and pCh9G6-MVIgG1 (FIG. 1), respectively, except that the VH and VL genes are different. The schematic structure of antibodies produced from pChADR5-IgG1 and pChADR5-MVIgG1 (ChADR5-IgG1 and ChADR5-MVIgG1, respectively) is shown in FIG. 2.

Generation of NS0 stable transfectants producing each of ChADR5-IgG1 and ChADR5-MVIgG1 was performed as described in Example 2. Purification of ChADR5-IgG1 and ChADR5-MVIgG1 by Protein A affinity chromatography was carried out with the method described in Example 2. SDS-PAGE analysis of ChADR5-IgG1 and ChADR5-MVIgG1 under reducing conditions showed that each antibody is comprised of two chains: a light chain of the common size between the two antibodies and a heavy chain with a different size for each antibody. By comparing to the location of molecular weight markers on the gel, the molecular weight of the common light chain was estimated to be 26 kDa. The molecular weight of the heavy chain was estimated to be 51 kDa for ChADR5-IgG1 and 75 kDa for ChADR5-MVIgG1.

Figure 10:
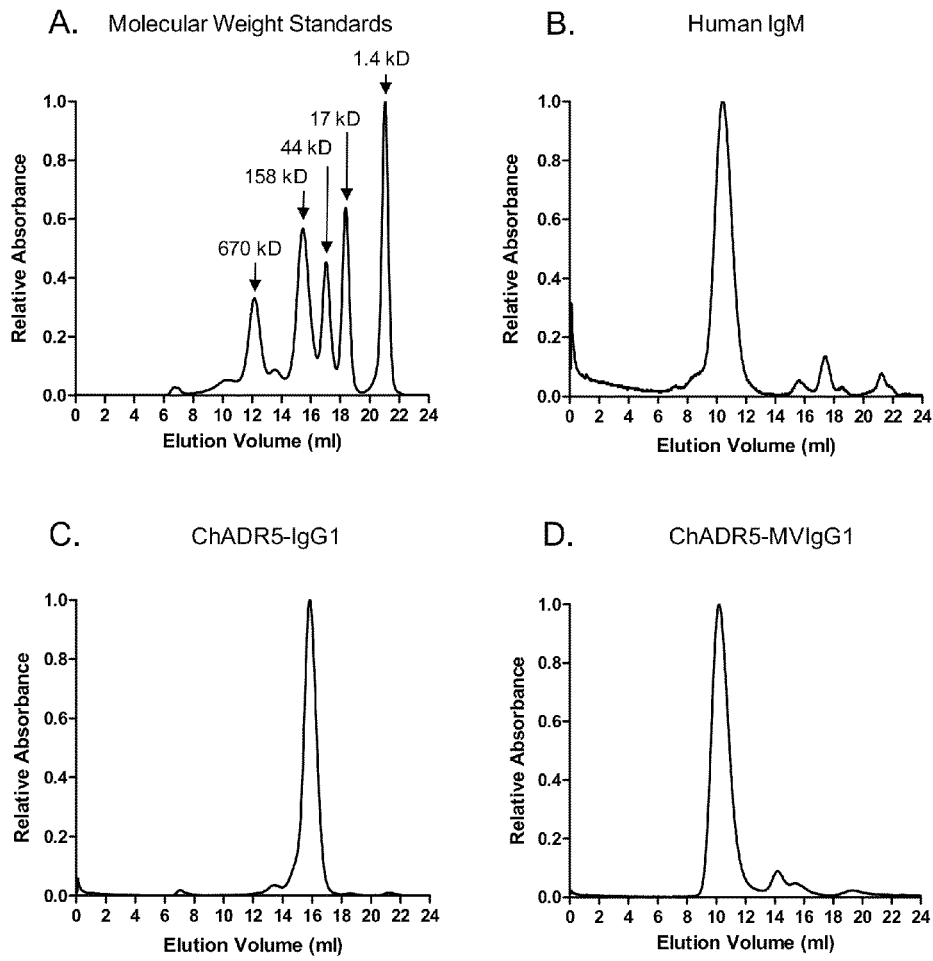
FIGS. 10A-D: Elution pattern of anti-DR5 IgG1 antibodies from a Superose 6 gel filtration column.

The size of native ChADR5-IgG1 and ChADR5-MVIgG1 antibodies was analyzed by gel filtration using a Superose 6 10/300 GL column as described in Example 2. Their elution pattern is shown in FIGS. 10A-D. ChADR5-IgG1 had a single dominant peak at 15.9 ml of elution (FIG. 10C). By comparing to the elution pattern of the molecular weight standards (Gel Filtration Standard, BioRad) (FIG. 10A), the molecular weight of ChADR5-IgG1 in the dominant peak was estimated to be approximately 150 kDa. This corresponds to the predicted molecular weight of a monomer of ChADR5-IgG1. ChADR5-MVIgG1 had a single dominant peak at 9.2 ml of elution (FIG. 10D). Since a human IgM monoclonal antibody purified from human myeloma cells (Jackson ImmunoResearch) was eluted at 10.4 ml (FIG. 10B), the molecular size of ChADR5-MVIgG1 is slightly larger than that of human IgM. Considering that a monomer of ChADR5-MVIgG1 is roughly 200 kDa and a monomer of human IgM is approximately 180 kDa, it was concluded that ChADR5-MVIgG1 existed as a pentamer or hexmer in the native form.

Figure 11:
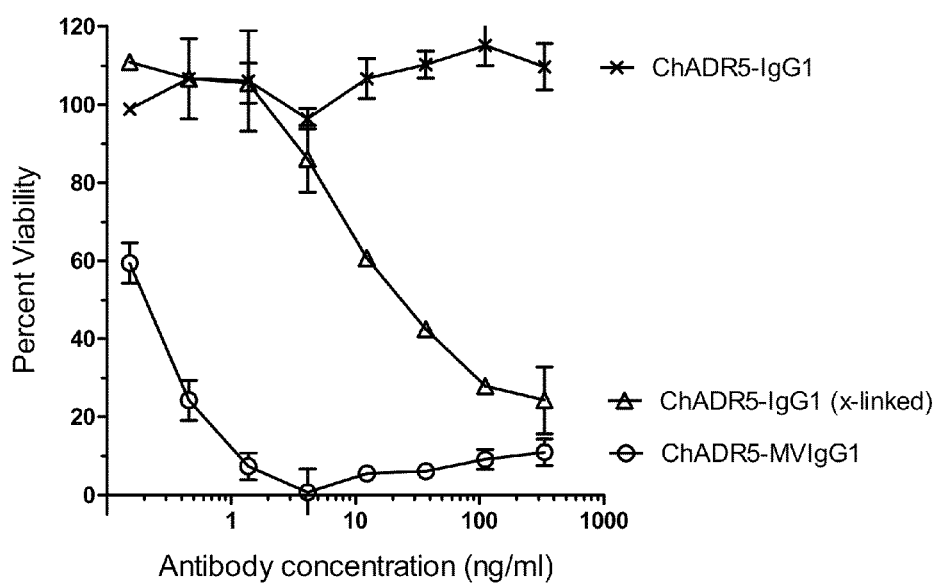
FIG. 11: Apoptosis of Jurkat cells induced by multivalent anti-DR5 IgG1 antibodies.

Cross-linking of DR5 molecules on the surface induces apoptosis of the human T cell leukemia cell line Jurkat (Guo et al., J. Biol. Chem. 280:41940-41952, 2005). The ability of ChADR5-IgG1 and ChADR5-MVIgG1 to induce apoptosis was assessed by incubation with Jurkat cells. Three sets of test antibodies, (i) ChADR5-IgG1, (ii) ChADR5-IgG1 mixed with ten-fold excess of goat anti-human gamma heavy chain polyclonal antibody for cross-linking, and (iii) ChADR5-MVIgG1, were added at various concentrations starting at 333 ng/ml of final concentration and serial 3-fold dilutions. Cells were incubated in a 96-well plate for 1 day at 37° C. in a 7.5% CO2 incubator. Cell viability was measured using WST-8 reagent (Dojindo). The absorbance value of Jurkat cells without test antibodies was used for 100% viability and the value without cells was used for background. The result is shown in FIG. 11. ChADR5-IgG1 showed no capacity to induce apoptosis. ChADR5-IgG1 cross-linked with 10-fold excess of goal anti-human human gamma heavy chain polyclonal antibody ("ChADR5-IgG1 (x-linked)" in the figure) showed approximately 70% cell killing at 111 ng/ml and less than 20% killing at 4 ng/ml. ChADR5-MVIgG1 exhibited a stronger apoptosis-inducing activity, killing more than 90% cells between 333 ng/ml and 1.4 ng/ml. ChADR5-MVIgG1 showed nearly 40% cell killing even at 0.15 ng/ml. ChADR5-MVIgG1 thus functioned as a multivalent antibody and efficiently cross-linked DR5 molecules on the cell surface.

Example 9

Generation of Multivalent Anti-CD79a IgG4 Antibodies

The pCh9G6-IgG4 vector for expression of a chimeric anti-CD79a IgG4 monoclonal antibody was constructed by replacing the genomic CH1, hinge, CH2 and CH3 region sequence of the human gamma-1 heavy chain in pCh9G6-IgG1 with a cDNA-derived fragment encoding the CH1, hinge, CH2 and CH3 regions of the human gamma-4 heavy chain (CH1(γ4), h(γ4), CH2(γ4) and CH3(γ4), respectively, in the figure) (FIG. 1). The amino acid sequence of the gamma-4 heavy chain constant region encoded in pCh9G6-IgG4 is shown below.

```
Heavy chain constant region encoded in pCh9G6-IgG4 (SEQ ID NO: 10):
ASTKGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPSCPAPEFLG

GPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK
```

The pCh9G6-MVIgG4 vector for expression of a multivalent chimeric anti-CD79a IgG4 monoclonal antibody was constructed by fusing the Cμ3 and Cμ4 regions (SEQ ID NO:5) in frame to the last amino acid of the CH3 region in pCh9G6-IgG4 (FIG. 1). The amino acid sequence of the heavy chain constant region encoded in pCh9G6-MVIgG4 is shown below.

Heavy chain constant region encoded in pCh9G6-MVIgG4 (SEQ ID NO: 11):
ASTKGPSVFPLAPCSRSTSESTAALGCLVKDYFPEPVTVSWNSGALTSGVHTFPAVLQ

SSGLYSLSSVVTVPSSSLGTKTYTCNVDHKPSNTKVDKRVESKYGPPCPSCPAPEFLG

GPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGKDQDTAIRVFAIPPSFA

SIFLTKSTKLTCLVTDLTTYDSVTISWTRQNGEAVKTHTNISESHPNATFSAVGEASIC

EDDWNSGERFTCTVTHTDLPSPLKQTISRPKGVALHRPDVYLLPPAREQLNLRESATI

TCLVTGFSPADVFVQWMQRGQPLSPEKYVTSAPMPEPQAPGRYFAHSILTVSEEEWN

TGETYTCVVAHEALPNRVTERTVDKSTGKPTLYNVSLVMSDTAGTCY

Generation of NS0 stable transfectants producing Ch9G6-MVIgG4 was performed as described in Example 2. Purification of Ch9G6-MVIgG4 by Protein A affinity chromatography was carried out with the method described in Example 2. SDS-PAGE analysis under reducing conditions showed that Ch9G6-MVIgG4 is comprised of an approximately 25 kDa light chain and an approximately 78 kDa heavy chain.

The molecular size of native Ch9G6-MVIgG4 was analyzed by gel filtration using a Superose 6 10/300 GL column as described in Example 2. One major peak (at 10.1 ml of elution) and one minor peak (at 14.1 ml of elution) were observed in the elution pattern of Ch9G6-MVIgG4 (FIG. 12C). By comparing to the elution pattern of BioRad's molecular weight standards (FIG. 12A) and human IgM (eluted at 10.4 ml; FIG. 12B), and considering the expected size of monomeric Ch9G6-MVIgG4 (~208 kDa) and IgM (~180 kDa), it was concluded that Ch9G6-MVIgG4 eluted at 10.1 ml was a pentamer or hexamer. Such multimeric Ch9G6-MVIgG4 constituted 83% of the total purified antibodies.

Example 10

Expression, Purification and Characterization of Multivalent IgG3 Antibodies

Three vectors were constructed for expression of a chimeric anti-CD79a IgG3 monoclonal antibody and its two derivatives. The pCh9G6-IgG3D vector was constructed by replacing the HindIII-EagI fragment carrying the genomic CH1, hinge, CH2 and CH3 regions of the human gamma-1 heavy chain in pCh9G6-IgG1 with the HindIII-EagI fragment carrying the genomic CH1, fourth hinge, CH2 and CH3 regions of the human gamma-3 heavy chain (CH1(γ3), h(γ3), CH2(γ3) and CH3(γ3), respectively, in the figure) (FIG. 1). The coding sequence of the first, second and third hinge regions was eliminated in pCh9G6-IgG3D. The amino acid sequence of the heavy chain constant region encoded in pCh9G6-IgG3D is shown below.

Heavy chain constant region encoded in pCh9G6-IgG3D (SEQ ID NO: 12):
ASTKGPSVFPLAPCSRSTSGGTAALGCLVKDYFPEPVTVSWNSGALTSGVHTFPAVL

QSSGLYSLSSVVTVPSSSLGTQTYTCNVNHKPSNTKVDKRVEPKSCDTPPPCPRCPAP

ELLGGPSVFLFPPKPKDTLMISRTPEVTCVVVDVSHEDPEVQFKWYVDGVEVHNAK

TKPREEQYNSTFRVVSVLTVLHQDWLNGKEYKCKVSNKALPAPIEKTISKTKGQPRE

PQVYTLPPSREEMTKNQVSLTCLVKGFYPSDIAVEWESSGQPENNYNTTPPMLDSDG

SFFLYSKLTVDKSRWQQGNIFSCSVMHEALHNRFTQKSLSLSPGK

The pCh9G6-IgG3D/M vector was constructed by fusing the Cμ3 and Cμ4 regions of the human μ heavy chain (SEQ ID NO:5) in frame to the last amino acid of the hinge region in pCh9G6-IgG3D (FIG. 1). The CH2 and CH3 exons of the human gamma-3 heavy chain were removed in pCh9G6-IgG3D/M. The structure of the resultant heavy chain constant region encoded in pCh9G6-IgG3D/M, which is composed of, from the N-terminus to the C-terminus, the CH1 and fourth hinge regions of the human gamma-3 heavy chain and the CH3 and CH4 regions of the human μ heavy chain, is identical to the heavy chain constant region of IgG-Cμ3-Cμ4 reported by Sorensen et al. (Int. Immunol. 12:19-27 2000). The amino acid sequence of the heavy chain constant region encoded in pCh9G6-IgG3D/M is shown below.

Heavy chain constant region encoded in pCh9G6-IgG3D/M (SEQ ID NO: 13):
ASTKGPSVFPLAPCSRSTSGGTAALGCLVKDYFPEPVTVSWNSGALTSGVHTFPAVL

QSSGLYSLSSVVTVPSSSLGTQTYTCNVNHKPSNTKVDKRVEPKSCDTPPPCPRCPDQ

DTAIRVFAIPPSFASIFLTKSTKLTCLVTDLTTYDSVTISWTRQNGEAVKTHTNISESHP

-continued
```
NATFSAVGEASICEDDWNSGERFTCTVTHTDLPSPLKQTISRPKGVALHRPDVYLLPP

AREQLNLRESATITCLVTGFSPADVFVQWMQRGQPLSPEKYVTSAPMPEPQAPGRYF

AHSILTVSEEEWNTGETYTCVVAHEALPNRVTERTVDKSTGKPTLYNVSLVMSDTA

GTCY
```

The pCh9G6-MVIgG3D vector was constructed by fusing the Cμ3 and Cμ4 regions of the human μ heavy chain (SEQ ID NO:5) in frame to the last amino acid of the CH3 exon of the human gamma-3 heavy chain in pCh9G6-IgG3D (FIG. 1). The amino acid sequence of the resulting heavy chain constant region encoded in pCh9G6-MVIgG3D is shown below.

```
Heavy chain constant region encoded in pCh9G6-MVIgG3D (SEQ ID NO: 14):
ASTKGPSVFPLAPCSRSTSGGTAALGCLVKDYFPEPVTVSWNSGALTSGVHTFPAVL

QSSGLYSLSSVVTVPSSSLGTQTYTCNVNHKPSNTKVDKRVEPKSCDTPPPCPRCPAP

ELLGGPSVFLFPPKPKDTLMISRTPEVTCVVVDVSHEDPEVQFKWYVDGVEVHNAK

TKPREEQYNSTFRVVSVLTVLHQDWLNGKEYKCKVSNKALPAPIEKTISKTKGQPRE

PQVYTLPPSREEMTKNQVSLTCLVKGFYPSDIAVEWESSGQPENNYNTTPPMLDSDG

SFFLYSKLTVDKSRWQQGNIFSCSVMHEALHNRFTQKSLSLSPGKDQDTAIRVFAIPP

SFASIFLTKSTKLTCLVTDLTTYDSVTISWTRQNGEAVKTHTNISESHPNATFSAVGEA

SICEDDWNSGERFTCTVTHTDLPSPLKQTISRPKGVALHRPDVYLLPPAREQLNLRES

ATITCLVTGFSPADVFVQWMQRGQPLSPEKYVTSAPMPEPQAPGRYFAHSILTVSEEE

WNTGETYTCVVAHEALPNRVTERTVDKSTGKPTLYNVSLVMSDTAGTCY
```

The schematic structure of the monomer form of the antibodies produced from pCh9G6-IgG3D, pCh9G6-IgG3D/M and pCh9G6-MVIgG3D (Ch9G6-IgG3D, Ch9G6-IgG3D/M and Ch9G6-MVIgG3D, respectively) is shown in FIG. 2.

Generation of NS0 stable transfectants producing each of Ch9G6-IgG3D, Ch9G6-IgG3D/M and Ch9G6-MVIgG3D antibodies was carried out as outlined in Example 2. NS0 stable transfectants producing a high level of Ch9G6-IgG3D, Ch9G6-IgG3D/M and Ch9G6-MVIgG3D antibodies were adapted to growth in serum-free media using Hybridoma SEM and expanded into a roller bottle as described in Example 2. After centrifugation and filtration, culture supernatant was loaded onto a Protein G Sepharose column (GE Healthcare) for Ch9G6-IgG3D and Ch9G6-MVIgG3D. The Protein G Sepharose column was washed with PBS before the antibody was eluted with 0.1 M glycine-HCl (pH 2.5). After neutralization with 1 M Tris-HCl (pH 8), the buffer of eluted antibody was changed to PBS by dialysis.

Since Ch9G6-IgG3D/M, which lacks the CH2 and CH3 regions of the human gamma-3 heavy chain, did not bind to Protein G, culture supernatant of NS0 stable transfectants producing Ch9G6-IgG3D/M was loaded onto a goat anti-human IgM agarose column (Sigma). The anti-human IgM agarose column was washed with PBS before the antibody was eluted with 0.1 M glycine-HCl (pH 2.5). After neutralization with 1 M Tris-HCl (pH 8), the buffer of eluted antibody was changed to PBS by dialysis.

Purified antibodies were characterized by SDS-PAGE according to standard procedures. Analysis under reducing conditions indicated that each of Ch9G6-IgG3D, Ch9G6-IgG3D/M and Ch9G6-MVIgG3D antibodies is comprised of two chains. The molecular weight of each chain was estimated by comparing the mobility on the gel to that of molecular weight markers. The light chain, which is common among Ch9G6-IgG3D, Ch9G6-IgG3D/M and Ch9G6-MVIgG3D, had a molecular weight of approximately 25 kDa. The molecular weight of the heavy chain was estimated to be 53 kDa for Ch9G6-IgG3D, 60 kDa for Ch9G6-IgG3D/M, and 81 kDa for Ch9G6-MVIgG3D. The estimated size of each of the light and heavy chains is in agreement with the size expected based on the corresponding amino acid sequence.

The size of Ch9G6-IgG3D, Ch9G6-IgG3D/M and Ch9G6-MVIgG3D antibodies in the native form was analyzed by gel filtration using the AKTA Basic FPLC system with a Superose 6 10/300 GL column as described in Example 2. FIG. 13 shows the elution patterns of Ch9G6-IgG3D (FIG. 13C), Ch9G6-IgG3D/M (FIG. 13D) and Ch9G6-MVIgG3D (FIG. 13E). A single dominant peak was observed with Ch9G6-IgG3D at 15.6 ml in the elution. By comparing to the elution pattern of Gel Filtration Standard (BioRad) (FIG. 13A), the molecular weight of Ch9G6-IgG3D in the dominant peak was estimated to be approximately 150 kDa, which corresponds to the predicted molecular weight of a monomer of Ch9G6-IgG3D from the SDS-PAGE result.

Four major peaks were observed with Ch9G6-IgG3D/M (FIG. 13D). The molecular weight of Ch9G6-IgG3D/M eluted at 12.3 ml, 15.0 ml and 16.1 ml was estimated to be 650 kDa, 180 kDa and 90 kDa, respectively. Proteins in the fourth major peak eluted at 20.8 ml, which were estimated to have a molecular weight of roughly 2 kDa, are likely to be degradation projects of Ch9G6-IgG3D/M that bound to and eluted from the anti-IgM agarose column.

A single dominant peak was observed with Ch9G6-MVIgG3D at 10.4 ml in the elution (FIG. 13E). Human IgM was also eluted at 10.4 ml (FIG. 13B). Considering the size of a monomer of Ch9G6-MVIgG3D (~200 kDa) and IgM (~180 kDa) estimated from the SDS-PAGE result, it was concluded that Ch9G6-MVIgG3D was produced as a pentamer or hexamer in the native form.

Example 11

Binding of Multivalent IgG3 Antibodies to FcRn

The ability of Ch9G6-IgG3D, Ch9G6-IgG3D/M and Ch9G6-MVIgG3D antibodies to bind to FcRn in a pH-dependent manner was analyzed by flow cytometry using NS0 cells expressing human FcRn on the cell surface (NS0/FcRn cells). Ch9G6-IgG3D, Ch9G6-Ig3D/M and Ch9G6-MVIgG3D at 1 µg/ml were separately incubated with NS0/FcRn cells at pH 6.0 and 7.5 at the primary staining step as described in Example 4. Antibodies binding to FcRn were detected using PE-labeled goat polyclonal anti-human gamma chain antibody (for Ch9G6-IgG3D and no antibody control) or PE-labeled goat polyclonal anti-human µ chain antibody (for Ch9G6-IgG3D/M, Ch9G6-MVIgG3D and no antibody control) at the secondary staining step. As shown in FIG. 14, Ch9G6-IgG3D bound strongly to FcRn at pH 6.0 and only weakly at pH 7.5. Similarly, Ch9G6-MVIgG3D bound strongly to FcRn at pH 6.0. FcRn binding of Ch9G6-MVIgG1 was much stronger at pH 6.0 than at pH 7.5. Thus, both Ch9G6-IgG3D and Ch9G6-MVIgG3D exhibited pH-dependent binding to FcRn, indicating these antibodies have a long serum half-life. Ch9G6-IgG3D/M did not show any significant binding to FcRn at pH 6.0 or 7.5, indicating a short serum half-life of Ch9G6-IgG3D/M. This is consistent with the fact that Ch9G6-IgG3D/M lacks the binding site to FcRn.

Example 12

Binding of Multivalent IgG3 Antibodies to CD16

Binding of multivalent IgG3 antibodies to human CD16 was analyzed by flow cytometry. HEK293 cells transiently expressing human CD16 on the surface were incubated with 1 µg/ml of Ch9G6-IgG3D, Ch9G6-IgG3D/M or Ch9G6-MVIgG3D in FACS Buffer (PBS containing 0.5% bovine serum albumin and 0.025% sodium azide) for 30 min on ice. As a control, HEK293 cells expressing human CD16 were also incubated without test antibodies. After washing with FACS buffer, cells were incubated with PE-labeled goat polyclonal anti-human gamma heavy chain antibody (for Ch9G6-IgG3D, Ch9G6-MVIgG3D and no antibody control) or PE-labeled goat polyclonal anti-human µ heavy chain antibody (for Ch9G6-IgG3D/M, Ch9G6-MVIgG3D and no antibody control) in FACS buffer at the secondary staining step for 15 min on ice. After washing with FACS buffer, stained cells were analyzed by flow cytometry.

Ch9G6-IgG3D showed a strong binding to human CD16 (FIG. 15D). Ch9G6-MVIgG1 showed even a stronger CD16 binding than Ch9G6-IgG3D did (FIG. 15F), indicating the capability of exerting ADCC. On the other hand, Ch9G6-IgG1/M showed very weak binding, if any, to human CD16 (FIG. 15E) when compared the cells stained with PE-labeled goat anti-µ heavy chain antibody alone (FIG. 15C), indicating that Ch9G6-IgG1/M has no ADCC activity. The insignificant binding of Ch9G6-IgG3D/M to CD16 is not due to the difference of PE-labeled secondary antibodies because strong CD16 binding of Ch9G6-MVIgG3D was observed when PE-labeled goat anti-µ heavy chain antibody was used at the secondary staining step (FIG. 15G). The inability of Ch9G6-IgG3D/M to bind to CD16 is consistent with the fact that Ch9G6-IgG3D/M lacks the CH2 and CH3 regions of the human gamma-3 heavy chain.

For generation of multivalent IgG2 antibodies, the last amino acid of the CH3 exon of the human gamma-2 heavy chain is fused in frame to the CH3 and CH4 regions of the human µ heavy chain. The resulting heavy chain is composed, from the N-terminus to the C-terminus, (i) the CH1, hinge and CH2 and CH3 regions of the human gamma-2 heavy chain, and then (ii) the CH3 and CH4 regions of the human µ heavy chain. The resulting multivalent IgG2 antibody is expressed in mammalian cells, such as NS0, CHO or HEK293 cells, purified from spent culture supernatant using a Protein A affinity column, and characterized with gel filtration and SDS-PAGE.

Example 13

Multivalent IgG2 Antibodies

For generation of multivalent IgG2 antibodies, the last amino acid of the CH3 exon of the human gamma-2 heavy chain is fused in frame to the Cµ3 and Cµ4 regions of the human µ heavy chain. The resulting heavy chain is composed, from the N-terminus to the C-terminus, (i) the CH1, hinge and CH2 and CH3 regions of the human gamma-2 heavy chain, and then (ii) the Cµ3 and Cµ4 regions of the human µ heavy chain. The resulting multivalent IgG2 antibody is expressed in mammalian cells, such as NS0, CHO or HEK293 cells, purified from spent culture supernatant using a Protein A affinity column, and characterized with gel filtration and SDS-PAGE.

Example 14

Multivalent IgA Antibodies

For generation of multivalent IgA antibodies, the last amino acid of the CH3 exon of the human alpha-1 or alpha-2 heavy chain is fused in frame to the CH3 and CH4 regions of the human µ heavy chain. The resulting heavy chain is composed, from the N-terminus to the C-terminus, (i) the CH1, CH2 and CH3 regions of the human alpha-1 or alpha-2 heavy chain, and then (ii) the Cµ3 and Cµ4 regions of the human µ heavy chain. The resulting multivalent IgA antibody is expressed in mammalian cells, such as NS0, CHO or HEK293 cells, purified from culture supernatant of using a Jacalin lectin column or other standard procedures, and characterized with gel filtration and SDS-PAGE.

Example 15

Multivalent Fc Fusion Proteins

The technology invented in this work to generate multivalent IgG antibodies is also applicable to generation of multivalent Fc fusion proteins. For example, the pCh9G6-MVIgG1 vector is modified in such a way that (i) the VH and CH1 exons are removed, (ii) a cDNA-derived fragment encoding the signal peptide and extracellular region of human TRAIL (TRAIL EC) is fused in frame to the first amino acid of the hinge exon, and (iii) the light chain transcription unit is eliminated. A flexible polypeptide linker, such as Thr-Gly-Gly-Gly, may be placed between TRAIL and the hinge region. The resulting Fc fusion protein (TRAIL-MVFc) is composed of, from the N-terminus to the C-terminus, (i) TRAIL EC, (ii) the hinge, CH2 and CH3 regions of the human gamma-1 heavy chain, and then (iii) the Cµ3 and Cµ4 regions of the human µ heavy chain. Such Fc fusion proteins are produced as a pentamer or hexamer in mammalian cells. The biological activity of such multimeric Fc fusion proteins to induce apoptosis of cells expressing DR4 or DR5 is analyzed by standard procedures.

Example 16

Multispecific Fc Fusion Proteins

The technology for production of multivalent Fc fusion proteins is further applicable to generation of multispecific Fc fusion proteins. For example, three vectors are constructed for expression of three different Fc fusion proteins. The first expression vector encodes the extracellular region of human TNF receptor type II (TNFR-II EC) fused to the hinge, CH2 and CH3 regions of the human gamma-1 heavy chain, which is further fused to the Cµ3 and Cµ4 regions of the human µ heavy chain (TNFR-II-MVFc). The second vector encodes the extracellular region of human LFA-3 fused to the hinge, CH2 and CH3 regions of the human gamma-1 heavy chain, which is further fused to the Cµ3 and Cµ4 regions of the human µ heavy chain (LFA-3-MVFc). The third vector encodes the extracellular region of human IL-1 receptor fused to the hinge, CH2 and CH3 regions of the human gamma-1 heavy chain, which is further fused to the Cµ3 and Cµ4 regions of the human µ heavy chain (IL-1R-MVFc). TNFR-II-MVFc, LFA-3-MVFc and IL-1R-MVFc are expressed simultaneously to generate multivalent Fc fusion proteins that are capable of binding to TNFα, CD2 (a receptor of LFA-3), and IL-1. The efficacy of such multispecific, multivalent Fc fusion proteins to treat inflammatory diseases is studied using standard methods.

Example 17

Multivalent Proteins Composed of IgG Antibodies and Fc Fusion Proteins

The technology for production of multivalent IgG antibodies and Fc fusion proteins is also applicable for generation of multivalent proteins composed of both IgG antibodies and Fc fusion proteins. For example, mammalian cells are cotransfected with two expression vectors: (i) an expression vector for production of multivalent anti-DR5 IgG antibodies, and (ii) an expression vector for production of multivalent TRAIL-Fc fusion proteins. The expressed multimeric proteins are composed of both anti-DR5 IgG antibodies and TRAIL-Fc fusion proteins. The biological activity of such proteins to induce DR4- and DR5-mediated apoptosis is analyzed by standard procedures.

Example 18

Bispecific Multivalent Antibody

The vectors pCh9G6-MVIgG1 and pChSan11-MVIgG1, which express multivalent IgG1 antibodies binding to human CD79a and CD30, respectively, were either individually or together transfected into HEK293 cells using Lipofectamine 2000 (Invitrogen) according to the supplier's protocol. HEK293 cells were then incubated in DME medium containing 10% FBS for 4 days at 37° C. in a 7.5% $CO_2$ incubator. Antigen binding of transiently expressed antibodies in culture supernatants was tested with the following two formats of ELISA.

In the first format of ELISA, wells of a microtiter plate were coated with recombinant human CD30 extracellular region fused at the C-terminus to the Fc region of human γ1 chain (CD30-Fc; SEQ ID NO:37). After blocking the wells with Block Buffer, appropriately diluted culture supernatants of HEK293 cells were applied to the wells and incubated overnight at 4° C. After washing wells with Wash Buffer, recombinant human CD79a extracellular region fused at the C-terminus to the human λ2 constant region (CD79a-Cλ; SEQ ID NO:38) in ELISA Buffer was applied to the wells. A cysteine residue at the second location from the carboxyl terminal in the human λ2 constant region was changed to a serine residue in CD79a-Cλ. After incubating the ELISA plate for 1 hr at room temperature and washing the wells with Wash Buffer, bound CD79a-Cλ, was detected by HRP-conjugated goat anti-human λ, chain polyclonal antibody. Color development was initiated by adding ABTS substrate and stopped with 2% oxalic acid. Absorbance was read at 405 nm.

Culture supernatants of HEK293 cells transfected with either pCh9G6-MVIgG1 or pChSan11-MVIgG1 showed no signal in this first format of ELISA when compared to the culture supernatant of untransfected HEK293 cells. When pCh9G6-MVIgG1 and pChSan11-MVIgG1 were cotransfected into HEK293 cells, the culture supernatant showed a strong signal in this format of ELISA, indicating the presence of bispecific antibodies that can bind simultaneously to CD79a-Cλ in solution and CD30-Fc coated on the ELISA plate.

In the second format of ELISA, wells of a microtiter plate were coated with recombinant human CD79a extracellular region fused at the C-terminus to the Fc region of human γ1 chain (CD79a-Fc; SEQ ID NO:39). After blocking the wells with Block Buffer, appropriately diluted culture supernatants of HEK293 cells were applied to the wells and incubated overnight at 4° C. After washing wells with Wash Buffer, recombinant human CD30 extracellular region fused at the C-terminus to the human λ2 constant region (CD30-Cλ; SEQ ID NO:40) in ELISA Buffer was applied to the wells. A cysteine residue at the second location from the carboxyl terminal in the human λ2 constant region was changed to a serine residue in CD30-Cλ. After incubating the ELISA plate for 1 hr at room temperature and washing the wells with Wash Buffer, bound CD30-Cλ was detected by HRP-conjugated goat anti-human λ chain polyclonal antibody. Color development was initiated by adding ABTS substrate and stopped with 2% oxalic acid. Absorbance was read at 405 nm.

Culture supernatants of HEK293 cells transfected with either pCh9G6-MVIgG1 or pChSan11-MVIgG1 showed no signal in this second format of ELISA when compared to the culture supernatant of untransfected HEK293 cells. On the other hand, the culture supernatant of HEK293 cells cotransfected with pCh9G6-MVIgG1 and pChSan11-MVIgG1 showed a strong signal in the second format of ELISA, confirming the presence of bispecific antibodies that can bind to both CD79a and CD30.

The amino acid sequence of the recombinant human CD30 extracellular region fused at the C-terminus to the Fc region of human gamma-1 chain (CD30-Fc) is:

(SEQ ID NO: 37)
FPQDRPFEDTCHGNPSHYYDKAVRRCCYRCPMGLFPTQQCPQRPTDCRKQCEPDYY

LDEADRCTACVTCSRDDLVEKTPCAWNSSRVCECRPGMFCSTSAVNSCARCFFHSV

CPAGMIVKFPGTAQKNTVCEPASPGVSPACASPENCKEPSSGTIPQAKPTPVSPATSSA

STMPVRGGTRLAQEAASKLTRAPDSPSSVGRPSSDPGLSPTQPCPEGSGDCRKQCEPD

-continued

YYLDEAGRCTACVSCSRDDLVEKTPCAWNSSRTCECRPGMICATSATNSCARCVPY

PICAAETVTKPQDMAEKDTTFEAPPLGTQPDCNPTPENGEAPASTSPTQSLLVDSQAS

KTLPIPTSAPVALSSTGKPVLDTGGGEPKSCDKTHTCPPCPAPELLGGPSVFLFPPKPK

DTLMISRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSRDELTKN

QVSLTCLVKGFYPSDIAVEWESNGQPENNYKTTPPVLDSDGSFFLYSKLTVDKSRWQ

QGNVFSCSVMHEALHNHYTQKSLSLSPGK.

The amino acid sequence of the recombinant human CD79a extracellular region fused at the C-terminus to the human λ2 constant region (CD79a-Cλ) is:

(SEQ ID NO: 38)
ALWMHKVPASLMVSLGEDAHFQCPHNSSNNANVTWWRVLHGNYTWPPEF

LGPGEDPNGTLIIQNVNKSHGGIYVCRVQEGNESYQQSCGTYLRVRQPP

PRPFLDMGEGTKNRTGGGGQPKAAPSVTLFPPSSEELQANKATLVCLIS

DFYPGAVTVAWKADSSPVKAGVETTTPSKQSNNKYAASSYLSLTPEQWK

SHRSYSCQVTHEGSTVEKTVAPTESS.

The amino acid sequence of the recombinant human CD79a extracellular region fused at the C-terminus to the Fc region of human gamma-1 chain (CD79a-Fc) is:

(SEQ ID NO: 39)
ALWMHKVPASLMVSLGEDAHFQCPHNSSNNANVTWWRVLHGNYTWPPEF

LGPGEDPNGTLIIQNVNKSHGGIYVCRVQEGNESYQQSCGTYLRVRQPP

PRPFLDMGEGTKNRTGGGEPKSCDKTHTCPPCPAPELLGGPSVFLFPPK

PKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPGK.

The amino acid sequence of the recombinant human CD30 extracellular region fused at the C-terminus to the human λ2 constant region (CD30-Cλ) is:

(SEQ ID NO: 40)
FPQDRPFEDTCHGNPSHYYDKAVRRCCYRCPMGLFPTQQCPQRPTDCRKQCEPDYY

LDEADRCTACVTCSRDDLVEKTPCAWNSSRVCECRPGMFCSTSAVNSCARCFFHSV

CPAGMIVKFPGTAQKNTVCEPASPGVSPACASPENCKEPSSGTIPQAKPTPVSPATSSA

STMPVRGGTRLAQEAASKLTRAPDSPSSVGRPSSDPGLSPTQPCPEGSGDCRKQCEPD

YYLDEAGRCTACVSCSRDDLVEKTPCAWNSSRTCECRPGMICATSATNSCARCVPY

PICAAETVTKPQDMAEKDTTFEAPPLGTQPDCNPTPENGEAPASTSPTQSLLVDSQAS

KTLPIPTSAPVALSSTGKPVLDTGGGGQPKAAPSVTLFPPSSEELQANKATLVCLISDF

YPGAVTVAWKADSSPVKAGVETTTPSKQSNNKYAASSYLSLTPEQWKSHRSYSCQV

THEGSTVEKTVAPTESS.

Example 19

Therapeutic Efficacy of the Multimeric Anti-DR4 IgG Antibody in a Mouse Systemic Xenograft Model with Ramos Cells The mouse hybridoma producing the anti-human death receptor 4 (DR4; also called Apo2, TRAIL receptor 1 and TNFRSF10A) monoclonal IgG1/lambda antibody YON007 was generated at JN Biosciences (Mountain View, Calif.) using the extracellular region of human DR4 fused to the Fc region of human gamma-1 heavy chain (DR4-Fc) (SEQ ID NO:41) as an immunogen and following standard hybridoma techniques.

The amino acid sequence of YON007 VH and VL was determined by standard experimental procedures such as the method described by Tsurushita et al. (supra). The amino acid sequence of YON007 VH, including the signal peptide sequence, is (SEQ ID NO: 42)
MNRLTSSLLLLIVPAYVLSQVTLKESGPGILQPSQTLSLTCSFSGFSLST

SGMGVSWIRQPSGKGLEWLAHIYWDDDKRYNPSLKSRLKISKDTSSNQVF

LKITSVDTADTATYYCTRRGEYGNFDYWGQGTTLTVSS (U.S.

61/679,045).

The mature YON007 VH starts at position 20 in SEQ ID NO:42. The amino acid sequence of YON007 VL, including the signal peptide sequence, is (SEQ ID NO: 43)
MAWISLILSLLALSSGAISQAVVTQESALTTSPGETVTLTCRSSSGAVTT

SNFANWVQEKPDHLFTGLIGGTNNRAPGVPARFSGSLIGDKAALTITGAQ

TEDEAIYFCALWYSNHWVFGGGTKLTVL (U.S. 61/679,045).

The mature YON007 VL starts at position 20 in SEQ ID NO:43.

Humanization of YON007 VH and VL was carried out by the procedure described by Tsurushita et al. (supra). The amino acid sequence of humanized YON007 (HuYON007) VH, including the signal peptide, is (SEQ ID NO: 44)
MNRLTSSLLLLIVPAYVLSQVTLRESGPALVKPTQTLTLTCTFSGFSLST

SGMGVSWIRQPPGKALEWLAHIYWDDDKRYNPSLKSRLTISKDTSKNQVV

LTMTNMDPVDTATYYCTRRGEYGNFDYWGQGTLVTVSS (U.S.

61/679,045).

The mature HuYON007 VH sequence starts at position 20 in SEQ ID NO:44.

The amino acid sequence of humanized YON007 (HuYON007) VL is (SEQ ID NO: 45)
MAWISLILSLLALSSGAISQTVVTQEPSFSVSPGGTVTLTCRSSSGAVTT

SNFANWVQQTPGQAPRGLIGGTNNRAPGVPDRFSGSLLGNKAALTITGAQ

ADDESDYYCALWYSNHWVFGGGTKLTVL (U.S. 61/679,045).

The mature HuYON007 VL sequence starts at position 20 in SEQ ID NO:45.

A gene encoding HuYON007 VH (SEQ ID NO:46) was synthesized as an exon including a splice donor signal at the 3' end of the coding region, an SpeI site at the 5' end of the fragment, and a HindIII site at the 3' end of the fragment. A gene encoding HuYON007 VL (SEQ ID NO:47) was synthesized as an exon including a splice donor signal at the 3' end of the coding region, a NheI site at the 5' end of the fragment, and an EcoRI site at the 3' end of the fragment.

The structure of the mammalian expression vector pHuYON007 for production of a humanized anti-human DR4 monoclonal IgG1/lambda antibody, HuYON007-IgG1, is essentially identical to the structure of pCh9G6-IgG1 (FIG. 1) except that (1) the 9G6 VH gene was replaced with the HuYON007 VH gene (SEQ ID NO:46) between the SpeI and HindIII sites, (2) the 9G6 VL gene was replaced with the HuYON007 VL gene (SEQ ID NO:47) between the NheI and EcoRI sites, (3) the Cκ-coding exon was replaced with the exon encoding the human lambda-2 constant region, and (4) the gpt gene was replaced with the puromycin N-acetyl-transferase gene.

The amino acid sequence of the mature heavy chain encoded in pHuYON007 is (SEQ ID NO: 48)
QVTLRESGPALVKPTQTLTLTCTFSGFSLSTSGMGVSWIRQPPGKALEWL

AHIYWDDDKRYNPSLKSRLTISKDTSKNQVVLTMTNMDPVDTATYYCTRR

GEYGNFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK.

The amino acid sequence of the mature light chain encoded in pHuYON007 is (SEQ ID NO: 49)
QTVVTQEPSFSVSPGGTVTLTCRSSSGAVTTSNFANWVQQTPGQAPRGLI

GGTNNRAPGVPDRFSGSILGNKAALTITGAQADDESDYYCALWYSNHWVF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS.

For expression of multimeric HuYON007 IgG antibodies, the coding region of Cμ3 and Cμ4 was fused in frame to the last amino acid of the CH3 exon in pHuYON007. The light chain sequence was not modified. The amino acid sequence of the mature heavy chain encoded in the resultant plasmid, pHuYON007-MVIgG1, is (SEQ ID NO: 50)
QVTLRESGPALVKPTQTLTLTCTFSGFSLSTSGMGVSWIRQPPGKALEWL

AHIYWDDDKRYNPSLKSRLTISKDTSKNQVVLTMTNMDPVDTATYYCTRR

GEYGNFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGKD

QDTAIRVFAIPPSFASIFLTKSTKLTCLVTDLTTYDSVTISWTRQNGEAV

KTHTNISESHPNATFSAVGEASICEDDWNSGERFTCTVTHTDLPSPLKQT

ISRPKGVALHRPDVYLLPPAREQLNLRESATITCLVTGFSPADVFVQWMQ

RGQPLSPEKYVTSAPMPEPQAPGRYFAHSILTVSEEEWNTGETYTCVVAH

EALPNRVTERTVDKSTGKPTLYNVSLVMSDTAGTCY.

The expression vectors pHuYON007 and pHuYON007-MVIgG1 were individually introduced into the chromosome of a Chinese hamster ovary cell line CHO-S (Invitrogen) to obtain cell lines stably producing humanized IgG1/lambda antibodies HuYON007-IgG1 and HuYON007-MVIgG1, respectively. CHO-S cells were grown in SFM4-CHO media (HyClone) at 37° C. in a 7.5% $CO_2$ incubator. Stable transfection into CHO-S was carried out by electroporation. Before transfection, each expression vector was linearized using FspI. In a typical experiment, approximately $10^7$ cells were transfected with 20 μg of linearized plasmid, suspended in SFM4-CHO, and plated into several 96-well plates after appropriate dilutions of cells. After 48 hr, puromycin was added for selection of stable transfectants. Approximately two weeks after the initiation of selection, culture supernatants of transfectants were assayed for antibody production. Expression of antibodies was measured by sandwich ELISA using goat anti-human gamma heavy chain polyclonal antibody for coating and HRP-conjugated goat anti-human lambda chain antibody for detection of bound HuYON007-IgG1 or HuYON007-MVIgG1 antibody. CHO-S stable transfectants producing each of HuYON007-IgG1 and HuYON007-MVIgG1 were expanded in SFM4-CHO.

After centrifugation and filtration, culture supernatants were loaded onto a Protein A column (HiTrap MABSelect SuRe, GE Healthcare, Piscataway, N.J.). The column was washed with PBS before the antibody was eluted with 0.1 M glycine-HCl (pH 3.0). Buffer of all eluted antibodies was neutralized with 1 M Tris-HCl (pH 8) and then changed to PBS by dialysis. In the gel filtration analysis using a Superose 6 10/300 GL as described above, a single dominant peak corresponding to approximately 150 kDa was observed for HuYON007-IgG1. A single dominant peak corresponding to approximately 1,000 kDa was observed for HuYON007-MVIgG1 in the gel filtration analysis.

The human Burkitt's lymphoma cell line Ramos expresses DR4 on the cell surface (Daniel et al. Blood. 110:4037-4046, 2007). Multimerization of DR4 by cross-linking on the cell surface is known to induce apoptosis of cells (Griffith et al. J. Immunol. 162:2597-2605, 1999). Ramos cells were incubated in RPMI-1640 medium containing 10% FBS in the presence of 200 µg/ml of HuYON007-MVIgG1 or HuYON007-IgG1. The viability of Ramos cells after 24-hr incubation was less than 5% with HuYON007-MVIgG1 whereas the viability was more than 75% with HuYON007-IgG1, indicating that HuYON007-MVIgG1 efficiently induces apoptosis of Ramos cells.

Therapeutic efficacy of HuYON007-MVIgG1 was evaluated using a systemic mouse xenograft model with Ramos cells. CB17 SCID female mice were inoculated on Day 0 with 5×10⁶ Ramos cells intravenously into the tail vein for tumor development. HuYON007-IgG1 (0.5 mg/kg), HuYON007-MVIgG1 (0.5 mg/kg), or PBS was administered intravenously to the tumor-bearing mice on Days 7, 10, 14, 17, 21, 24, 28, and 31. The mice were monitored daily for morbidity and mortality. Mice were euthanized at the onset of hind leg paralysis or when more than 20% of body weight was lost.

Figure 18:
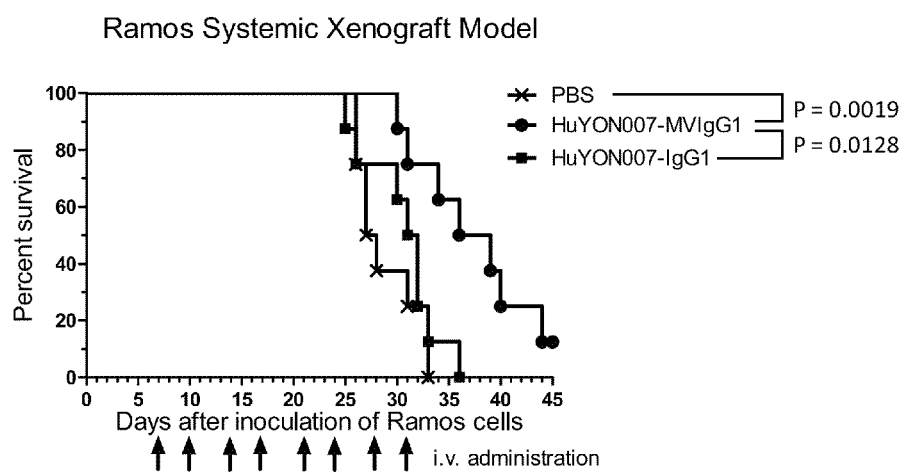
FIG. 18: Survival data of Ramos-bearing CB17 SCID mice treated with HuYON007-MVIgG1 or HuYON007-IgG1.

Mice survival was plotted using the Kaplan-Meier method (FIG. 18) and analyzed for significance using the Mantel-Cox test. The mean survival time was 27.5 days for the PBS-treated group, 31.5 days for the group treated with HuYON007-IgG1, and 37.5 days for the group treated with HuYON007-MVIgG1. The P value between the PBS-treated and HuYON007-MVIgG1-treated groups was 0.0019. The P value between the HuYON007-IgG1-treated and HuYON007-MVIgG1-treated groups was 0.0128. HuYON007-MVIgG1 was significantly more efficacious than HuYon007-IgG1 as therapeutics in the mouse systemic xenograft model with Ramos cells.

Amino acid sequence of the extra-cellular region of human DR4 fused to the Fc region of human gamma-1 heavy chain (DR4-Fc)
SEQ ID NO: 41

```
ASGTEAAAATPSKVWGSSAGRIEPRGGGRGALPTSMGQHGPSARARAGR
APGPRPAREASPRLRVHKTFKFVVVGVLLQVVPSSAATIKLHDQSIGTQ
QWEHSPLGELCPPGSHRSEHPGACNRCTEGVGYTNASNNLFACLPCTAC
KSDEEERSPCTTTRNTACQCKPGTFRNDNSAEMCRKCSTGCPRGMVKVK
DCTPWSDIECVHKESGNGHNTGGGEPKSCDKTHTCPPCPAPELLGGPSV
FLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPGK
```

Nucleotide sequence of an exon encoding HuYON007 VH
SEQ ID NO: 46

```
ACTAGTACCACCATGAACAGGCTTACTTCCTCATTGCTGCTGCTGATTG
TCCCTGCATATGTCCTGTCCCAGGTCACCTTGAGGGAGTCTGGTCCTGC
CCTGGTGAAACCCACACAGACCCTCACACTGACCTGCACCTTCTCTGGG
TTCTCACTCAGCACTTCTGGTATGGGTGTGAGCTGGATCAGACAGCCCC
CAGGGAAGGCCCTGGAGTGGCTTGCACACATTTACTGGGATGATGACAA
GCGCTATAACCCATCCCTGAAGAGCAGGCTCACCATCTCCAAGGACACC
TCCAAAAACCAAGTGGTCCTTACAATGACCAACATGGACCCTGTCGACA
CAGCCACCTATTACTGTACTCGGAGAGGGGAGTATGGTAACTTCGACTA
CTGGGGCCAGGGAACCCTGGTCACCGTCTCCTCAGGTGAGTCTGCTGTA
CTGAAGCTT
```

Nucleotide sequence of an exon encoding HuYON007 VL
SEQ ID NO: 47

```
GCTAGCACCACCATGGCCTGGATTTCACTTATCCTCTCTCTCCTGGCTC
TCAGCTCAGGGGCCATTTCCCAGACTGTCGTGACCCAGGAGCCATCCTT
CTCAGTGTCCCCTGGAGGGACAGTCACACTCACTTGTCGCTCAAGTTCT
GGGGCTGTTACAACCAGTAACTTTGCCAACTGGGTCCAGCAGACCCCAG
GCCAGGCTCCACGCGGCCTCATCGGCGGTACCAACAACCGAGCTCCAGG
GGTCCCTGATCGCTTCTCTGGCTCCATCCTTGGGAACAAAGCTGCCCTC
ACCATCACCGGGGCCCAGGCAGATGATGAATCTGATTATTACTGTGCTC
TATGGTACAGCAACCACTGGGTGTTCGGCGGAGGGACCAAGCTGACCGT
CCTAGGTGAGTCTCTTCTCCCCGAATTC
```

What is claimed is:

1. An antibody comprising an immunoglobulin heavy chain constant region, comprising in order form N- to C-terminus CH2 and CH3 regions, each of which is of IgG or IgA isotype, and Cµ3 and Cµ4 regions, wherein the heavy chain constant region is fused to a heavy chain variable region and the antibody further comprises a light chain comprising a light chain variable region and constant region and the antibody is a component of a multi-specific antibody comprising a plurality of such antibodies with different heavy chain variable regions, and optionally different light chain variable regions; the plurality of antibodies being complexed in the multi-specific antibody via the Cµ3 and Cµ4 regions.

2. An antibody comprising an immunoglobulin heavy chain constant region, comprising in order form N- to C-terminus CH2 and CH3 regions, each of which is of IgG or IgA isotype, and Cµ3 and Cµ4 regions, wherein the antibody is a single-chain antibody comprising a single-chain Fv linked to the heavy chain constant region and the antibody is a component of a multi-specific antibody comprising a plurality of such single-chain antibodies, wherein the scFvs of the plurality have different VH regions, and the plurality of single-chain antibodies are complexed in the multi-specific antibody via the Cµ3 and Cµ4 regions.

3. The antibody of claim 2, wherein the scFvs have the same VL region.

4. The antibody of claim 1 or 2 that is a component of a multispecific complex further comprising a fusion protein, the fusion protein comprising an immunoglobulin heavy chain constant region linked to a heterologous polypeptide, the heavy chain constant region comprising in order from N- to C-terminus CH2 and CH3 regions, each of which is of IgG or IgA isotype, and CO and CO regions, the antibody and fusion protein being complexed via their CO and CO regions.

5. The antibody of claim 1 or 2 that specifically binds the extracellular domain of a receptor.

6. An antibody comprising an immunoglobulin heavy chain constant region, comprising in order from N- to C-terminus CH2 and CH3 regions, each of which is of IgG or IgA isotype, and Cµ3 and Cµ4 regions, wherein the antibody specifically binds to CD79a, CD30, or DR5.

7. The antibody of claim 1 or 6, wherein the immunoglobulin heavy chain further comprises a hinge region N-terminal to the CH2 region.

8. The antibody of claim 1 or 6, wherein the immunoglobulin heavy chain further comprises a CH1 region N-terminal to the hinge region.

9. The antibody of claim 6, wherein the heavy chain constant region is fused to a heavy chain variable region and the antibody further comprises a light chain comprising a light chain variable region and constant region.

10. The antibody of claim 6, wherein the CH1 region, and hinge region, if present, and the CH2 and CH3 regions are IgG1 regions.

11. The antibody of claim 6, wherein the CH1 region and hinge region, if present, and the CH2 and CH3 regions are IgG2 regions.

12. The antibody of claim 6, wherein the CH1 region and the hinge region, if present, and the CH2 and CH3 regions are IgG3 regions.

13. The antibody of claim 6, wherein the CH1 region and the hinge region, if present, and the CH2 and CH3 regions are IgG4 regions.

14. The antibody of claim 6, wherein the CH1 region, if present, and the CH2 and CH3 regions are IgA regions.

15. The antibody of claim 6, wherein the CH1 region, and the hinge region, if present, and the CH2 and CH3 regions are human CH1, hinge, CH2 and CH3 regions and the Cµ3 and Cµ4 regions are human Cµ3 and Cµ4 regions.

16. The antibody of claim 6, which is a single-chain antibody comprising a single-chain Fv linked to the heavy chain constant region.

17. The antibody of claim 6, wherein the antibody is a humanized, chimeric, veneered or human antibody.

18. The antibody of claim 6 that is conjugated to a toxic moiety.

19. The antibody of claim 18, wherein the toxic moiety is cytotoxic.

20. A pharmaceutical composition comprising an antibody as defined in claim 6.

21. The antibody of claim 1, 2 or 6 in the form of a multimer comprising at least five or six copies of a unit comprising two of the heavy chains and two of the light chains, the copies being complexed in the multimer via the Cµ3 and Cµ4 regions.

22. The antibody of claim 1, 2, or 6, wherein the CH1 region, if present, the hinge region and CH2 and CH3 regions are IgG and the antibody shows pH-dependent FcRn binding, specifically binds protein G, specifically binds protein A, exhibits ADCC, CDC and/or opsonization.

23. The antibody of claim 1, 2 or 6, wherein the CH1 region, if present, and the hinge region, and CH2 and CH3 regions are human IgG1 regions and the antibody shows pH-dependent FcRn binding, specifically binds protein G, and specifically binds protein A.

24. The antibody of claim 23 that exhibits ADCC, CDC and opsonizaton.

25. The antibody of claim 1, 2, or 6, wherein the CH1 region if present, and the hinge, CH2 and CH3 regions are human IgG2 or IgG4 regions and the antibody shows pH-dependent FcRn binding, specifically binds protein G and specifically binds protein A.

26. The antibody of claim 1, 2 or 6, wherein the CH1 region if present, and the hinge region, and CH2 and CH3 regions are human IgG3 and the antibody shows pH-dependent FcRn binding, and specifically binds protein G.

27. The antibody of claim 26 that exhibits ADCC, CDC and opsonization.

28. The antibody of claim 1, 2 or 6, wherein the CH1, if present, and the CH2 and CH3 regions are human IgA and the antibody binds an Fc alpha receptor.

* * * * *

UNITED STATES PATENT AND TRADEMARK OFFICE
CERTIFICATE OF CORRECTION

PATENT NO. : 8,952,134 B2  
APPLICATION NO. : 13/627929  
DATED : February 10, 2015  
INVENTOR(S) : J. Yun Tso et al.

Page 1 of 1

It is certified that error appears in the above-identified patent and that said Letters Patent is hereby corrected as shown below:

In the Claims, at:

Claim 1,

Column 121, line 49, delete "form"

and replace with --from--

Claim 2,

Column 121, line 61, delete "form"

and replace with --from--

Claim 4,

Column 122, line 59, delete "CO and CO"

and replace with --$C\mu 3$ and $C\mu 4$--

Column 122, line 60, delete "CO and CO"

and replace with --$C\mu 3$ and $C\mu 4$--

Signed and Sealed this  
Twelfth Day of May, 2015

Michelle K. Lee  
*Director of the United States Patent and Trademark Office*

SEQUENCE LISTING

<160> NUMBER OF SEQ ID NOS: 55

<210> SEQ ID NO 1
<211> LENGTH: 139
<212> TYPE: PRT
<213> ORGANISM: Artificial Sequence
<220> FEATURE:

<223> OTHER INFORMATION: Synthesized

<400> SEQUENCE: 1

Met Gly Trp Ser Arg Ile Phe Leu Phe Leu Leu Ser Ile Thr Ala Gly
1               5                   10                  15

Val His Cys Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Ser Thr Ser Trp Met Asn Trp Val Lys Gln Arg Pro Gly Gln Gly Leu
    50                  55                  60

Glu Trp Ile Gly Arg Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Asn
                85                  90                  95

Thr Ala Tyr Met Gln Leu Ser Ser Leu Thr Ser Val Asp Ser Ala Val
            100                 105                 110

Tyr Phe Cys Glu Arg Phe Tyr Tyr Gly Asn Thr Phe Ala Met Asp Tyr
        115                 120                 125

Trp Gly Gln Gly Thr Ser Val Thr Val Ser Ser
    130                 135

<210> SEQ ID NO 2
<211> LENGTH: 132
<212> TYPE: PRT
<213> ORGANISM: Artificial Sequence
<220> FEATURE:
<223> OTHER INFORMATION: Synthesized

<400> SEQUENCE: 2

Met Lys Leu Pro Val Arg Leu Leu Val Leu Met Phe Trp Ile Pro Ala
1               5                   10                  15

Ser Ser Ser Asp Val Leu Met Thr Gln Ile Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys Arg
    130

<210> SEQ ID NO 3
<211> LENGTH: 330
<212> TYPE: PRT
<213> ORGANISM: Artificial Sequence
<220> FEATURE:
<223> OTHER INFORMATION: Synthesized

<400> SEQUENCE: 3

Ala Ser Thr Lys Gly Pro Ser Val Phe Pro Leu Ala Pro Ser Ser Lys

```
                1               5              10              15
            Ser Thr Ser Gly Gly Thr Ala Ala Leu Gly Cys Leu Val Lys Asp Tyr
                            20              25              30

Phe Pro Glu Pro Val Thr Val Ser Trp Asn Ser Gly Ala Leu Thr Ser
                            35              40              45

Gly Val His Thr Phe Pro Ala Val Leu Gln Ser Ser Gly Leu Tyr Ser
                        50              55              60

Leu Ser Ser Val Val Thr Val Pro Ser Ser Leu Gly Thr Gln Thr
             65              70              75              80

Tyr Ile Cys Asn Val Asn His Lys Pro Ser Asn Thr Lys Val Asp Lys
                                85              90              95

Lys Val Glu Pro Lys Ser Cys Asp Lys Thr His Thr Cys Pro Pro Cys
                           100             105             110

Pro Ala Pro Glu Leu Leu Gly Gly Pro Ser Val Phe Leu Phe Pro Pro
                           115             120             125

Lys Pro Lys Asp Thr Leu Met Ile Ser Arg Thr Pro Glu Val Thr Cys
            130                 135             140

Val Val Val Asp Val Ser His Glu Asp Pro Glu Val Lys Phe Asn Trp
            145                 150             155             160

Tyr Val Asp Gly Val Glu Val His Asn Ala Lys Thr Lys Pro Arg Glu
                            165             170             175

Glu Gln Tyr Asn Ser Thr Tyr Arg Val Val Ser Val Leu Thr Val Leu
                        180             185             190

His Gln Asp Trp Leu Asn Gly Lys Glu Tyr Lys Cys Lys Val Ser Asn
                        195             200             205

Lys Ala Leu Pro Ala Pro Ile Glu Lys Thr Ile Ser Lys Ala Lys Gly
            210                 215             220

Gln Pro Arg Glu Pro Gln Val Tyr Thr Leu Pro Pro Ser Arg Asp Glu
            225                 230             235             240

Leu Thr Lys Asn Gln Val Ser Leu Thr Cys Leu Val Lys Gly Phe Tyr
                            245             250             255

Pro Ser Asp Ile Ala Val Glu Trp Glu Ser Asn Gly Gln Pro Glu Asn
                        260             265             270

Asn Tyr Lys Thr Thr Pro Pro Val Leu Asp Ser Asp Gly Ser Phe Phe
                        275             280             285

Leu Tyr Ser Lys Leu Thr Val Asp Lys Ser Arg Trp Gln Gln Gly Asn
                    290             295             300

Val Phe Ser Cys Ser Val Met His Glu Ala Leu His Asn His Tyr Thr
            305                 310             315             320

Gln Lys Ser Leu Ser Leu Ser Pro Gly Lys
                            325             330

<210> SEQ ID NO 4
<211> LENGTH: 106
<212> TYPE: PRT
<213> ORGANISM: Artificial Sequence
<220> FEATURE:
<223> OTHER INFORMATION: Synthesized

<400> SEQUENCE: 4

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
```

```
                 35                  40                  45

Gly Asn Ser Gln Glu Ser Val Thr Glu Gln Asp Ser Lys Asp Ser Thr
         50                  55                  60

Tyr Ser Leu Ser Ser Thr Leu Thr Leu Ser Lys Ala Asp Tyr Glu Lys
         65                  70                  75                  80

His Lys Val Tyr Ala Cys Glu Val Thr His Gln Gly Leu Ser Ser Pro
                         85                  90                  95

Val Thr Lys Ser Phe Asn Arg Gly Glu Cys
                    100                 105

<210> SEQ ID NO 5
<211> LENGTH: 237
<212> TYPE: PRT
<213> ORGANISM: Artificial Sequence
<220> FEATURE:
<223> OTHER INFORMATION: Synthesized

<400> SEQUENCE: 5

Asp Gln Asp Thr Ala Ile Arg Val Phe Ala Ile Pro Pro Ser Phe Ala
          1               5                  10                  15

Ser Ile Phe Leu Thr Lys Ser Thr Lys Leu Thr Cys Leu Val Thr Asp
                         20                  25                  30

Leu Thr Thr Tyr Asp Ser Val Thr Ile Ser Trp Thr Arg Gln Asn Gly
                     35                  40                  45

Glu Ala Val Lys Thr His Thr Asn Ile Ser Glu Ser His Pro Asn Ala
         50                  55                  60

Thr Phe Ser Ala Val Gly Glu Ala Ser Ile Cys Glu Asp Asp Trp Asn
         65                  70                  75                  80

Ser Gly Glu Arg Phe Thr Cys Thr Val Thr His Thr Asp Leu Pro Ser
                         85                  90                  95

Pro Leu Lys Gln Thr Ile Ser Arg Pro Lys Gly Val Ala Leu His Arg
                    100                 105                 110

Pro Asp Val Tyr Leu Leu Pro Pro Ala Arg Glu Gln Leu Asn Leu Arg
                    115                 120                 125

Glu Ser Ala Thr Ile Thr Cys Leu Val Thr Gly Phe Ser Pro Ala Asp
        130                 135                 140

Val Phe Val Gln Trp Met Gln Arg Gly Gln Pro Leu Ser Pro Glu Lys
        145                 150                 155                 160

Tyr Val Thr Ser Ala Pro Met Pro Glu Pro Gln Ala Pro Gly Arg Tyr
                        165                 170                 175

Phe Ala His Ser Ile Leu Thr Val Ser Glu Glu Glu Trp Asn Thr Gly
                    180                 185                 190

Glu Thr Tyr Thr Cys Val Val Ala His Glu Ala Leu Pro Asn Arg Val
                    195                 200                 205

Thr Glu Arg Thr Val Asp Lys Ser Thr Gly Lys Pro Thr Leu Tyr Asn
                210                 215                 220

Val Ser Leu Val Met Ser Asp Thr Ala Gly Thr Cys Tyr
        225                 230                 235

<210> SEQ ID NO 6
<211> LENGTH: 350
<212> TYPE: PRT
<213> ORGANISM: Artificial Sequence
<220> FEATURE:
<223> OTHER INFORMATION: Synthesized

<400> SEQUENCE: 6
```

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Asp Gln Asp Thr Ala Ile Arg Val Phe Ala Ile Pro Pro Ser Phe
        115                 120                 125

Ala Ser Ile Phe Leu Thr Lys Ser Thr Lys Leu Thr Cys Leu Val Thr
    130                 135                 140

Asp Leu Thr Thr Tyr Asp Ser Val Thr Ile Ser Trp Thr Arg Gln Asn
145                 150                 155                 160

Gly Glu Ala Val Lys Thr His Thr Asn Ile Ser Glu Ser His Pro Asn
                165                 170                 175

Ala Thr Phe Ser Ala Val Gly Glu Ala Ser Ile Cys Glu Asp Asp Trp
            180                 185                 190

Asn Ser Gly Glu Arg Phe Thr Cys Thr Val Thr His Thr Asp Leu Pro
        195                 200                 205

Ser Pro Leu Lys Gln Thr Ile Ser Arg Pro Lys Gly Val Ala Leu His
    210                 215                 220

Arg Pro Asp Val Tyr Leu Leu Pro Pro Ala Arg Glu Gln Leu Asn Leu
225                 230                 235                 240

Arg Glu Ser Ala Thr Ile Thr Cys Leu Val Thr Gly Phe Ser Pro Ala
                245                 250                 255

Asp Val Phe Val Gln Trp Met Gln Arg Gly Gln Pro Leu Ser Pro Glu
            260                 265                 270

Lys Tyr Val Thr Ser Ala Pro Met Pro Glu Pro Gln Ala Pro Gly Arg
        275                 280                 285

Tyr Phe Ala His Ser Ile Leu Thr Val Ser Glu Glu Glu Trp Asn Thr
    290                 295                 300

Gly Glu Thr Tyr Thr Cys Val Val Ala His Glu Ala Leu Pro Asn Arg
305                 310                 315                 320

Val Thr Glu Arg Thr Val Asp Lys Ser Thr Gly Lys Pro Thr Leu Tyr
                325                 330                 335

Asn Val Ser Leu Val Met Ser Asp Thr Ala Gly Thr Cys Tyr
            340                 345                 350

<210> SEQ ID NO 7
<211> LENGTH: 567
<212> TYPE: PRT
<213> ORGANISM: Artificial Sequence
<220> FEATURE:
<223> OTHER INFORMATION: Synthesized

<400> SEQUENCE: 7

Ala Ser Thr Lys Gly Pro Ser Val Phe Pro Leu Ala Pro Ser Ser Lys
 1               5                  10                  15
```

-continued

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
     130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
         195                 200                 205

Lys Ala Leu Pro Ala Pro Ile Glu Lys Thr Ile Ser Lys Ala Lys Gly
     210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
         275                 280                 285

Leu Tyr Ser Lys Leu Thr Val Asp Lys Ser Arg Trp Gln Gln Gly Asn
     290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Asp Gln Asp Thr Ala Ile
                325                 330                 335

Arg Val Phe Ala Ile Pro Pro Ser Phe Ala Ser Ile Phe Leu Thr Lys
            340                 345                 350

Ser Thr Lys Leu Thr Cys Leu Val Thr Asp Leu Thr Thr Tyr Asp Ser
         355                 360                 365

Val Thr Ile Ser Trp Thr Arg Gln Asn Gly Glu Ala Val Lys Thr His
     370                 375                 380

Thr Asn Ile Ser Glu Ser His Pro Asn Ala Thr Phe Ser Ala Val Gly
385                 390                 395                 400

Glu Ala Ser Ile Cys Glu Asp Asp Trp Asn Ser Gly Glu Arg Phe Thr
                405                 410                 415

Cys Thr Val Thr His Thr Asp Leu Pro Ser Pro Leu Lys Gln Thr Ile
            420                 425                 430

Ser Arg Pro Lys Gly Val Ala Leu His Arg Pro Asp Val Tyr Leu Leu
```

```
            435                 440                 445
Pro Pro Ala Arg Glu Gln Leu Asn Leu Arg Glu Ser Ala Thr Ile Thr
450                 455                 460

Cys Leu Val Thr Gly Phe Ser Pro Ala Asp Val Phe Val Gln Trp Met
465                 470                 475                 480

Gln Arg Gly Gln Pro Leu Ser Pro Glu Lys Tyr Val Thr Ser Ala Pro
            485                 490                 495

Met Pro Glu Pro Gln Ala Pro Gly Arg Tyr Phe Ala His Ser Ile Leu
        500                 505                 510

Thr Val Ser Glu Glu Trp Asn Thr Gly Glu Thr Tyr Thr Cys Val
    515                 520                 525

Val Ala His Glu Ala Leu Pro Asn Arg Val Thr Glu Arg Thr Val Asp
530                 535                 540

Lys Ser Thr Gly Lys Pro Thr Leu Tyr Asn Val Ser Leu Val Met Ser
545                 550                 555                 560

Asp Thr Ala Gly Thr Cys Tyr
                565

<210> SEQ ID NO 8
<211> LENGTH: 140
<212> TYPE: PRT
<213> ORGANISM: Artificial Sequence
<220> FEATURE:
<223> OTHER INFORMATION: Synthesized

<400> SEQUENCE: 8

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Met His Trp Val Lys Gln Arg Pro Glu Gln Gly Leu
    50                  55                  60

Glu Trp Ile Gly Arg Ile Asp Pro Ala Asn Gly Asp Thr Ile Tyr Asp
65                  70                  75                  80

Pro Asn Phe Gln Gly Lys Ala Thr Ile Thr Ala Tyr Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Gly Tyr Tyr Gly Ser Ser Tyr Trp Tyr Phe Asp
        115                 120                 125

Val Trp Gly Ala Gly Thr Thr Val Thr Val Ser Ser
    130                 135                 140

<210> SEQ ID NO 9
<211> LENGTH: 132
<212> TYPE: PRT
<213> ORGANISM: Artificial Sequence
<220> FEATURE:
<223> OTHER INFORMATION: Synthesized

<400> SEQUENCE: 9

Met Glu Ser Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30
```

```
Val Ser Leu Gly Gln Arg Ala Thr Ile Ser Cys Arg Ala Ser Glu Ser
        35                  40                  45

Val Glu Tyr Tyr Gly Thr Gly Leu Met Gln Trp Tyr Gln Gln Lys Pro
    50                  55                  60

Gly Gln Pro Pro Lys Leu Leu Ile Tyr Ser Ala Ser Asn Val Glu Ser
65                  70                  75                  80

Gly Val Pro Ala Arg Phe Thr Gly Ser Gly Ser Gly Thr Asp Phe Ser
                85                  90                  95

Leu Asn Ile His Pro Val Glu Asp Asp Ile Ala Met Tyr Phe Cys
                100                 105                 110

Gln Gln Ser Arg Lys Val Pro Trp Thr Phe Gly Gly Gly Thr Lys Leu
            115                 120                 125

Glu Ile Lys Arg
            130

<210> SEQ ID NO 10
<211> LENGTH: 327
<212> TYPE: PRT
<213> ORGANISM: Artificial Sequence
<220> FEATURE:
<223> OTHER INFORMATION: Synthesized

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 11
<211> LENGTH: 564
<212> TYPE: PRT
<213> ORGANISM: Artificial Sequence
<220> FEATURE:
<223> OTHER INFORMATION: Synthesized

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys Asp Gln Asp Thr Ala Ile Arg Val Phe
            325                 330                 335
Ala Ile Pro Pro Ser Phe Ala Ser Ile Phe Leu Thr Lys Ser Thr Lys
            340                 345                 350
Leu Thr Cys Leu Val Thr Asp Leu Thr Thr Tyr Asp Ser Val Thr Ile
            355                 360                 365
Ser Trp Thr Arg Gln Asn Gly Glu Ala Val Lys Thr His Thr Asn Ile
370                 375                 380
Ser Glu Ser His Pro Asn Ala Thr Phe Ser Ala Val Gly Glu Ala Ser
385                 390                 395                 400
Ile Cys Glu Asp Asp Trp Asn Ser Gly Glu Arg Phe Thr Cys Thr Val
                405                 410                 415
Thr His Thr Asp Leu Pro Ser Pro Leu Lys Gln Thr Ile Ser Arg Pro
                420                 425                 430
Lys Gly Val Ala Leu His Arg Pro Asp Val Tyr Leu Leu Pro Pro Ala
            435                 440                 445
Arg Glu Gln Leu Asn Leu Arg Glu Ser Ala Thr Ile Thr Cys Leu Val
    450                 455                 460
Thr Gly Phe Ser Pro Ala Asp Val Phe Val Gln Trp Met Gln Arg Gly
465                 470                 475                 480
Gln Pro Leu Ser Pro Glu Lys Tyr Val Thr Ser Ala Pro Met Pro Glu
                485                 490                 495
Pro Gln Ala Pro Gly Arg Tyr Phe Ala His Ser Ile Leu Thr Val Ser
                500                 505                 510
Glu Glu Glu Trp Asn Thr Gly Glu Thr Tyr Thr Cys Val Val Ala His
        515                 520                 525
Glu Ala Leu Pro Asn Arg Val Thr Glu Arg Thr Val Asp Lys Ser Thr
    530                 535                 540
Gly Lys Pro Thr Leu Tyr Asn Val Ser Leu Val Met Ser Asp Thr Ala
545                 550                 555                 560
Gly Thr Cys Tyr

<210> SEQ ID NO 12
<211> LENGTH: 330
<212> TYPE: PRT
<213> ORGANISM: Artificial Sequence
<220> FEATURE:
<223> OTHER INFORMATION: Synthesized

<400> SEQUENCE: 12

Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Thr Cys Asn Val Asn His Lys Pro Ser Asn Thr Lys Val Asp Lys
```

```
                    85                  90                  95
Arg Val Glu Pro Lys Ser Cys Asp Thr Pro Pro Cys Pro Arg Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Thr Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
                260                 265                 270

Asn Tyr Asn Thr Thr Pro Pro Met Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 13
<211> LENGTH: 350
<212> TYPE: PRT
<213> ORGANISM: Artificial Sequence
<220> FEATURE:
<223> OTHER INFORMATION: Synthesized

<400> SEQUENCE: 13

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Pro Lys Ser Cys Asp Thr Pro Pro Cys Pro Arg Cys
                100                 105                 110

Pro Asp Gln Asp Thr Ala Ile Arg Val Phe Ala Ile Pro Pro Ser Phe
```

```
            115                 120                 125
Ala Ser Ile Phe Leu Thr Lys Ser Thr Lys Leu Thr Cys Leu Val Thr
130                 135                 140

Asp Leu Thr Thr Tyr Asp Ser Val Thr Ile Ser Trp Thr Arg Gln Asn
145                 150                 155                 160

Gly Glu Ala Val Lys Thr His Thr Asn Ile Ser Glu Ser His Pro Asn
                165                 170                 175

Ala Thr Phe Ser Ala Val Gly Glu Ala Ser Ile Cys Glu Asp Asp Trp
            180                 185                 190

Asn Ser Gly Glu Arg Phe Thr Cys Thr Val Thr His Thr Asp Leu Pro
        195                 200                 205

Ser Pro Leu Lys Gln Thr Ile Ser Arg Pro Lys Gly Val Ala Leu His
    210                 215                 220

Arg Pro Asp Val Tyr Leu Leu Pro Pro Ala Arg Glu Gln Leu Asn Leu
225                 230                 235                 240

Arg Glu Ser Ala Thr Ile Thr Cys Leu Val Thr Gly Phe Ser Pro Ala
                245                 250                 255

Asp Val Phe Val Gln Trp Met Gln Arg Gly Gln Pro Leu Ser Pro Glu
            260                 265                 270

Lys Tyr Val Thr Ser Ala Pro Met Pro Glu Pro Gln Ala Pro Gly Arg
        275                 280                 285

Tyr Phe Ala His Ser Ile Leu Thr Val Ser Glu Glu Trp Asn Thr
    290                 295                 300

Gly Glu Thr Tyr Thr Cys Val Val Ala His Glu Ala Leu Pro Asn Arg
305                 310                 315                 320

Val Thr Glu Arg Thr Val Asp Lys Ser Thr Gly Lys Pro Thr Leu Tyr
                325                 330                 335

Asn Val Ser Leu Val Met Ser Asp Thr Ala Gly Thr Cys Tyr
            340                 345                 350

<210> SEQ ID NO 14
<211> LENGTH: 567
<212> TYPE: PRT
<213> ORGANISM: Artificial Sequence
<220> FEATURE:
<223> OTHER INFORMATION: Synthesized

<400> SEQUENCE: 14

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Pro Lys Ser Cys Asp Thr Pro Pro Pro Cys Pro Arg Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

-continued

```
            130                 135                 140
Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Thr Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys Asp Gln Asp Thr Ala Ile
                325                 330                 335

Arg Val Phe Ala Ile Pro Pro Ser Phe Ala Ser Ile Phe Leu Thr Lys
                340                 345                 350

Ser Thr Lys Leu Thr Cys Leu Val Thr Asp Leu Thr Thr Tyr Asp Ser
            355                 360                 365

Val Thr Ile Ser Trp Thr Arg Gln Asn Gly Glu Ala Val Lys Thr His
            370                 375                 380

Thr Asn Ile Ser Glu Ser His Pro Asn Ala Thr Phe Ser Ala Val Gly
385                 390                 395                 400

Glu Ala Ser Ile Cys Glu Asp Asp Trp Asn Ser Gly Glu Arg Phe Thr
                405                 410                 415

Cys Thr Val Thr His Thr Asp Leu Pro Ser Pro Leu Lys Gln Thr Ile
                420                 425                 430

Ser Arg Pro Lys Gly Val Ala Leu His Arg Pro Asp Val Tyr Leu Leu
            435                 440                 445

Pro Pro Ala Arg Glu Gln Leu Asn Leu Arg Glu Ser Ala Thr Ile Thr
450                 455                 460

Cys Leu Val Thr Gly Phe Ser Pro Ala Asp Val Phe Val Gln Trp Met
465                 470                 475                 480

Gln Arg Gly Gln Pro Leu Ser Pro Glu Lys Tyr Val Thr Ser Ala Pro
                485                 490                 495

Met Pro Glu Pro Gln Ala Pro Gly Arg Tyr Phe Ala His Ser Ile Leu
            500                 505                 510

Thr Val Ser Glu Glu Glu Trp Asn Thr Gly Glu Thr Tyr Thr Cys Val
            515                 520                 525

Val Ala His Glu Ala Leu Pro Asn Arg Val Thr Glu Arg Thr Val Asp
            530                 535                 540

Lys Ser Thr Gly Lys Pro Thr Leu Tyr Asn Val Ser Leu Val Met Ser
545                 550                 555                 560
```

```
Asp Thr Ala Gly Thr Cys Tyr
                565
```

<210> SEQ ID NO 15
<211> LENGTH: 98
<212> TYPE: PRT
<213> ORGANISM: Artificial Sequence
<220> FEATURE:
<223> OTHER INFORMATION: Synthesized

<400> SEQUENCE: 15

```
Ala Ser Thr Lys Gly Pro Ser Val Phe Pro Leu Ala Pro Ser Ser Lys
 1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val
```

<210> SEQ ID NO 16
<211> LENGTH: 15
<212> TYPE: PRT
<213> ORGANISM: Artificial Sequence
<220> FEATURE:
<223> OTHER INFORMATION: Synthesized

<400> SEQUENCE: 16

```
Glu Pro Lys Ser Cys Asp Lys Thr His Thr Cys Pro Pro Cys Pro
 1               5                   10                  15
```

<210> SEQ ID NO 17
<211> LENGTH: 110
<212> TYPE: PRT
<213> ORGANISM: Artificial Sequence
<220> FEATURE:
<223> OTHER INFORMATION: Synthesized

<400> SEQUENCE: 17

```
Ala Pro Glu Leu Leu Gly Gly Pro Ser Val Phe Leu Phe Pro Pro Lys
 1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
             100                 105                 110
```

```
<210> SEQ ID NO 18
<211> LENGTH: 107
<212> TYPE: PRT
<213> ORGANISM: Artificial Sequence
<220> FEATURE:
<223> OTHER INFORMATION: Synthesized

<400> SEQUENCE: 18

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 19
<211> LENGTH: 98
<212> TYPE: PRT
<213> ORGANISM: Artificial Sequence
<220> FEATURE:
<223> OTHER INFORMATION: Synthesized

<400> SEQUENCE: 19

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 20
<211> LENGTH: 12
<212> TYPE: PRT
<213> ORGANISM: Artificial Sequence
<220> FEATURE:
<223> OTHER INFORMATION: Synthesized

<400> SEQUENCE: 20

Glu Arg Lys Cys Cys Val Glu Cys Pro Pro Cys Pro
 1               5                  10

<210> SEQ ID NO 21
<211> LENGTH: 109
<212> TYPE: PRT
<213> ORGANISM: Artificial Sequence
<220> FEATURE:
```

<223> OTHER INFORMATION: Synthesized

<400> SEQUENCE: 21

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Synthesized

<400> SEQUENCE: 22

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 23
<211> LENGTH: 98
<212> TYPE: PRT
<213> ORGANISM: Artificial Sequence
<220> FEATURE:
<223> OTHER INFORMATION: Synthesized

<400> SEQUENCE: 23

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr

```
                65                  70                  75                  80
Tyr Thr Cys Asn Val Asn His Lys Pro Ser Asn Thr Lys Val Asp Lys
                    85                  90                  95

Arg Val

<210> SEQ ID NO 24
<211> LENGTH: 62
<212> TYPE: PRT
<213> ORGANISM: Artificial Sequence
<220> FEATURE:
<223> OTHER INFORMATION: Synthesized

<400> SEQUENCE: 24

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 25
<211> LENGTH: 110
<212> TYPE: PRT
<213> ORGANISM: Artificial Sequence
<220> FEATURE:
<223> OTHER INFORMATION: Synthesized

<400> SEQUENCE: 25

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 26
<211> LENGTH: 107
<212> TYPE: PRT
<213> ORGANISM: Artificial Sequence
<220> FEATURE:
<223> OTHER INFORMATION: Synthesized

<400> SEQUENCE: 26

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45
```

```
Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
                100                 105

<210> SEQ ID NO 27
<211> LENGTH: 98
<212> TYPE: PRT
<213> ORGANISM: Artificial Sequence
<220> FEATURE:
<223> OTHER INFORMATION: Synthesized

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 28
<211> LENGTH: 12
<212> TYPE: PRT
<213> ORGANISM: Artificial Sequence
<220> FEATURE:
<223> OTHER INFORMATION: Synthesized

<400> SEQUENCE: 28

Glu Ser Lys Tyr Gly Pro Pro Cys Pro Ser Cys Pro
1               5                   10

<210> SEQ ID NO 29
<211> LENGTH: 110
<212> TYPE: PRT
<213> ORGANISM: Artificial Sequence
<220> FEATURE:
<223> OTHER INFORMATION: Synthesized

<400> SEQUENCE: 29

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80
```

Gln Asp Trp Leu Asn Gly Lys Glu Tyr Lys Cys Lys Val Ser Asn Lys
            85                  90                  95

Gly Leu Pro Ser Ser Ile Glu Lys Thr Ile Ser Lys Ala Lys
            100                 105                 110

<210> SEQ ID NO 30
<211> LENGTH: 107
<212> TYPE: PRT
<213> ORGANISM: Artificial Sequence
<220> FEATURE:
<223> OTHER INFORMATION: Synthesized

<400> SEQUENCE: 30

Gly Gln Pro Arg Glu Pro Gln Val Tyr Thr Leu Pro Pro Ser Gln Glu
  1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 31
<211> LENGTH: 102
<212> TYPE: PRT
<213> ORGANISM: Artificial Sequence
<220> FEATURE:
<223> OTHER INFORMATION: Synthesized

<400> SEQUENCE: 31

Ala Ser Pro Thr Ser Pro Lys Val Phe Pro Leu Ser Leu Cys Ser Thr
  1               5                  10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro
            100

<210> SEQ ID NO 32
<211> LENGTH: 120
<212> TYPE: PRT
<213> ORGANISM: Artificial Sequence
<220> FEATURE:
<223> OTHER INFORMATION: Synthesized

<400> SEQUENCE: 32

Val Pro Ser Thr Pro Thr Pro Ser Pro Ser Thr Pro Thr Pro
1               5                   10                  15

Ser Pro Ser Cys Cys His Pro Arg Leu Ser Leu His Arg Pro Ala Leu
            20                  25                  30

Glu Asp Leu Leu Leu Gly Ser Glu Ala Asn Leu Thr Cys Thr Leu Thr
            35                  40                  45

Gly Leu Arg Asp Ala Ser Gly Val Thr Phe Thr Trp Thr Pro Ser Ser
50                  55                  60

Gly Lys Ser Ala Val Gln Gly Pro Pro Glu Arg Asp Leu Cys Gly Cys
65                  70                  75                  80

Tyr Ser Val Ser Val Leu Pro Gly Cys Ala Glu Pro Trp Asn His
            85                  90                  95

Gly Lys Thr Phe Thr Cys Thr Ala Ala Tyr Pro Glu Ser Lys Thr Pro
            100                 105                 110

Leu Thr Ala Thr Leu Ser Lys Ser
            115                 120

<210> SEQ ID NO 33
<211> LENGTH: 131
<212> TYPE: PRT
<213> ORGANISM: Artificial Sequence
<220> FEATURE:
<223> OTHER INFORMATION: Synthesized

<400> SEQUENCE: 33

Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
            85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
            115                 120                 125

Thr Cys Tyr
    130

<210> SEQ ID NO 34
<211> LENGTH: 102
<212> TYPE: PRT
<213> ORGANISM: Artificial Sequence
<220> FEATURE:
<223> OTHER INFORMATION: Synthesized

<400> SEQUENCE: 34

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
            35                  40                  45

```
Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
 65                  70                  75                  80

Lys Ser Val Thr Cys His Val Lys His Tyr Thr Asn Pro Ser Gln Asp
                85                  90                  95

Val Thr Val Pro Cys Pro
            100

<210> SEQ ID NO 35
<211> LENGTH: 107
<212> TYPE: PRT
<213> ORGANISM: Artificial Sequence
<220> FEATURE:
<223> OTHER INFORMATION: Synthesized

<400> SEQUENCE: 35

Val Pro Pro Pro Pro Cys Cys His Pro Arg Leu Ser Leu His Arg
 1               5                  10                  15

Pro Ala Leu Glu Asp Leu Leu Leu Gly Ser Glu Ala Asn Leu Thr Cys
                20                  25                  30

Thr Leu Thr Gly Leu Arg Asp Ala Ser Gly Ala Thr Phe Thr Trp Thr
            35                  40                  45

Pro Ser Ser Gly Lys Ser Ala Val Gln Gly Pro Pro Glu Arg Asp Leu
 50                  55                  60

Cys Gly Cys Tyr Ser Val Ser Ser Val Leu Pro Gly Cys Ala Gln Pro
 65                  70                  75                  80

Trp Asn His Gly Glu Thr Phe Thr Cys Thr Ala Ala His Pro Glu Leu
                85                  90                  95

Lys Thr Pro Leu Thr Ala Asn Ile Thr Lys Ser
            100                 105

<210> SEQ ID NO 36
<211> LENGTH: 131
<212> TYPE: PRT
<213> ORGANISM: Artificial Sequence
<220> FEATURE:
<223> OTHER INFORMATION: Synthesized

<400> SEQUENCE: 36

Gly Asn Thr Phe Arg Pro Glu Val His Leu Leu Pro Pro Pro Ser Glu
 1               5                  10                  15

Glu Leu Ala Leu Asn Glu Leu Val Thr Leu Thr Cys Leu Ala Arg Gly
                20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
 50                  55                  60

Gln Gly Thr Thr Thr Phe Ala Val Thr Ser Ile Leu Arg Val Ala Ala
 65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
            115                 120                 125

Thr Cys Tyr
```

130

<210> SEQ ID NO 37
<211> LENGTH: 601
<212> TYPE: PRT
<213> ORGANISM: Artificial Sequence
<220> FEATURE:
<223> OTHER INFORMATION: Synthesized

<400> SEQUENCE: 37

```
Phe Pro Gln Asp Arg Pro Phe Glu Asp Thr Cys His Gly Asn Pro Ser
 1               5                  10                  15

His Tyr Tyr Asp Lys Ala Val Arg Arg Cys Cys Tyr Arg Cys Pro Met
             20                  25                  30

Gly Leu Phe Pro Thr Gln Gln Cys Pro Gln Arg Pro Thr Asp Cys Arg
         35                  40                  45

Lys Gln Cys Glu Pro Asp Tyr Tyr Leu Asp Glu Ala Asp Arg Cys Thr
     50                  55                  60

Ala Cys Val Thr Cys Ser Arg Asp Asp Leu Val Glu Lys Thr Pro Cys
 65                  70                  75                  80

Ala Trp Asn Ser Ser Arg Val Cys Glu Cys Arg Pro Gly Met Phe Cys
                 85                  90                  95

Ser Thr Ser Ala Val Asn Ser Cys Ala Arg Cys Phe Phe His Ser Val
            100                 105                 110

Cys Pro Ala Gly Met Ile Val Lys Phe Pro Gly Thr Ala Gln Lys Asn
        115                 120                 125

Thr Val Cys Glu Pro Ala Ser Pro Gly Val Ser Pro Ala Cys Ala Ser
130                 135                 140

Pro Glu Asn Cys Lys Glu Pro Ser Ser Gly Thr Ile Pro Gln Ala Lys
145                 150                 155                 160

Pro Thr Pro Val Ser Pro Ala Thr Ser Ser Ala Ser Thr Met Pro Val
                165                 170                 175

Arg Gly Gly Thr Arg Leu Ala Gln Glu Ala Ala Ser Lys Leu Thr Arg
            180                 185                 190

Ala Pro Asp Ser Pro Ser Ser Val Gly Arg Pro Ser Ser Asp Pro Gly
        195                 200                 205

Leu Ser Pro Thr Gln Pro Cys Pro Glu Gly Ser Gly Asp Cys Arg Lys
    210                 215                 220

Gln Cys Glu Pro Asp Tyr Tyr Leu Asp Glu Ala Gly Arg Cys Thr Ala
225                 230                 235                 240

Cys Val Ser Cys Ser Arg Asp Asp Leu Val Glu Lys Thr Pro Cys Ala
                245                 250                 255

Trp Asn Ser Ser Arg Thr Cys Glu Cys Arg Pro Gly Met Ile Cys Ala
            260                 265                 270

Thr Ser Ala Thr Asn Ser Cys Ala Arg Cys Val Pro Tyr Pro Ile Cys
        275                 280                 285

Ala Ala Glu Thr Val Thr Lys Pro Gln Asp Met Ala Glu Lys Asp Thr
    290                 295                 300

Thr Phe Glu Ala Pro Pro Leu Gly Thr Gln Pro Asp Cys Asn Pro Thr
305                 310                 315                 320

Pro Glu Asn Gly Glu Ala Pro Ala Ser Thr Ser Pro Thr Gln Ser Leu
                325                 330                 335

Leu Val Asp Ser Gln Ala Ser Lys Thr Leu Pro Ile Pro Thr Ser Ala
            340                 345                 350

Pro Val Ala Leu Ser Ser Thr Gly Lys Pro Val Leu Asp Thr Gly Gly
```

```
            355                 360                 365
Gly Glu Pro Lys Ser Cys Asp Lys Thr His Thr Cys Pro Pro Cys Pro
            370                 375                 380

Ala Pro Glu Leu Leu Gly Gly Pro Ser Val Phe Leu Phe Pro Pro Lys
385                 390                 395                 400

Pro Lys Asp Thr Leu Met Ile Ser Arg Thr Pro Glu Val Thr Cys Val
                405                 410                 415

Val Val Asp Val Ser His Glu Asp Pro Glu Val Lys Phe Asn Trp Tyr
            420                 425                 430

Val Asp Gly Val Glu Val His Asn Ala Lys Thr Lys Pro Arg Glu Glu
            435                 440                 445

Gln Tyr Asn Ser Thr Tyr Arg Val Val Ser Val Leu Thr Val Leu His
            450                 455                 460

Gln Asp Trp Leu Asn Gly Lys Glu Tyr Lys Cys Lys Val Ser Asn Lys
465                 470                 475                 480

Ala Leu Pro Ala Pro Ile Glu Lys Thr Ile Ser Lys Ala Lys Gly Gln
                485                 490                 495

Pro Arg Glu Pro Gln Val Tyr Thr Leu Pro Pro Ser Arg Asp Glu Leu
            500                 505                 510

Thr Lys Asn Gln Val Ser Leu Thr Cys Leu Val Lys Gly Phe Tyr Pro
            515                 520                 525

Ser Asp Ile Ala Val Glu Trp Glu Ser Asn Gly Gln Pro Glu Asn Asn
530                 535                 540

Tyr Lys Thr Thr Pro Pro Val Leu Asp Ser Asp Gly Ser Phe Phe Leu
545                 550                 555                 560

Tyr Ser Lys Leu Thr Val Asp Lys Ser Arg Trp Gln Gln Gly Asn Val
                565                 570                 575

Phe Ser Cys Ser Val Met His Glu Ala Leu His Asn His Tyr Thr Gln
            580                 585                 590

Lys Ser Leu Ser Leu Ser Pro Gly Lys
            595                 600

<210> SEQ ID NO 38
<211> LENGTH: 222
<212> TYPE: PRT
<213> ORGANISM: Artificial Sequence
<220> FEATURE:
<223> OTHER INFORMATION: Synthesized

<400> SEQUENCE: 38

Ala Leu Trp Met His Lys Val Pro Ala Ser Leu Met Val Ser Leu Gly
1               5                   10                  15

Glu Asp Ala His Phe Gln Cys Pro His Asn Ser Ser Asn Ala Asn
            20                  25                  30

Val Thr Trp Trp Arg Val Leu His Gly Asn Tyr Thr Trp Pro Pro Glu
            35                  40                  45

Phe Leu Gly Pro Gly Glu Asp Pro Asn Gly Thr Leu Ile Ile Gln Asn
        50                  55                  60

Val Asn Lys Ser His Gly Gly Ile Tyr Val Cys Arg Val Gln Glu Gly
65                  70                  75                  80

Asn Glu Ser Tyr Gln Gln Ser Cys Gly Thr Tyr Leu Arg Val Arg Gln
                85                  90                  95

Pro Pro Pro Arg Pro Phe Leu Asp Met Gly Glu Gly Thr Lys Asn Arg
            100                 105                 110

Thr Gly Gly Gly Gly Gln Pro Lys Ala Ala Pro Ser Val Thr Leu Phe
```

```
            115                 120                 125
Pro Pro Ser Ser Glu Glu Leu Gln Ala Asn Lys Ala Thr Leu Val Cys
        130                 135                 140

Leu Ile Ser Asp Phe Tyr Pro Gly Ala Val Thr Val Ala Trp Lys Ala
145                 150                 155                 160

Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Arg Ser Tyr Ser Cys Gln Val Thr His Glu
        195                 200                 205

Gly Ser Thr Val Glu Lys Thr Val Ala Pro Thr Glu Ser Ser
        210                 215                 220

<210> SEQ ID NO 39
<211> LENGTH: 348
<212> TYPE: PRT
<213> ORGANISM: Artificial Sequence
<220> FEATURE:
<223> OTHER INFORMATION: Synthesized

<400> SEQUENCE: 39

Ala Leu Trp Met His Lys Val Pro Ala Ser Leu Met Val Ser Leu Gly
1               5                   10                  15

Glu Asp Ala His Phe Gln Cys Pro His Asn Ser Ser Asn Ala Asn
            20                  25                  30

Val Thr Trp Trp Arg Val Leu His Gly Asn Tyr Thr Trp Pro Pro Glu
        35                  40                  45

Phe Leu Gly Pro Gly Glu Asp Pro Asn Gly Thr Leu Ile Ile Gln Asn
    50                  55                  60

Val Asn Lys Ser His Gly Gly Ile Tyr Val Cys Arg Val Gln Glu Gly
65                  70                  75                  80

Asn Glu Ser Tyr Gln Gln Ser Cys Gly Thr Tyr Leu Arg Val Arg Gln
                85                  90                  95

Pro Pro Pro Arg Pro Phe Leu Asp Met Gly Glu Gly Thr Lys Asn Arg
            100                 105                 110

Thr Gly Gly Gly Glu Pro Lys Ser Cys Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
```

```
            260                 265                 270
Phe Tyr Pro Ser Asp Ile Ala Val Glu Trp Glu Ser Asn Gly Gln Pro
                275                 280                 285

Glu Asn Asn Tyr Lys Thr Thr Pro Pro Val Leu Asp Ser Asp Gly Ser
            290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 40
<211> LENGTH: 475
<212> TYPE: PRT
<213> ORGANISM: Artificial Sequence
<220> FEATURE:
<223> OTHER INFORMATION: Synthesized

<400> SEQUENCE: 40

Phe Pro Gln Asp Arg Pro Phe Glu Asp Thr Cys His Gly Asn Pro Ser
1               5                   10                  15

His Tyr Tyr Asp Lys Ala Val Arg Arg Cys Cys Tyr Arg Cys Pro Met
                20                  25                  30

Gly Leu Phe Pro Thr Gln Gln Cys Pro Gln Arg Pro Thr Asp Cys Arg
            35                  40                  45

Lys Gln Cys Glu Pro Asp Tyr Tyr Leu Asp Glu Ala Asp Arg Cys Thr
50                  55                  60

Ala Cys Val Thr Cys Ser Arg Asp Asp Leu Val Glu Lys Thr Pro Cys
65                  70                  75                  80

Ala Trp Asn Ser Ser Arg Val Cys Glu Cys Arg Pro Gly Met Phe Cys
                85                  90                  95

Ser Thr Ser Ala Val Asn Ser Cys Ala Arg Cys Phe Phe His Ser Val
            100                 105                 110

Cys Pro Ala Gly Met Ile Val Lys Phe Pro Gly Thr Ala Gln Lys Asn
        115                 120                 125

Thr Val Cys Glu Pro Ala Ser Pro Gly Val Ser Pro Ala Cys Ala Ser
    130                 135                 140

Pro Glu Asn Cys Lys Glu Pro Ser Ser Gly Thr Ile Pro Gln Ala Lys
145                 150                 155                 160

Pro Thr Pro Val Ser Pro Ala Thr Ser Ser Ala Ser Thr Met Pro Val
                165                 170                 175

Arg Gly Gly Thr Arg Leu Ala Gln Glu Ala Ala Ser Lys Leu Thr Arg
            180                 185                 190

Ala Pro Asp Ser Pro Ser Ser Val Gly Arg Pro Ser Ser Asp Pro Gly
                195                 200                 205

Leu Ser Pro Thr Gln Pro Cys Pro Glu Gly Ser Gly Asp Cys Arg Lys
        210                 215                 220

Gln Cys Glu Pro Asp Tyr Tyr Leu Asp Glu Ala Gly Arg Cys Thr Ala
225                 230                 235                 240

Cys Val Ser Cys Ser Arg Asp Asp Leu Val Glu Lys Thr Pro Cys Ala
                245                 250                 255

Trp Asn Ser Ser Arg Thr Cys Glu Cys Arg Pro Gly Met Ile Cys Ala
            260                 265                 270

Thr Ser Ala Thr Asn Ser Cys Ala Arg Cys Val Pro Tyr Pro Ile Cys
```

```
                    275                 280                 285
Ala Ala Glu Thr Val Thr Lys Pro Gln Asp Met Ala Glu Lys Asp Thr
    290                 295                 300

Thr Phe Glu Ala Pro Pro Leu Gly Thr Gln Pro Asp Cys Asn Pro Thr
305                 310                 315                 320

Pro Glu Asn Gly Glu Ala Pro Ala Ser Thr Ser Pro Thr Gln Ser Leu
                    325                 330                 335

Leu Val Asp Ser Gln Ala Ser Lys Thr Leu Pro Ile Pro Thr Ser Ala
                340                 345                 350

Pro Val Ala Leu Ser Ser Thr Gly Lys Pro Val Leu Asp Thr Gly Gly
                355                 360                 365

Gly Gly Gln Pro Lys Ala Ala Pro Ser Val Thr Leu Phe Pro Pro Ser
    370                 375                 380

Ser Glu Glu Leu Gln Ala Asn Lys Ala Thr Leu Val Cys Leu Ile Ser
385                 390                 395                 400

Asp Phe Tyr Pro Gly Ala Val Thr Val Ala Trp Lys Ala Asp Ser Ser
                405                 410                 415

Pro Val Lys Ala Gly Val Glu Thr Thr Thr Pro Ser Lys Gln Ser Asn
                420                 425                 430

Asn Lys Tyr Ala Ala Ser Ser Tyr Leu Ser Leu Thr Pro Glu Gln Trp
                435                 440                 445

Lys Ser His Arg Ser Tyr Ser Cys Gln Val Thr His Glu Gly Ser Thr
450                 455                 460

Val Glu Lys Thr Val Ala Pro Thr Glu Ser Ser
465                 470                 475

<210> SEQ ID NO 41
<211> LENGTH: 452
<212> TYPE: PRT
<213> ORGANISM: Artificial Sequence
<220> FEATURE:
<223> OTHER INFORMATION: Synthesized

<400> SEQUENCE: 41

Ala Ser Gly Thr Glu Ala Ala Ala Thr Pro Ser Lys Val Trp Gly
  1               5                  10                  15

Ser Ser Ala Gly Arg Ile Glu Pro Arg Gly Gly Arg Gly Ala Leu
                20                  25                  30

Pro Thr Ser Met Gly Gln His Gly Pro Ser Ala Arg Ala Arg Ala Gly
                35                  40                  45

Arg Ala Pro Gly Pro Arg Pro Ala Arg Glu Ala Ser Pro Arg Leu Arg
    50                  55                  60

Val His Lys Thr Phe Lys Phe Val Val Val Gly Val Leu Leu Gln Val
65                  70                  75                  80

Val Pro Ser Ser Ala Ala Thr Ile Lys Leu His Asp Gln Ser Ile Gly
                85                  90                  95

Thr Gln Gln Trp Glu His Ser Pro Leu Gly Glu Leu Cys Pro Pro Gly
                100                 105                 110

Ser His Arg Ser Glu His Pro Gly Ala Cys Asn Arg Cys Thr Glu Gly
                115                 120                 125

Val Gly Tyr Thr Asn Ala Ser Asn Asn Leu Phe Ala Cys Leu Pro Cys
                130                 135                 140

Thr Ala Cys Lys Ser Asp Glu Glu Glu Arg Ser Pro Cys Thr Thr Thr
145                 150                 155                 160

Arg Asn Thr Ala Cys Gln Cys Lys Pro Gly Thr Phe Arg Asn Asp Asn
```

```
                165                 170                 175
Ser Ala Glu Met Cys Arg Lys Cys Ser Thr Gly Cys Pro Arg Gly Met
            180                 185                 190

Val Lys Val Lys Asp Cys Thr Pro Trp Ser Asp Ile Glu Cys Val His
            195                 200                 205

Lys Glu Ser Gly Asn Gly His Asn Thr Gly Gly Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 42
<211> LENGTH: 138
<212> TYPE: PRT
<213> ORGANISM: Artificial Sequence
<220> FEATURE:
<223> OTHER INFORMATION: Synthesized

<400> SEQUENCE: 42

Met Asn Arg Leu Thr Ser Ser Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Asp Lys Arg Tyr
```

```
                65                  70                  75                  80
Asn Pro Ser Leu Lys Ser Arg Leu Lys Ile Ser Lys Asp Thr Ser Ser
                85                  90                  95

Asn Gln Val Phe Leu Lys Ile Thr Ser Val Asp Thr Ala Asp Thr Ala
                100                 105                 110

Thr Tyr Tyr Cys Thr Arg Arg Gly Glu Tyr Gly Asn Phe Asp Tyr Trp
                115                 120                 125

Gly Gln Gly Thr Thr Leu Thr Val Ser Ser
                130                 135

<210> SEQ ID NO 43
<211> LENGTH: 128
<212> TYPE: PRT
<213> ORGANISM: Artificial Sequence
<220> FEATURE:
<223> OTHER INFORMATION: Synthesized

<400> SEQUENCE: 43

Met Ala Trp Ile Ser Leu Ile Leu Ser Leu Leu Ala Leu Ser Ser Gly
  1               5                  10                  15

Ala Ile Ser Gln Ala Val Val Thr Gln Glu Ser Ala Leu Thr Thr Ser
                20                  25                  30

Pro Gly Glu Thr Val Thr Leu Thr Cys Arg Ser Ser Ser Gly Ala Val
                35                  40                  45

Thr Thr Ser Asn Phe Ala Asn Trp Val Gln Glu Lys Pro Asp His Leu
                50                  55                  60

Phe Thr Gly Leu Ile Gly Gly Thr Asn Asn Arg Ala Pro Gly Val Pro
 65                 70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
                100                 105                 110

Tyr Ser Asn His Trp Val Phe Gly Gly Gly Thr Lys Leu Thr Val Leu
                115                 120                 125

<210> SEQ ID NO 44
<211> LENGTH: 138
<212> TYPE: PRT
<213> ORGANISM: Artificial Sequence
<220> FEATURE:
<223> OTHER INFORMATION: Synthesized

<400> SEQUENCE: 44

Met Asn Arg Leu Thr Ser Ser Leu Leu Leu Ile Val Pro Ala Tyr
  1               5                  10                  15

Val Leu Ser Gln Val Thr Leu Arg Glu Ser Gly Pro Ala Leu Val Lys
                20                  25                  30

Pro Thr Gln Thr Leu Thr Leu Thr Cys Thr Phe Ser Gly Phe Ser Leu
                35                  40                  45

Ser Thr Ser Gly Met Gly Val Ser Trp Ile Arg Gln Pro Pro Gly Lys
                50                  55                  60

Ala Leu Glu Trp Leu Ala His Ile Tyr Trp Asp Asp Lys Arg Tyr
 65                 70                  75                  80

Asn Pro Ser Leu Lys Ser Arg Leu Thr Ile Ser Lys Asp Thr Ser Lys
                85                  90                  95

Asn Gln Val Val Leu Thr Met Thr Asn Met Asp Pro Val Asp Thr Ala
                100                 105                 110
```

```
Thr Tyr Tyr Cys Thr Arg Arg Gly Glu Tyr Gly Asn Phe Asp Tyr Trp
            115                 120                 125

Gly Gln Gly Thr Leu Val Thr Val Ser Ser
        130                 135

<210> SEQ ID NO 45
<211> LENGTH: 128
<212> TYPE: PRT
<213> ORGANISM: Artificial Sequence
<220> FEATURE:
<223> OTHER INFORMATION: Synthesized

<400> SEQUENCE: 45

Met Ala Trp Ile Ser Leu Ile Leu Ser Leu Leu Ala Leu Ser Ser Gly
 1               5                  10                  15

Ala Ile Ser Gln Thr Val Val Thr Gln Glu Pro Ser Phe Ser Val Ser
            20                  25                  30

Pro Gly Gly Thr Val Thr Leu Thr Cys Arg Ser Ser Ser Gly Ala Val
        35                  40                  45

Thr Thr Ser Asn Phe Ala Asn Trp Val Gln Gln Thr Pro Gly Gln Ala
    50                  55                  60

Pro Arg Gly Leu Ile Gly Gly Thr Asn Asn Arg Ala Pro Gly Val Pro
65                  70                  75                  80

Asp Arg Phe Ser Gly Ser Leu Leu Gly Asn Lys Ala Ala Leu Thr Ile
                85                  90                  95

Thr Gly Ala Gln Ala Asp Asp Glu Ser Asp Tyr Tyr Cys Ala Leu Trp
            100                 105                 110

Tyr Ser Asn His Trp Val Phe Gly Gly Gly Thr Lys Leu Thr Val Leu
        115                 120                 125

<210> SEQ ID NO 46
<211> LENGTH: 450
<212> TYPE: PRT
<213> ORGANISM: Artificial Sequence
<220> FEATURE:
<223> OTHER INFORMATION: Synthesized

<400> SEQUENCE: 46

Ala Cys Thr Ala Gly Thr Ala Cys Cys Ala Cys Ala Thr Gly Ala
 1               5                  10                  15

Ala Cys Ala Gly Gly Cys Thr Thr Ala Cys Thr Thr Cys Cys Thr Cys
            20                  25                  30

Ala Thr Thr Gly Cys Thr Gly Cys Thr Gly Cys Thr Gly Ala Thr Thr
        35                  40                  45

Gly Thr Cys Cys Cys Thr Gly Cys Ala Thr Ala Thr Gly Thr Cys Cys
    50                  55                  60

Thr Gly Thr Cys Cys Cys Ala Gly Gly Thr Cys Ala Cys Cys Thr Thr
65                  70                  75                  80

Gly Ala Gly Gly Gly Ala Gly Thr Cys Thr Gly Gly Thr Cys Cys Thr
                85                  90                  95

Gly Cys Cys Cys Thr Gly Gly Thr Gly Ala Ala Ala Cys Cys Cys Ala
            100                 105                 110

Cys Ala Cys Ala Gly Ala Cys Cys Cys Thr Cys Ala Cys Ala Cys Thr
        115                 120                 125

Gly Ala Cys Cys Thr Gly Cys Ala Cys Thr Thr Cys Thr Cys Thr
        130                 135                 140

Gly Gly Gly Thr Thr Cys Thr Cys Ala Cys Thr Cys Ala Gly Cys Ala
145                 150                 155                 160
```

```
Cys Thr Thr Cys Thr Gly Gly Thr Ala Thr Gly Gly Thr Gly Thr
                165                 170                 175

Gly Ala Gly Cys Thr Gly Gly Ala Thr Cys Ala Gly Ala Cys Ala Gly
            180                 185                 190

Cys Cys Cys Cys Cys Ala Gly Gly Ala Ala Gly Cys Cys Cys
        195                 200                 205

Thr Gly Gly Ala Gly Thr Gly Gly Cys Thr Thr Gly Cys Ala Cys Ala
    210                 215                 220

Cys Ala Thr Thr Thr Ala Cys Thr Gly Gly Ala Thr Gly Ala Thr
225                 230                 235                 240

Gly Ala Cys Ala Ala Gly Cys Gly Cys Thr Ala Thr Ala Ala Cys Cys
            245                 250                 255

Cys Ala Thr Cys Cys Cys Thr Gly Ala Ala Gly Ala Gly Cys Ala Gly
        260                 265                 270

Gly Cys Thr Cys Ala Cys Cys Ala Thr Cys Thr Cys Cys Ala Ala Gly
    275                 280                 285

Gly Ala Cys Ala Cys Cys Thr Cys Cys Ala Ala Ala Ala Cys Cys
290                 295                 300

Ala Ala Gly Thr Gly Gly Thr Cys Cys Thr Thr Ala Cys Ala Ala Thr
305                 310                 315                 320

Gly Ala Cys Cys Ala Ala Cys Ala Thr Gly Gly Ala Cys Cys Cys Thr
            325                 330                 335

Gly Thr Cys Gly Ala Cys Ala Cys Ala Gly Cys Cys Ala Cys Cys Thr
        340                 345                 350

Ala Thr Thr Ala Cys Thr Gly Thr Ala Cys Thr Cys Gly Gly Ala Gly
    355                 360                 365

Ala Gly Gly Gly Ala Gly Thr Ala Thr Gly Thr Ala Ala Cys
370                 375                 380

Thr Thr Cys Gly Ala Cys Thr Ala Cys Thr Gly Gly Gly Gly Cys Cys
385                 390                 395                 400

Ala Gly Gly Ala Ala Cys Cys Cys Thr Gly Gly Thr Cys Ala Cys
            405                 410                 415

Cys Gly Thr Cys Thr Cys Cys Thr Cys Ala Gly Gly Thr Gly Ala Gly
        420                 425                 430

Thr Cys Thr Gly Cys Thr Gly Thr Ala Cys Thr Gly Ala Ala Gly Cys
    435                 440                 445

Thr Thr
    450

<210> SEQ ID NO 47
<211> LENGTH: 420
<212> TYPE: PRT
<213> ORGANISM: Artificial Sequence
<220> FEATURE:
<223> OTHER INFORMATION: Synthesized

<400> SEQUENCE: 47

Gly Cys Thr Ala Gly Cys Ala Cys Cys Ala Thr Gly Gly
  1               5                  10               15

Cys Cys Thr Gly Gly Ala Thr Thr Cys Ala Cys Thr Thr
            20                 25                 30

Cys Cys Thr Cys Thr Cys Thr Cys Thr Cys Thr Gly Gly Cys Thr
        35                 40                 45

Cys Thr Cys Ala Gly Cys Thr Cys Ala Gly Gly Gly Gly Cys Cys Ala
    50                 55                 60
```

```
Thr Thr Thr Cys Cys Cys Ala Gly Ala Cys Thr Gly Thr Cys Gly Thr
65                  70                  75                  80

Gly Ala Cys Cys Cys Ala Gly Gly Ala Gly Cys Cys Ala Thr Cys Cys
                85                  90                  95

Thr Thr Cys Thr Cys Ala Gly Thr Gly Thr Cys Cys Cys Cys Thr Gly
            100                 105                 110

Gly Ala Gly Gly Gly Ala Cys Ala Gly Thr Cys Ala Cys Ala Cys Thr
        115                 120                 125

Cys Ala Cys Thr Thr Gly Thr Cys Gly Cys Thr Cys Ala Ala Gly Thr
    130                 135                 140

Thr Cys Thr Gly Gly Gly Gly Cys Thr Gly Thr Thr Ala Cys Ala Ala
145                 150                 155                 160

Cys Cys Ala Gly Thr Ala Ala Cys Thr Thr Thr Gly Cys Cys Ala Ala
                165                 170                 175

Cys Thr Gly Gly Gly Thr Cys Cys Ala Gly Cys Ala Gly Ala Cys Cys
            180                 185                 190

Cys Cys Ala Gly Gly Cys Cys Ala Gly Gly Cys Thr Cys Cys Ala Cys
        195                 200                 205

Gly Cys Gly Gly Cys Cys Thr Cys Ala Thr Cys Gly Gly Cys Gly Gly
    210                 215                 220

Thr Ala Cys Cys Ala Ala Cys Ala Ala Cys Cys Gly Ala Gly Cys Thr
225                 230                 235                 240

Cys Cys Ala Gly Gly Gly Gly Thr Cys Cys Cys Thr Gly Ala Thr Cys
                245                 250                 255

Gly Cys Thr Thr Cys Thr Cys Thr Gly Gly Cys Thr Cys Cys Ala Thr
            260                 265                 270

Cys Cys Thr Thr Gly Gly Gly Ala Ala Cys Ala Ala Ala Gly Cys Thr
        275                 280                 285

Gly Cys Cys Cys Thr Cys Ala Cys Cys Ala Thr Cys Ala Cys Cys Gly
    290                 295                 300

Gly Gly Gly Cys Cys Cys Ala Gly Gly Cys Ala Gly Ala Thr Gly Ala
305                 310                 315                 320

Thr Gly Ala Ala Thr Cys Thr Gly Ala Thr Thr Ala Thr Thr Ala Cys
                325                 330                 335

Thr Gly Thr Gly Cys Thr Cys Thr Ala Thr Gly Gly Thr Ala Cys Ala
            340                 345                 350

Gly Cys Ala Ala Cys Cys Ala Cys Thr Gly Gly Gly Thr Gly Thr Thr
        355                 360                 365

Cys Gly Gly Cys Gly Gly Ala Gly Gly Gly Ala Cys Cys Ala Ala Gly
    370                 375                 380

Cys Thr Gly Ala Cys Cys Gly Thr Cys Cys Thr Ala Gly Gly Thr Gly
385                 390                 395                 400

Ala Gly Thr Cys Thr Cys Thr Thr Cys Thr Cys Cys Cys Cys Gly Ala
               405                 410                 415

Ala Thr Thr Cys
            420
```

<210> SEQ ID NO 48
<211> LENGTH: 449
<212> TYPE: PRT
<213> ORGANISM: Artificial Sequence
<220> FEATURE:
<223> OTHER INFORMATION: Synthesized

<400> SEQUENCE: 48

-continued

```
Gln Val Thr Leu Arg Glu Ser Gly Pro Ala Leu Val Lys Pro Thr Gln
 1               5                  10                 15
Thr Leu Thr Leu Thr Cys Thr Phe Ser Gly Phe Ser Leu Ser Thr Ser
            20                  25                 30
Gly Met Gly Val Ser Trp Ile Arg Gln Pro Pro Gly Lys Ala Leu Glu
        35                  40                 45
Trp Leu Ala His Ile Tyr Trp Asp Asp Lys Arg Tyr Asn Pro Ser
    50                  55                 60
Leu Lys Ser Arg Leu Thr Ile Ser Lys Asp Thr Ser Lys Asn Gln Val
 65                 70                  75                 80
Val Leu Thr Met Thr Asn Met Asp Pro Val Asp Thr Ala Thr Tyr Tyr
                85                  90                 95
Cys Thr Arg Arg Gly Glu Tyr Gly Asn Phe Asp Tyr Trp Gly Gln Gly
            100                 105                110
Thr Leu Val Thr Val Ser Ser Ala Ser Thr Lys Gly Pro Ser Val Phe
        115                 120                125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                160
Asn Ser Gly Ala Leu Thr Ser Gly Val His Thr Phe Pro Ala Val Leu
                165                 170                175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                400
Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 49
<211> LENGTH: 215
<212> TYPE: PRT
<213> ORGANISM: Artificial Sequence
<220> FEATURE:
<223> OTHER INFORMATION: Synthesized

<400> SEQUENCE: 49

Gln Thr Val Val Thr Gln Glu Pro Ser Phe Ser Val Ser Pro Gly Gly
 1               5                  10                  15

Thr Val Thr Leu Thr Cys Arg Ser Ser Gly Ala Val Thr Thr Ser
            20                  25                  30

Asn Phe Ala Asn Trp Val Gln Gln Thr Pro Gly Gln Ala Pro Arg Gly
        35                  40                  45

Leu Ile Gly Gly Thr Asn Asn Arg Ala Pro Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

His Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 50
<211> LENGTH: 686
<212> TYPE: PRT
<213> ORGANISM: Artificial Sequence
<220> FEATURE:
<223> OTHER INFORMATION: Synthesized

<400> SEQUENCE: 50

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45
```

-continued

```
Trp Leu Ala His Ile Tyr Trp Asp Asp Asp Lys Arg Tyr Asn Pro Ser
 50                  55                  60
Leu Lys Ser Arg Leu Thr Ile Ser Lys Asp Thr Ser Lys Asn Gln Val
 65                  70                  75                  80
Val Leu Thr Met Thr Asn Met Asp Pro Val Asp Thr Ala Thr Tyr Tyr
                 85                  90                  95
Cys Thr Arg Arg Gly Glu Tyr Gly Asn Phe Asp Tyr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys Asp Gln Asp Thr Ala Ile Arg Val Phe Ala Ile Pro Pro Ser Phe
450                 455                 460
Ala Ser Ile Phe Leu Thr Lys Ser Thr Lys Leu Thr Cys Leu Val Thr
```

-continued

```
                465                 470                 475                 480
Asp Leu Thr Thr Tyr Asp Ser Val Thr Ile Ser Trp Thr Arg Gln Asn
                    485                 490                 495

Gly Glu Ala Val Lys Thr His Thr Asn Ile Ser Glu Ser His Pro Asn
                500                 505                 510

Ala Thr Phe Ser Ala Val Gly Glu Ala Ser Ile Cys Glu Asp Asp Trp
            515                 520                 525

Asn Ser Gly Glu Arg Phe Thr Cys Thr Val Thr His Thr Asp Leu Pro
        530                 535                 540

Ser Pro Leu Lys Gln Thr Ile Ser Arg Pro Lys Gly Val Ala Leu His
545                 550                 555                 560

Arg Pro Asp Val Tyr Leu Leu Pro Pro Ala Arg Glu Gln Leu Asn Leu
                565                 570                 575

Arg Glu Ser Ala Thr Ile Thr Cys Leu Val Thr Gly Phe Ser Pro Ala
                580                 585                 590

Asp Val Phe Val Gln Trp Met Gln Arg Gly Gln Pro Leu Ser Pro Glu
            595                 600                 605

Lys Tyr Val Thr Ser Ala Pro Met Pro Glu Pro Gln Ala Pro Gly Arg
        610                 615                 620

Tyr Phe Ala His Ser Ile Leu Thr Val Ser Glu Glu Glu Trp Asn Thr
625                 630                 635                 640

Gly Glu Thr Tyr Thr Cys Val Val Ala His Glu Ala Leu Pro Asn Arg
                645                 650                 655

Val Thr Glu Arg Thr Val Asp Lys Ser Thr Gly Lys Pro Thr Leu Tyr
                660                 665                 670

Asn Val Ser Leu Val Met Ser Asp Thr Ala Gly Thr Cys Tyr
            675                 680                 685

<210> SEQ ID NO 51
<211> LENGTH: 104
<212> TYPE: PRT
<213> ORGANISM: Artificial Sequence
<220> FEATURE:
<223> OTHER INFORMATION: Synthesized

<400> SEQUENCE: 51

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro
            100

<210> SEQ ID NO 52
<211> LENGTH: 112
<212> TYPE: PRT
<213> ORGANISM: Artificial Sequence
<220> FEATURE:
<223> OTHER INFORMATION: Synthesized
```

-continued

<400> SEQUENCE: 52

Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
            20                  25                  30

Thr Gly Phe Ser Pro Arg Gln Ile Gln Val Ser Trp Leu Arg Glu Gly
        35                  40                  45

Lys Gln Val Gly Ser Gly Val Thr Thr Asp Gln Val Gln Ala Glu Ala
50                  55                  60

Lys Glu Ser Gly Pro Thr Thr Tyr Lys Val Thr Ser Thr Leu Thr Ile
65                  70                  75                  80

Lys Glu Ser Asp Trp Leu Ser Gln Ser Met Phe Thr Cys Arg Val Asp
                85                  90                  95

His Arg Gly Leu Thr Phe Gln Gln Asn Ala Ser Ser Met Cys Val Pro
            100                 105                 110

<210> SEQ ID NO 53
<211> LENGTH: 106
<212> TYPE: PRT
<213> ORGANISM: Artificial Sequence
<220> FEATURE:
<223> OTHER INFORMATION: Synthesized

<400> SEQUENCE: 53

Asp Gln Asp Thr Ala Ile Arg Val Phe Ala Ile Pro Pro Ser Phe Ala
1               5                   10                  15

Ser Ile Phe Leu Thr Lys Ser Thr Lys Leu Thr Cys Leu Val Thr Asp
            20                  25                  30

Leu Thr Thr Tyr Asp Ser Val Thr Ile Ser Trp Thr Arg Gln Asn Gly
        35                  40                  45

Glu Ala Val Lys Thr His Thr Asn Ile Ser Glu Ser His Pro Asn Ala
50                  55                  60

Thr Phe Ser Ala Val Gly Glu Ala Ser Ile Cys Glu Asp Asp Trp Asn
65                  70                  75                  80

Ser Gly Glu Arg Phe Thr Cys Thr Val Thr His Thr Asp Leu Pro Ser
                85                  90                  95

Pro Leu Lys Gln Thr Ile Ser Arg Pro Lys
            100                 105

<210> SEQ ID NO 54
<211> LENGTH: 131
<212> TYPE: PRT
<213> ORGANISM: Artificial Sequence
<220> FEATURE:
<223> OTHER INFORMATION: Synthesized

<400> SEQUENCE: 54

Gly Val Ala Leu His Arg Pro Asp Val Tyr Leu Leu Pro Pro Ala Arg
1               5                   10                  15

Glu Gln Leu Asn Leu Arg Glu Ser Ala Thr Ile Thr Cys Leu Val Thr
            20                  25                  30

Gly Phe Ser Pro Ala Asp Val Phe Val Gln Trp Met Gln Arg Gly Gln
        35                  40                  45

Pro Leu Ser Pro Glu Lys Tyr Val Thr Ser Ala Pro Met Pro Glu Pro
50                  55                  60

Gln Ala Pro Gly Arg Tyr Phe Ala His Ser Ile Leu Thr Val Ser Glu
65                  70                  75                  80

```
Glu Glu Trp Asn Thr Gly Glu Thr Tyr Thr Cys Val Val Ala His Glu
            85                  90                  95

Ala Leu Pro Asn Arg Val Thr Glu Arg Thr Val Asp Lys Ser Thr Gly
            100                 105                 110

Lys Pro Thr Leu Tyr Asn Val Ser Leu Val Met Ser Asp Thr Ala Gly
            115                 120                 125

Thr Cys Tyr
    130

<210> SEQ ID NO 55
<211> LENGTH: 159
<212> TYPE: PRT
<213> ORGANISM: Artificial Sequence
<220> FEATURE:
<223> OTHER INFORMATION: Synthesized

<400> SEQUENCE: 55

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
            85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
            115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp
145                 150                 155
```